US012758357B2

(12) United States Patent
Oelze et al.

(10) Patent No.: US 12,758,357 B2
(45) Date of Patent: Oct. 13, 2026

(54) RADIOLOGICAL CLIPS HAVING ULTRASOUND IDENTIFICATION

(71) Applicant: The Board of Trustees of the University of Illinois, Urbana, IL (US)

(72) Inventors: Michael Oelze, Mahomet, IL (US); Jenna Cario, Champaign, IL (US)

(73) Assignee: The Board of Trustees of the University of Illinois, Urbana, IL (US)

(*) Notice: Subject to any disclaimer, the term of this patent is extended or adjusted under 35 U.S.C. 154(b) by 0 days.

(21) Appl. No.: 18/833,569

(22) PCT Filed: Jan. 12, 2023

(86) PCT No.: PCT/US2023/060555
§ 371 (c)(1),
(2) Date: Jul. 26, 2024

(87) PCT Pub. No.: WO2023/137378
PCT Pub. Date: Jul. 20, 2023

(65) Prior Publication Data

US 2025/0032212 A1 Jan. 30, 2025

Related U.S. Application Data

(60) Provisional application No. 63/309,348, filed on Feb. 11, 2022, provisional application No. 63/299,778, filed on Jan. 14, 2022.

(51) Int. Cl.
*A61B 90/90* (2016.01)
*A61B 8/08* (2006.01)
*A61B 90/00* (2016.01)

(52) U.S. Cl.
CPC .............. *A61B 90/90* (2016.02); *A61B 8/085* (2013.01); *A61B 2090/3908* (2016.02); *A61B 2090/3929* (2016.02); *A61B 2090/3991* (2016.02)

(58) Field of Classification Search
CPC . A61B 8/085; A61B 90/90; A61B 2090/3908; A61B 2090/3929; A61B 2090/3991
See application file for complete search history.

(56) References Cited

U.S. PATENT DOCUMENTS 4,777,630 A 10/1988 Burns
10,098,568 B2 * 10/2018 Gazdzinski .......... A61B 5/4839
(Continued)

OTHER PUBLICATIONS

Litjens, G., et al., A survey on deep learning in medical image analysis. Med Image Anal. 2017;42:60-8 8 .
(Continued)

*Primary Examiner* — Dixomara Vargas
(74) *Attorney, Agent, or Firm* — Benesch Friedlander Coplan & Aronoff LLP

(57) ABSTRACT

A radiological clip for locating marked tissue within a diagnostic ultrasound image may transmit an ultrasound identification (USID) signal within a bandwidth of ultrasound imaging pulses. A same ultrasound imaging array that receives the ultrasound imaging pulses may also receive the USID signal. An ultrasound imaging apparatus may generate an ultrasound image of the tissue that indicates a location and ID of the radiological clip based on the ultrasound imaging pulses and the USID signal received from the radiological clip within the imaging field. The radiological clip may generate an activation signal in response to receiving an ultrasound imaging pulse, generate an identification signal responsive to the activation signal, and transmit a USID signal based on the identification signal. The USID signal may include encoded signals corresponding to different bits within a multiple-bit identification tag to uniquely identify the radiological clip within a diagnostic image.

21 Claims, 23 Drawing Sheets

600

(56) References Cited

U.S. PATENT DOCUMENTS

| | | | | |
|---|---|---|---|---|
| 2014/0221828 | A1 | 8/2014 | McKinnis et al. | |
| 2015/0063072 | A1 | 3/2015 | Deng et al. | |
| 2015/0196369 | A1 | 7/2015 | Glossop | |
| 2016/0045184 | A1 | 2/2016 | Courtney et al. | |
| 2019/0274706 | A1* | 9/2019 | Nott | A61B 17/320092 |
| 2020/0078106 | A1* | 3/2020 | Henderson | A61B 34/25 |
| 2020/0314569 | A1* | 10/2020 | Morgan | H04R 1/22 |
| 2021/0169579 | A1* | 6/2021 | Laviola | A61B 5/065 |
| 2021/0369237 | A1 | 12/2021 | Lee et al. | |
| 2023/0371928 | A1* | 11/2023 | Rajguru | A61B 8/465 |

OTHER PUBLICATIONS

Gentile, LF., et al., Ultrasound-guided segmental mastectomy and excisional biopsy using hydrogel-encapsulated clip localization as an alternative to wire localization. Ann Surg Oncol. 2016; 23(10): 3284-9.

Guiliano, A. E., et al., Locoregional recurrence after sentinel lymph node dissection with or without axillary dissection in patients with sentinel lymph node metastases: the American College of Surgeons Oncology Group Zooi I randomized trial. Ann Surg. 2010;252:426-32.

Guiliano, A. E., et al., Axillary dissection vs No. axillary dissection in women with invasive breast cancer and sentinel node metastasis: a randomized clinical trial. JAMA 2011;305:569-75.

Gong, P., et al., "Ultra-sensitive Ultrasound Microvessel Imaging for Characterizing Benign and Malignant Breast Tumors," Ultrasound in Medicine and Biology (in press).

Guo, Z., et al., "Deep Leaming-Based Image Segmentation on Multimodal Medical Imaging," in IEEE Transactions on Radiation and Plasma Medical Sciences, vol. 3, No. 2, pp. 162-169, Mar. 2019. doi: 10. | 109/TRPMS.2018.2890359.

Guyon, I., et al., "An introduction to variable and feature selection." Journal of machine learning research 3.Mar (2003): 1157-1182.

Halevey, A., et al., The unreasonable effectiveness of data. IEEE Intell Syst. 2009;24:8-12.

Halimu, C, et al., "Empirical Comparison of Area under ROC curve (AUC) and Mathew Correlation Coefficient (MCC) for Evaluating Machine Leaming Algorithms on Imbalanced Datasets for Binary Classification." Proceedings of the 3rd International Conference on Machine Leaming and Soft Computing. ACM, 2019.

Hou, L., et al., "Patch-Based Convolutional Neural Network for Whole Slide Tissue Image Classification," 2016 IEEE Conference on Computer Vision and Pattern Recognition (CVPR), Las Vegas, NV, 2016, pp. 2424-2433. doi: 10. | 109/CVPR.2016.266.

Hruska, D. P., "Improved parameter estimates based on the homodyned K distribution." IEEE transactions on ultrasonics, ferroelectrics, and frequency control 56.11 (2009).

Huang, C, et al., "Debiasing-based Noise Suppression for Ultrafast Ultrasound Microvessel Imaging," IEEE Transactions on Ultrasonics, Ferroelectrics, and Frequency Control, vol. 66, No. 8, pp. 1281-1291, 2019.

Huang, C, et al., "Noninvasive Contrast-Free 3D Evaluation of Tumor Angiogenesis with Ultrasensitive Ultrasound Microvessel Imaging," Scientific Reports, vol. 9, No. 4907, pp. 1-11, 2019.

Hyde, B., et al., "Challenges to 1-125 Seed Localization of Metastatic Axillary Lymph Nodes Following Neoadjuvant Chemotherapy." Journal of Breast Imaging 1.3 (2019): 223-229.

Leevy, J. L., et al., A survey on addressing high-class imbalance in big data. Springer J Big Data. 2018;5:42.

Jung, W. S., et al. "Shear wave elastography in evaluation of cervical lymph node metastasis of papillary thyroid carcinoma: elasticity index as a prognostic implication." Annals of surgical oncology 22.1 (2015): 111-116.

Karaman, S., et al., "Mechanisms of lymphatic metastasis." The Journal of clinical investigation 124.3 (2014): 922-928.

Weiss, K., et al., A survey of transfer learning. J Big Data. 2016;3:9.

Kaushiki, R., et al., , Patch-based system for Classification of Breast Histology images using deep learning, Computerized Medical Imaging and Graphics, vol. 71, 2019, pp. 90-103, doi.org/10.1016/j compmedimag.2018.11.003.

Kim, S., et al. "US-guided clip implantation for tumor localization in breast cancer patients who undergo neoadj uvant chemotherapy: feasibility study." (2013): 51-5 8.

King, M. R., et al., Ultrasonic backscatter coefficients for weakly scattering, agar spheres in agar phantoms. Journal of the Acoustical Society of America, 128, 903-908, 2010.

Lecun, Y et al., "Deep learning." Nature 521, No. 7553, pp. 436-444, 2015.

Lee, E. J., et al. "Diagnostic performances of shear wave elastography: which parameter to use in differential diagnosis of solid breast masses ?. " European radiology 23. 7 (2013): 1803-1811.

Li, J., et al., 2018. Learning to Learn from Noisy Labeled Data. arXiv e-prints arXiv: 1812.05214.

Ling, R., et al. "Lymphatic chemotherapy induces apoptosis in lymph node metastases in a rabbit breast carcinoma model." Journal of drug targeting 13.2 (2005): 137-142.

Lin., S. C., et al., Noninvasive Diagnosis of Nonalcoholic Fatty Liver Disease and Quantification of Liver Fat using a New Quantitative Ultrasound Technique. Clinical Gastroenterology and Hepatology, 13, 1337-1345, 2015.

Litjens, G., et al., 2017. A Survey on Deep Learning in Medical Image Analysis. arXiv e-prints arXiv: 1702.05747.

Liu, X., et al., Learning to Diagnose Cirrhosis with Liver Capsule Guided Ultrasound Image Classification. Sensors 17: 149, 2017.

Liu, X., et al., Learn to Combine Modalities in Multimodal Deep Leaming. arXiv e-prints arXiv: 1805.11730.

Lucci, A., et al. "Surgical complications associated with sentinel lymph node dissection (SLND) plus axillary lymph node dissection compared with SLND alone in the American College of Surgeons Oncology Group Trial Zooi I." Journal of Clinical Oncology 25.24 (2007): 3657-3663.

International (Ludwig) Breast Cancer Study Group. Prognostic importance of occult axillary lymph node micrometastases from breast cancers. Lancet 1990; 335: 1565-68.

Ma, X., et al., Dimensionality-Driven Learning with Noisy Labels. In Proceedings of the International Conference on Machine Leaming (ICML), 2018.

Madsen, E. L., et al. "Tissue-mimicking agar/gelatin materials for use in heterogeneous elastography phantoms." Physics in Medicine & Biology 50.23 (2005): 5597.

Maksuti, E. et al. "Arterial stiffness estimation by shear wave elastography: Validation in phantoms with mechanical testing." Ultrasound in medicine & biology 42.1 (2016): 308-321.

Malter, W., et al. "First reported use of the Faxitron LOCalizer™ Radiofrequency Identification (RFID) system in Europe-A feasibility trial, surgical guide and review for non-palpable breast lesions." m vivo 33.5 (2019): 1559-1564, doi: 10.21873/invivo. 11637.

Mamou, J., et al., "Three-dimensional high-frequency backscatter and envelope quantification of cancerous human lymph nodes," Ultrasound in Medicine and Biology, 37, 345-357, 2011.

Mamou, J., et al., "Quantitative Ultrasound in Soft Tissues," Springer, New York, NY, 2013.

Mango, V., et al., "Evaluation of the Savi Scout surgical guidance system for localization and excision of nonpalpable breast lesions: a feasibility study." American Journal ofRoentgenology 207.4 (2016): W69-W72.

Marshall, M. V., et al. "Near-infrared fluorescence imaging in humans with indocyanine green: a review and update." Open surgical oncology journal (Online) 2.2 (2010): 12.

Moorman, A. M., et al. "Pre-operative ultrasonographic evaluation of axillary lymph nodes in breast cancer patients: For which group still of additional value and in which group cause for special attention ?. " Ultrasound in medicine & biology 41.11 (2015): 2842-2848.

Mori, N., et al. "Perfusion contrast-enhanced ultrasound to predict early lymph-node metastasis in breast cancer." Japanese journal of radiology 3 7.2 (2019): 145-153.

(56) References Cited

OTHER PUBLICATIONS

Nam, K., et al., Ultrasonic attenuation and backscatter coefficient estimates of rodent-tumor mimicking structures: comparison of results among clinical scanners. Ultrasonic Imaging, 33: 233-250, 2011.
Nam, K., et al., Cross-imaging system comparison of backscatter coefficient estimates from a tissue-mimicking material. Journal of the Acoustical Society of America, 132, 1319-1324, 2012.
Nam, H., et al., “Dual attention networks for multimodal reasoning and matching.” arXiv preprint arXiv: 1611.00471 (2016).
National Comprehensive Cancer Network. NCCN clinical practice guidelines in oncology: breast cancer, version 2. 2014. http://www.nccn.org/. Accessed Nov. 2, 2014.
Ngiam, J., et al., 2011, 1. Multimodal deep learning. In Proceedings of the 28th International Conference on International Conference on Machine Leaming (ICML’ 11 ), Lise Getoor and Tobias Scheffer (Eds.). Omnipress, USA, pp. 689-696.
Nguyen, T. J., et al., “Localizing the Clipped Node in Patients with Node-Positive Breast Cancer Treated with Neoadjuvant Chemotherapy: Early Leaming Experience and Challenges.,” Annals of Surgical Oncology, vol. 24, No. 10, pp. 3011-3016, 2017, doi: 10.1245/s10434-01 7-6023-z.
Nguyen, T. J., et al., (2019) Understanding Neural Networks via Feature Visualization: A Survey. In: Samek W., Montavon G., Vedaldi A, Hansen L., Muller KR (eds) Explainable Al: Interpreting, Explaining and Visualizing Deep Leaming. Lecture Notes in Computer Science, vol. 11700.
NIBIB Science Highlights Jun. 10, 2019, “Artificial intelligence enables low-dose CT scans, faster scan time” https://www.nibib.nih.gov/news-events/newsroom/artificia .. intelligence-enables-low-dose-ct-scans-faster-scan-time, accessed Sep. 20, 2019.
Nurco, J., et al., Surgical benefits conveyed by biopsy site marking system using ultrasound localization. Am J Surg. 2005; 190:618-22.
Wang, Y., et al. “Gray-scale contrast-enhanced ultrasonography of sentinel lymph nodes in a metastatic: breast cancer model.” Academic radiology 16. 8 (2009): 957-962.
https://www.wcrf.org/dietandcancer/cancer-trends/worldwide-cancer-data (Last visited Sep. 17, 2019).
Wirtzfeld, L. A., et al., Cross-imaging Platform Comparison of Ultrasonic Backscatter Coefficient Measurements of Live Rat Tumors. Journal of Ultrasound in Medicine, 29, 1117-1123, 2010.
Wirtzfeld, L. A., et al., Techniques and Evaluation from a Cross-platform Imaging Comparison of Quantitative Ultrasound Parameters in an In Vivo Rodent Fibroadenoma Model. IEEE Transactions on Ultrasonics, Ferroelectrics, and Frequency Control, 60, 1386-1400, 2013.
Wirtzfeld, L. A., et al., Quantitative ultrasound comparison of MAT and 4TI mammary tumors in mice and rats across multiple imaging systems. Journal of Ultrasound in Medicine, 34, 1373-1383, 2015.
Wood, R. W., et al., “A Review of Options for Localization of Axillary Lymph Nodes in the Treatment of Invasive Breast Cancer,” Academic Radiology, vol. 26, No. 6, pp. 805-819, 2019, doi:https://doi.org/10.1016/j.acra.2018.07.002.
Xiao, T., et al., Learning From Massive Noisy Labeled Data for Image Classification The IEEE Conference on Computer Vision and Pattern Recognition (CVPR), 2015, pp. 2691-2699.
Xiaojun, L., et al. “Local administration of liposomal adriamycin inhibited proliferation of metastatic cells in axillary lymph nodes in rabbit breast cancer model.” Journal of Medical Colleges of PLA 24.3 (2009): 161-166.
Youk, J. H et al. “Diagnostic value of commercially available shear-wave elastography for breast cancers: integration into BI-RADS classification with subcategories of category 4.” European radiology 23.10 (2013): 2695-2704.
Zhao, J et al. “The value of contrast-enhanced ultrasound for sentinel lymph node identification and characterisation in pre-operative breast cancer patients: A prospective study.” European radiology 28.4 (2018): 1654-1661.
Zhi-Hua, Z., A brief introduction to weakly supervised learning, National Science Review, vol. 5, Issue 1, Jan. 2018, pp. 44-53.
Zhu, J., et al. “3D Super-Resolution US Imaging of Rabbit Lymph Node Vasculature in Vivo by Using Microbubbles.” Radiology 291.3 (2019): 642-650.
Ribeiro, M. T., et al., “”Why Should I Trust You?“ Explaining the Predictions of Any Classifier”, arXiv: 1602.04938v3 [cs.LG] Aug. 9, 2016.
International Search Report and Written Opinion issued in PCT Application No. PCT/US23/60555, mailing date May 17, 2023.
Cario et al., “Design of an electronic radiological clip for improved breast cancer imaging with ultrasound”, The Journal of the Acoustical Society of America, vol. 151, No. 4, May 9, 2022.
Malter, W., et al., “First Reported Use of the Faxitron LOCalizer™ Radiofrequency Identification (RFID) System in Europe—A Feasibility Trial, Surgical Guide and Review for Non-palpable Breast Lesions,” In Vivo 33(5) , 1559-1564.
Nguyen, T., et al., “Localizing the Clipped Node in Patients with Node-Positive Breast Cancer Treated with Neoadjuvant Chemotherapy: Early Learning Experience and Challenges”, Annals of Surgical Oncology 24(6), Aug. 2017.
Ramos, M., et al., “Intraoperative ultrasound in conservative surgery for non-palpable breast cancer after neoadjuvant chemotherapy,” International Journal of Surgery 12(6), 572-577, 2014.
Siegel, R. L., et al., “Cancer Statistics, 2021”, CA Cancer Journal for Clinicians 2021; 71:7-33, 2021.
Tan, M. P., et al., “The ’twinkle’ artifact - a novel method of clip identification to facilitate targeted axillary surgery following neoadjuvant chemotherapy in breast cancer patients”, Clinical Imaging, vol. 68, Dec 2020, pp. 36-44.
Akkus, Z., et al., “A Survey of Deep-Learning Applications in Ultrasound: Artificial Intelligence-Powered Ultrasound for Improving Clinical Workflow”, Journal of the American College of Radiology, vol. 16, Issue 9, Part B, Sep. 2019, pp. 1318-1328.
Alvarez, S., et al. “Role of sonography in the diagnosis of axillary lymph node metastases in breast cancer: a systematic review” American Journal of Roentgenology 186.5 (2006): 1342-1348.
Anderson, J.J., et al., “Interlaboratory Comparison of Backscatter Coefficient Estimates for Tissue-mimicking Phantoms”, Ultrason Imaging. Jan. 2010; 32(1): 48-64.
Ashikaga, T., et al. “National Surgical Adjuvant Breast, Bowel Project. Morbidity results from the Nsabp B-32 trial comparing sentinel lymph node dissection versus axillary dissection.” J Surg Oncol 102.2 (2010): 111-118.
Azizi, G., et al. “Shear wave elastography and cervical lymph nodes: predicting malignancy.” Ultrasound in medicine & biology 42.6 (2016): 1273-1281.
Bayramoglu, Z., et al. “Diagnostic performances of superb microvascular imaging, shear wave elastography and shape index in pediatric lymph nodes categorization: a comparative study.” The British journal of radiology 91.1087 (2018): 20180129.
Bedi, D. G., et al. “Cortical morphologic features of axillary lymph nodes as a predictor of metastasis in breast cancer: in vitro sonographic study.” American Journal of Roentgenology 191.3 (2008): 646-652.
Bigelow, T.A., et al., In Vivo Ultrasound Attenuation Slope Estimates for Detecting Cervical Ripening in Rats: Preliminary Results. Journal of the Acoustical Society of America, 123, 1794-1800, 2008. Pmcid: PMC2637349 (Also, published in the Mar. 15, 2008 issue of Virtual Journal of Biological Physics Research; http://www.vjbio.org).
Black, D. “Axillary ultrasound: for all, for none, to diagnose positive nodes, or to support avoiding sentinel lymph node biopsy altogether.” Annals of surgical oncology 24.1 (2017): 64-69.
Baughey, J. C, et al. “Sentinel lymph node surgery after neoadjuvant chemotherapy in patients with node-positive breast cancer: the Acosog ZI071 (Alliance) clinical trial.” Jama 310.14 (2013): 1455-1461.
Bourke, A. G., et al., “The disappearing clip: an unusual complication in MRI biopsy.” Case Reports 2014 (2014).
Baughey, J. C, et al. “Identification and resection of the clipped node decreases the false negative rate of sentinel lymph node surgery in patients presenting with node positive breast cancer (TO-T4, NI-2) who receive neoadjuvant chemotherapy-results from Acosog ZI071 (Alliance).” Annals of surgery 263.4 (2016): 802.

(56) References Cited

OTHER PUBLICATIONS

Boutrand, Jean-Pierre, ed. Biocompatibility and performance of medical devices. Woodhead Publishing, 2019.
Brattain, L.J., et al., Machine learning for medical ultrasound: status, methods, and future opportunities. Abdom Radiol (NY). Apr. 2018;43(4): 786-799. doi: 10.1007/s00261-018-1517-0. PMID: 29492605; Pmcid: PMC5886811.
Breiman, L. Random forests. Machine Leaming, 45(1): 5-32, 2001.
Brierly, J. D., et al., eds. TNM classification of malignant tumours. John Wiley & Sons, 2016.
Byra, M., et al., Classification of breast lesions using segmented quantitative ultrasound maps of homodyned K distribution parameters. Medical Physics 43, 10: 5561-5569, 2016.
Burbank, F., et al., "Tissue marking clip for stereotactic breast biopsy: initial placement accuracy, long-term stability, and usefulness as a guide for wire localization." Radiology 205.2 (1997): 407-415.
National Cancer Institute; Surveillance, Epidemiology, and End Results Program, Cancer Stat Facts: Female Breast Cancer; https://seer.cancer.gov/statfacts/html/breast.html (Last visited Feb. 9, 2021).
Carter, C., et al., "Relation of tumor size, lymph node status, and survival in 24,740 breast cancer cases." Cancer 63.1 (1989): 181-187.
Caudle, A. S., et al. "Selective surgical localization of axillary lymph nodes containing metastases in patients with breast cancer: a prospective feasibility trial." JAMA surgery150.2 (2015): 137-143.
Caudle, A. S., et al. "Improved axillary evaluation following neoadjuvant therapy for patients with node-positive breast cancer using selective evaluation of clipped nodes: implementation of targeted axillary dissection." Journal of Clinical Oncology 34.10 (2016): 1072.
Chen, S., et al., "Revisting unreasonable effectivness of data in deep learning era", In: ICCV; 2017. p. 843-52.
Chen, S., et al., "Low-Dose CT With a Residual Encoder-Decoder Convolutional Neural Network," in IEEE Transactions on Medical Imaging, vol. 36, No. 12, pp. 2524-2535, Dec 2017.
Cheng, B., et al., 2018. Revisiting Pre-training: An Efficient Training Method for Image Classification. arXiv e-prints arXiv:1811.09347,.
Chiorean, L., et al. "Transcutaneous ultrasound: Elastographic lymph node evaluation. Current clinical applications and literature review." Ultrasound in medicine & biology 42.1 (2016): 16-30.
Choo, J., et al., "Visual Analytics for Explainable Deep Learning" in IEEE Computer Graphics and Applications, vol. 38, No. 04, pp. 84-92, 2018.
Choudhery, S., et al. "Tomosynthesis-guided needle localization of breast and axillary lesions: our initial experience." American Journal of Roentgenology 212.4 (2019): 943-946.
Cohen, T., et al., "(Machine) learning to do more with less", High Energ. Phys. (2018) 2018: 34.
Cortes, C., et al., "Support-vector networks," Machine Learning, 20 (3): 273-297, 1995.
Coron, A., et al. "A quantitative ultrasound-based method and device for reliably guiding pathologists to metastatic regions of dissected lymph nodes." Biomedical Imaging (ISBI), 2012 9th IEEE International Symposium on. IEEE, 2012.
Cote, R. J., et al. "Role of immunohistochemical detection of lymph-node metastases in management of breast cancer." The Lancet 354.9182 (1999): 896-900.
Cristianini, N. et al., "An Introduction to Support Vector Machines and other kernel-based learning methods," Cambridge University Press, 2000.
Criminisi, A., et al., "Decision Forests for Computer Vision and Medical Image Analysis," Springer 2013.
Dehghani, M., et al., 2017. Neural Ranking Models with Weak Supervision. In Proceedings of the 40th International Acm Sigir Conference on Research and Development in Information Retrieval (SIGIR '17). ACM, New York, Ny, USA, 65-74.
Denis, M., et al., "Comb-push Ultrasound Shear Elastography of Breast Masses: Initial Results Show Promise," Plos One, 10(3): e0119398, 2015.
Denis, M., et al., "Update on Breast Cancer Detection Using Comb-push Ultrasound Shear Elastography," IEEE Transactions on Ultrasonics, Ferroelectrics, and Frequency Control, vol. 62, No. 9, pp. 1644-1650, 2015.
Dong, Y., et al., "Preoperative prediction of sentinel lymph node metastasis in breast cancer based on radiomics of T2-weighted fat-suppression and diffusion-weighted MRI." European radiology 28.2 (2018): 582-591.
Chehade, H. E. H., et al., Is sentinel lymph node biopsy a viable alternative to complete axillary dissection following neoadjuvant chemotherapy in women with node-positive breast cancer at diagnosis? An updated meta-analysis involving 3,398 patients. Am J Surg 2016;212(5):969-81.
Escalante, H. J., et al., Explainable and interpretable models in computer vision and machine learning. Springer Verlag, 2018, The Springer Series on Challenges in Machine Leaming, 9783319981307. (10.1007/978-3-319-9813 1-4).
Faran Jr., J. J., Sound scattering by solid cylinders and spheres. J. Acoust. Soc. Am., vol. 23,No. 4,pp. 405-418 , 1951.
Fisher, B., et al., Relation of No. of positive axillary nodes to the prognosis of patients with primary breast cancer: an NSABP update. Cancer 198 3; 52: 1551-57.
Fraile, M., et al. "Sentinel node biopsy as a practical alternative to axillary lymph node dissection in breast cancer patients: an approach to its validity. " Annals of Oncology 11.6 (2000): 701-705.
Frenay, B., et al., "Classification in the Presence of Label Noise: A Survey," in IEEE Transactions on Neural Networks and Learning Systems, vol. 25, No. 5, pp. 845-848 69, May 2014.
Friedman, J., et al., Regularization Paths for Generalized Linear Models via Coordinate Descent. J Stats Software, 33(1), 1-22, 2010.
Oelze, M. L., et al., Characterization of Tissue Microstructure using Ultrasonic Backscatter: Theory and Technique Optimization using a Gaussian Form Factor. Journal of the Acoustical Society of America, 112, 1202-1211, 2002.
Oelze, M. L., et al., "Review of quantitative ultrasound: Envelope statistics and backscatter coefficient imaging and contributions to diagnostic ultrasound." IEEE transactions on ultrasonics, ferroelectrics, and frequency control 63.2 (2016): 336-351.
Oh, K., et al. "Optimizing between data transformation and parametric weighting for stable binary classification." Journal of the Franklin Institute 355.4 (2018): 1614- 1637.
Olah, C., et al., "Feature Visualization", Distill, 2017. Ribeiro, Marco Tulio et al. "Why should I trust you ?: Explaining the predictions of any classifier." SIGKDD 2016.
Ozcan, L. C., et al., "Is Axillary Lymph Node Dissection Necessary After a Positive Sentinel Lymph Node Biopsy ?. " Advances in surgery 51.1 (2017): 165- 178.
Paige, J. S., et al. "A pilot comparative study of quantitative ultrasound, conventional ultrasound, and MRI for predicting histology-determined steatosis grade in adult nonalcoholic fatty liver disease." American Journal of Roentgenology 208.5 (2017): WI68-WI 77.
Park, A. Y., et al. "Shear wave elastography of thyroid nodules for the prediction of malignancy in a large scale study." European journal of radiology 84.3 (2015): 407-412.
Peng A. Y., et al., (2019) Using Supervised Pretraining to Improve Generalization of Neural Networks on Binary Classification Problems. In: BerlingerioM ., Bonchi F., Gartner T., Hurley N., Ifrim G. (eds)Machine Learning and Knowledge Discovery in Databases. ECML PKDD 2018. Lecture Notes in Computer Science, vol. 11051. Springer.
Pilewskie, M et al., Does a positive axillary lymph node needle biopsy result predict the need for axillary lymph node dissection in clinically node-negative breast cancer patients in the Acosog Zooi Era? Ann Surg Oncol, 2016; 23: 1123-1128.
Portnow, L. H., et al. "Biopsy Marker Standardization: What's in a Name ?. " American Journal of Roentgenology 212.6 (2019): 1400-1405.
Qian, C., et al. "Preparing the "soil": the pnmary tumor induces vasculature reorganization in the sentinel lymph node before the arrival of metastatic cancer cells." Cancer research 66.21 (2006): 10365-10376.
Ramos, M., et al., "Intraoperative ultrasound in conservative surgery for non-palpable breast cancer after neoadjuvant chemo-

(56) References Cited

OTHER PUBLICATIONS therapy," International Journal of Surgery, vol. 12, No. 6, pp. 572-577, 2014, doi: https://doi.org/10.1016/j . ijsu.2014.04.003.
Rawat, W., et al., Deep Convolutional Neural Networks for Image Classification: A Comprehensive Review. Neural Comput. Sep. 2017;29(9):2352-2449. doi:10.1162/NECO_a_00990. Epub Jun. 9, 2017.
Razek, A., et al. "Assessment of axillary lymph nodes in patients with breast cancer with diffusion-weighted MR imaging in combination with routine and dynamic contrast MR imaging." Breast cancer 23.3 (2016): 525-532.
Saegusa-Beecroft, E., et al., Three-dimensional quantitative ultrasound for detecting lymph node metastases. J Surg Res, 183:258-269, 2013.
Saharinen, P., et al. "Lymphatic vasculature: development, molecular regulation and role in tumor metastasis and inflammation." Trends in immunology 25.7 (2004): 387-395.
Sakamoto, N., et al. "Evaluation of the dislocation and long-term sonographic detectability of a hydrogel-based breast biopsy site marker." Breast Cancer 25.5 (2018): 575-582.
Sannachi, L., et al., Non-Invasive Evaluation of Breast Cancer Response to Chemotherapy using Quantitative Ultrasonic Backscatter Parameters. Medical Image Analysis, 20, 224-236, 2015.
Sannachi, L., et al., Response monitoring of breast cancer patients receiving neoadjuvant chemotherapy using quantitative ultrasound, texture, and molecular features. PLOS One, 3;13(1): e0189634, 2018.
Seo, M. et al., "Differentiation of benign and metastatic axillary lymph nodes in breast cancer: additive value of shear wave elastography to B-mode ultrasound." Clinical imaging 50 (2018): 258-263.
Shao, L., Transfer learning for visual categorization: a survey. IEEE Trans Neural Netw Learn Syst. 2015;26(5): 1019-34.
Shah, A. D., et al. "Breast tissue markers: Why? What's out there? How do I choose ?. " Clinical imaging 52 (2018): 123-136.
Shan, H., et al., Competitive performance of a modularized deep neural network compared to commercial algorithms for low-dose CT image reconstruction. Nature Machine Intelligence. Jun. 10, 2019.
Shen, D., et al., Deep Learning in Medical Image Analysis, Annual Review of Biomedical Engineering 2017 19: 1, 221-248.
Liu, S., "Deep Learning in Medical Ultrasound Analysis: A Review, Engineering", vol. 5, Issue 2, 2019, pp. 261-275, https://doi.org/10.1016/j.eng.2018.11.020.
Shorten, C., et al., A survey on Image Data Augmentation for Deep Learning, J Big Data (2019) 6: 60.
Siegel, R. L., et al., "Cancer statistics, 2021," Ca: A Cancer Journal for Clinicians 71(1), 7-33, https://acsjournals. onlinelibrary.wiley.com/doi/abs/10.3322/caac2 | 654, doi: https://doi.org/10. 3322/caac2 | 654.
Sim, J. K., et al., "Differentiation Between Malignant and Benign Lymph Nodes: Role of Superb Microvascular Imaging in the Evaluation of Cervical Lymph Nodes." Journal of Ultrasound in Medicine (2019).
Song, P., et al., "Comb-push Ultrasound Shear Elastography (Cuse): A Novel Method for Two-dimensional Shear Elasticity Imaging of Soft Tissues", IEEE Transactions on Medical Imaging, vol. 31, issue 9, pp. 1821-1832, 2012.
Song, P., et al., "Improved Shear Wave Motion Detection Using Pulse-Inversion Harmonic Imaging with a Phased Array Transducer", IEEE Transactions on Medical Imaging, vol. 32, issue 12, pp. 2299-2310, 2013.
Song, P., et al., Comb-push Ultrasound Shear Elastography (CUSE) with Various Ultrasound Push Beams, IEEE Transactions on Medical Imaging, vol. 32, issue 8, pp. 1435-1447, 2013.
Song, P., et al., "Fast Shear Compounding Using Robust 2-D Shear Wave Speed Calculation and Multi-directional Filtering", Ultrasound in Medicine and Biology, vol. 40, No. 6, pp. 1343-1355, 2014.
Song, P., et al., "Two-dimensional Shear Wave Elastography on Conventional Ultrasound Scanners with Time Aligned Sequential Tracking (TAST) and Comb-push Ultrasound Shear Elastography (Cuse)," IEEE Transactions on Ultrasonics, Ferroelectrics, and Frequency Control, vol. 62, issue 2, pp. 290-302, 2015.
Song, P., et al., "Quantitative Assessment of Left Ventricular Diastolic Stiffness Using Cardiac Shear Wave Elastography: A Pilot Study," Journal of Ultrasound in Medicine, vol. 35, pp. 1419-1427, 2016.
Song, P., et al., "Performance of 2-Dimensional Ultrasound Shear Wave Elastography in Liver Fibrosis Detection Using Magnetic Resonance Elastography as the Reference Standard: A Pilot Study," Journal of Ultrasound in Medicine, vol. 35, No. 2, pp. 401-412, 2016.
Song, P., et al., "Ultrasound Small Vessel Imaging with Block-wise Adaptive Local Clutter Filtering," IEEE Transactions on Medical Imaging, vol. 36, No. 1, pp. 251-262, 2017.
Song, P., et al., "Accelerated Singular Value-Based Ultrasound Blood Flow Clutter Filtering with Randomized Singular Value Decomposition (rSVD) and Randomized Spatial Downsampling," IEEE Transactions on Ultrasonics, Ferroelectrics, and Frequency Control, vol. 64, No. 4, pp. 706-716, 2017.
Song, P., et al., "Letters: Noise Equalization for Ultrafast Plane Wave Microvessel Imaging," IEEE Transactions on Ultrasonics, Ferroelectrics, and Frequency Control, vol. 64, issue 11, pp. 1776-1781, 2017.
Song, P., et al., "Quantitative Inflammation Assessment for Crohn's Disease Using Ultrasound Microvessel Imaging: A Pilot Study," Radiological Society of North America (RSNA) 2017, Chicago, IL, 2017.
Song, P., et al., "Functional Ultrasound Imaging of Spinal Cord Hemodynamic Responses to Electrical Stimulation: A Feasibility Study," Frontiers in Neurology, vol. 10, No. 279, pp. 1-13, 2019.
Stacker, S. A, et al. "Lymphangiogenesis and lymphatic vessel remodelling in cancer." Nature Reviews Cancer 14.3 (2014): 159.
Suh, C. H., et al. "The diagnostic performance of shear wave elastography for malignant cervical lymph nodes: A systematic review and meta-analysis." European radiology 27.1 (2017): 222-230.
Suzuki, K., Overview of deep learning in medical imaging. Radiol Phys Technol. Sep. 2017; 10(3):257-273. doi: 10.1007/s12194-017-0406-5. Epub Jul. 8, 2017. Review. PubMed PMID: 28689314.
Tadayyon, H., et al. Quantitative ultrasound assessment of breast tumor response to chemotherapy using a multi- parameter approach. Onoctarget, 7: 45094-45111, 2016.
Takahashi, R., et al., "Data Augmentation Using Random Image Cropping and Patching for Deep CNNs." IEEE Transactions on Circuits and Systems for Video Technology (2019): 1-1.
Tanaka, D., et al., Joint Optimization Framework for Leaming With Noisy Labels, The IEEE Conference on Computer Vision and Pattern Recognition (CVPR), 2018, pp. 5552-5560.
Tan, M. P., et al., "The 'twinkle' artifact - A novel method of clip identification to facilitate targeted axillary surgery following neoadjuvant chemotherapy in breast cancer patients," Clinical imaging., vol. 68, pp. 36-44, Dec 2020.
Tian, J., et al., et al. "Application of 3D and 2D quantitative shear wave elastography (SWE) to differentiate between benign and malignant breast masses." Scientific reports 7 (2017): 41216.
Tremblay, J., et al., The IEEE Conference on Computer Vision and Pattern Recognition (CVPR) Workshops, 2018, pp. 969-977.
Tsamardinos, I., et al., "Bootstrapping the out-of-sample predictions for efficient and accurate cross-validation." Machine learning 107. 12 (2018): 1895-1922.

* cited by examiner

500

RADIOLOGICAL CLIPS HAVING ULTRASOUND IDENTIFICATION

CROSS-REFERENCE TO RELATED APPLICATIONS

The present application claims the benefit of priority under 35 U.S.C. § 119 from U.S. Provisional Patent Application Ser. No. 63/299,778, entitled "Radiological Clips Having Ultrasound Identification," filed on Jan. 14, 2022, and U.S. Provisional Patent Application Ser. No. 63/309,348, entitled "Radiological Clips Having Ultrasound Identification," filed on Feb. 11, 2022, all of both of which is incorporated herein by reference in its entirety for all purposes.

STATEMENT OF FEDERALLY FUNDED RESEARCH OR SPONSORSHIP

This invention was made with government support under R21 EB030743 awarded by the National Institutes of Health. The United States Government has certain rights in the invention.

TECHNICAL FIELD

This disclosure relates generally to location identification markers for radiological imaging applications, and more specifically relates to radiological clips having ultrasound identification.

BACKGROUND

Radiological and imaging procedures are performed in medical practice to diagnose and treat a variety of medical conditions. Such diagnostic imaging procedures include computed tomography (CT) scans and magnetic resonance imaging (MRI). These diagnostic imaging procedures generally involve transmitting energy waves into a region of medical diagnostic interest in a patient's body, sensing the energy waves after exiting the patient's body, and computing an image based on the sensed energy waves. It may be difficult to accurately identify a position on the computed image in relation to the corresponding position in the patient's body from the computed image alone. Radiological clips may assist by providing identification indicia in the computed image corresponding to the respective radiological clips. In this way, a position of the identification indicia in the computed image may be correlated with the position of the corresponding radiological clip in the patient's body. Radiological markers or clips are an important tool for diagnostic imaging because their placement in a patient's body facilitates repeated identification of specific tissues over multiple imaging scans taken over an extended period of time, for example, days, weeks, or months.

The description provided in the background section should not be assumed to be prior art merely because it is mentioned in or associated with the background section. The background section may include information that describes one or more aspects of the subject technology.

SUMMARY

According to certain aspects of the present disclosure, a radiological clip device may be operable to locate tissue, marked by insertion of the device therein, within a diagnostic image of the marked tissue and surrounding tissue. The radiological clip device includes an ultrasound receiver configured to generate an electronic activation signal in response to receiving an ultrasound imaging pulse from an ultrasonic imaging array. The radiological clip device also includes an electronic driving circuit configured to generate an electronic identification signal responsive to the electronic activation signal. The radiological clip device further includes an ultrasound transmitter configured to transmit an ultrasound identification (USID) signal based on the electronic identification signal. The USID signal may include an encoded sequence associated with an identification protocol to uniquely identify the device within a diagnostic image. The USID signal may include one or more distinct encoded signals that each correspond to a different bit within a multiple-bit identification tag associated with an identification protocol to uniquely identify the device within a diagnostic image. The ultrasound transmitter may be configured to transmit the USID signal within a frequency bandwidth of one or more ultrasound imaging pulses that the ultrasound receiver is configured to receive from an ultrasonic imaging array. The ultrasound receiver may include a Schmitt trigger module configured to generate the electronic activation signal when the ultrasound imaging pulse is received from the ultrasonic imaging array and to refrain from generating the electronic activation signal when scattered ultrasound waves and/or reverb are received based on a threshold received pressure level. The electronic driving circuit may be configured to perform signal encoding based on a quantity of bits within a multiple-bit identification tag associated with an identification protocol of the USID to uniquely identify the device within a diagnostic image. The ultrasound transmitter may be configured to transmit the USID signal at a pressure level similar to a low pressure range associated with scattered ultrasound waves or reverb. The ultrasound receiver may include an electronic circuit coupled with a piezoelectric crystal that receives the ultrasound imaging pulse from the ultrasonic imaging array. The ultrasound receiver and the ultrasound transmitter may both be electronically coupled with a shared piezoelectric crystal via a switch controlled by a Schmitt trigger to receive the ultrasound imaging pulse from the ultrasonic imaging array at a first time, and responsive to the electronic driving circuit generating the electronic identification signal, transmit the USID signal at a second time.

According to certain aspects of the present disclosure, a method of transmitting an ultrasound identification (USID) signal by a radiological clip includes generating, by an ultrasound receiver circuit, an electronic activation signal responsive to receiving an ultrasound imaging pulse from an ultrasonic imaging array. The method also includes generating, by an electronic driving circuit, an electronic identification signal responsive to the electronic activation signal. The method further includes transmitting, by an ultrasound transmitter, a USID signal based on the electronic identification signal. Generating the electronic identification signal may include encoding a sequence of narrowband tone bursts associated with an identification protocol to uniquely identify the radiological clip within a diagnostic image or other encoded signal. Generating the electronic identification signal may include performing signal encoding based on a quantity of bits within a multiple-bit identification tag associated with an identification protocol to uniquely identify the device within a diagnostic image. Whether a signal is generated in a particular frequency band component of the USID signal may be based on a value of a corresponding bit within the multiple-bit identification tag. Transmitting the USID signal may include transmitting the USID signal within a frequency bandwidth of one or more ultrasound imaging pulses that the ultrasound receiver is configured to receive from an ultrasonic imaging array. Generating the electronic activation signal may include determining a received pressure level of an ultrasound signal and determining a threshold received pressure level to distinguish an ultrasound imaging pulse received from the ultrasonic imaging array having a pressure level above the threshold received pressure level from scattered ultrasound waves and/or reverb having a pressure level below the threshold received pressure level, as well as generating the electronic activation signal when the received pressure level is at or above the threshold received pressure level, and refraining from generating the electronic activation signal when the received pressure level is below the threshold received pressure level. Transmitting the USID signal may include transmitting the USID signal at a pressure level similar to a low pressure range associated with scattered ultrasound waves or reverb.

According to certain aspects of the present disclosure, an ultrasound imaging system includes a radiological clip device locating tissue within a subject, marked by insertion of the device therein, within a diagnostic image of the marked tissue and surrounding tissue, as well as an ultrasound imaging apparatus. The radiological clip device includes an ultrasound receiver configured to generate an electronic activation signal in response to receiving an ultrasound imaging pulse from the ultrasonic imaging apparatus. The radiological clip device also includes an electronic driving circuit configured to generate an electronic identification signal responsive to the electronic activation signal, and an ultrasound transmitter configured to transmit an ultrasound identification (USID) signal based on the electronic identification signal. The ultrasound imaging apparatus includes an ultrasound transducer array, one or more hardware computing processors configured to execute computing instructions, and a non-transitory computer readable medium having stored therein executable instructions which, when executed by the one or more hardware processors, cause performance of operations for a method of diagnostic imaging. The method of diagnostic imaging includes causing the ultrasound transducer array to transmit a plurality of transmitted ultrasound imaging pulses toward the subject, processing electronic signals received from the ultrasound transducer array corresponding to a plurality of returned ultrasound imaging pulses from the subject, and generating an ultrasound image of the subject based on the plurality of transmitted ultrasound imaging pulses and returned ultrasound imaging pulses. The method also includes detecting the radiological clip device by processing electronic signals received from the ultrasound transducer array corresponding to the USID signal from the radiological clip device within the subject and within a same imaging field as the returned ultrasound imaging pulses. The method further includes determining a location of the radiological clip device within the imaging field of the subject, determining an ID number corresponding to the radiological clip device based on the USID signal received from the radiological clip device, and displaying the ultrasound image of the subject together with an indication of the location of the radiological clip device within the ultrasound image of the subject. The displaying also includes displaying the ID number associated with the radiological clip device. The displaying is performed on a display. Determining the location of the radiological clip device within the imaging field of the subject may include employing a pulse-inversion ultrasound to isolate the received USID signal from the plurality of returned ultrasound imaging pulses received from the subject. Determining the location of the radiological clip device may include identifying a lateral location of the radiological clip device based on one or more particular imaging scan lines in which the USID signal is detected, and estimating an axial location of the radiological clip device based on a time sample at which the USID signal is first detected within the imaging field. Determining the ID number corresponding to the radiological clip device may include calculating a frequency spectrum of the USID signal, correlating a phase-encoded sequence to the USID signal, determining whether a frequency component of the USID signal is present at each of a plurality of frequency bands corresponding to bits within a multiple-bit identification tag associated with an identification protocol of the USID, determining a value of each bit within the multiple-bit identification tag based on the determination of a presence of a frequency component of the USID signal at the corresponding frequency band, and determining the ID number based on the determined values of each bit within the multiple-bit identification tag.

It is understood that other configurations of the subject technology will become readily apparent to those skilled in the art from the following detailed description, wherein various configurations of the subject technology are shown and described by way of illustration. As will be realized, the subject technology is capable of other and different configurations and its several details are capable of modification in various other respects, all without departing from the scope of the subject technology. Accordingly, the drawings and detailed description are to be regarded as illustrative in nature and not as restrictive.

BRIEF DESCRIPTION OF DRAWINGS

The disclosure is better understood with reference to the following drawings and description. The elements in the figures are not necessarily to scale, emphasis instead being placed upon illustrating the principles of the disclosure. Moreover, in the figures, like-referenced numerals may designate corresponding parts throughout the different views.

Figure 1:
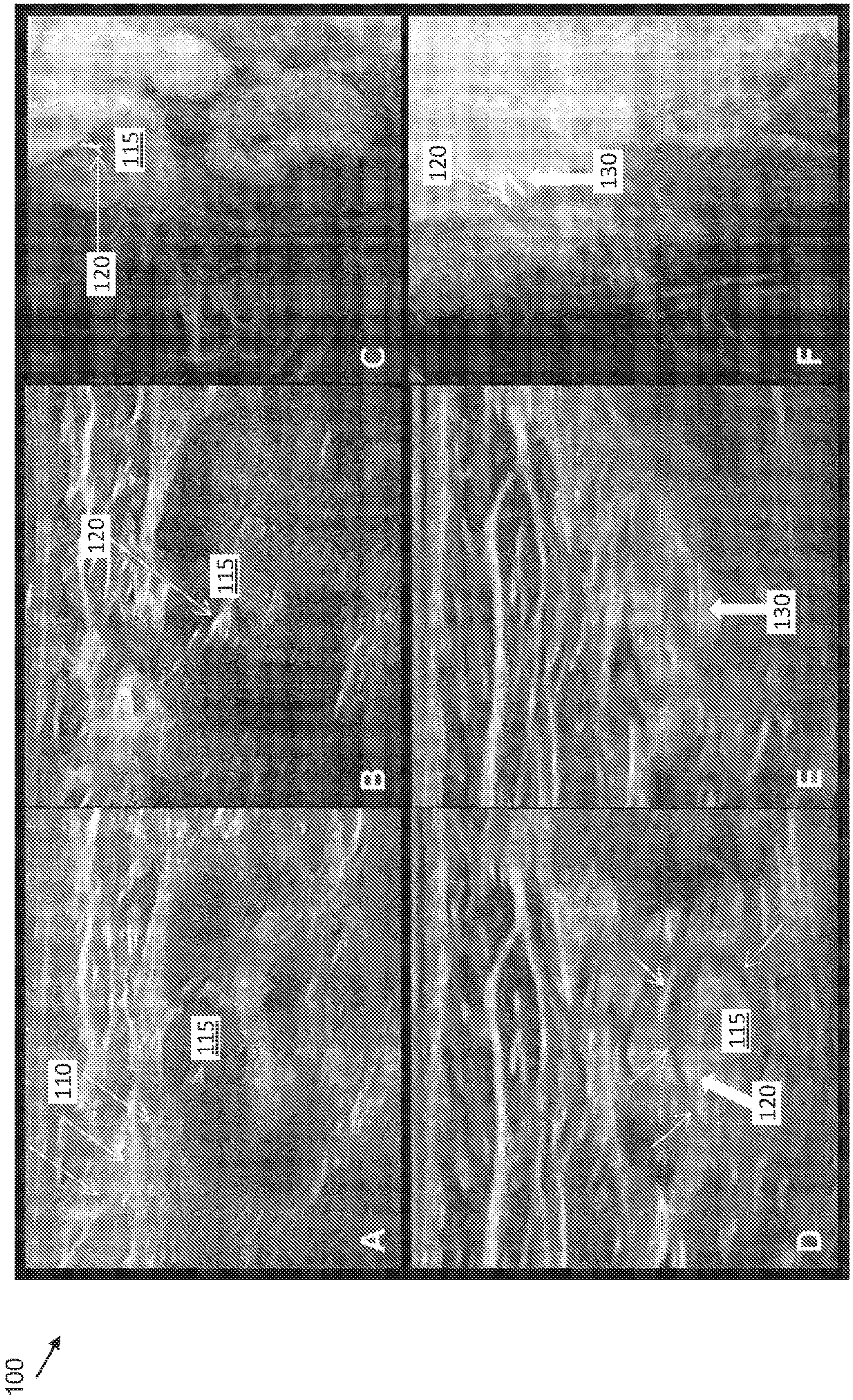
FIG. 1A is an exemplary ultrasound image showing a shaft of a small-gauge needle 110 being inserted into the cortex of an axillary lymph node (ALN) 115 during ultrasound-guided fine-needle aspiration.
FIG. 1B is an exemplary ultrasound image showing a clip 120 that has been inserted into the ALN 115 that has been determined to be positive for malignancy via an invasive needle-guided procedure in order to mark the ALN 115.
FIG. 1C is an exemplary mammogram image confirming presence of the previously inserted clip 120 in the ALN 115.
FIG. 1D is an exemplary image showing that the positive ALN 115 has been normalized in appearance after neoadjuvant chemotherapy (NAC) and the clip 120 is barely conspicuous.
FIG. 1E is an exemplary image showing preoperative I-125 seed localization being performed using a seed 130.
FIG. 1F is an exemplary post-localization mammogram image confirming that the seed 130 is in close proximity to the clip 120.

In one or more implementations, not all of the depicted components in each figure may be required, and one or more implementations may include additional components not shown in a figure. Variations in the arrangement and type of the components may be made without departing from the scope of the subject disclosure. Additional components, different components, or fewer components may be utilized within the scope of the subject disclosure.

DETAILED DESCRIPTION

The detailed description set forth below is intended as a description of various implementations and is not intended to represent the only implementations in which the subject technology may be practiced. As those skilled in the art would realize, the described implementations may be modified in various different ways, all without departing from the scope of the present disclosure. Accordingly, the drawings and description are to be regarded as illustrative in nature and not restrictive.

Breast cancer is among the most common cancers diagnosed in the United States, with an estimated 284,200 new cases in 2021. Cases were overwhelmingly in women, but accounted for 15% of all new cancer diagnoses [Siegel21]. When a patient is diagnosed with breast cancer, doctors have a wide array of options for treatment based on the severity and stage of the disease. Treatment usually includes a combination of chemotherapy, radiation, and surgery to remove lesions or inhibit the cancer's ability to spread. One such treatment option, neoadjuvant chemotherapy (NAC), may be performed as an initial measure in cases where other treatments such as surgery are the focus of a treatment plan. NAC is a valuable treatment option in order to both facilitate breast-conserving surgery and treat cancerous lymph nodes. NAC is commonly employed as a precursor to breast conserving therapies, where it can lessen the size of tumors to improve outcomes. Patients who have been staged with node-positive breast cancer may undergo NAC to curb metastasis outside the lymph nodes in the breast. In both cases, NAC has proven effective, with a 40-75% rate of complete pathological response in node-positive cases [Nguyen et al., 2017]. However, NAC can be a several-month process during which tissue has time to change in appearance, particularly in response to treatment. Cases of complete pathological response may occur when NAC is highly effective at treating the cancerous areas; in lymph nodes, for example, this typically means a return to a non-inflamed and healthy appearance when imaged using a modality such as ultrasound. This leads to areas that may not be visually distinct without some external guidance. As such, the use of NAC implicates the insertion of some visible marking clip to enable accurate localization.

Diagnostic ultrasound imaging may be used to stage tumor size, to identify possible lymph nodes for metastases, to guide biopsy of tumors, lesions, and lymph nodes, and to monitor the size and appearance of tumors as well as their changes over a period of time. Several months may pass between the initial identification of a tumor and positive lymph nodes, chemotherapy application and surgery. In the case of excellent treatment response to NAC, the treated positive lymph nodes may normalize in imaging appearance, making the previously identified positive node no longer readily identifiable. Similarly, tumors and lesions may change in shape, size, and appearance during the course of treatment, making the task of identifying them more difficult at the time of surgery. Tumors, lesions, and suspicious lymph nodes are typically marked with the insertion of radiological clips before NAC treatment, so that they may be able to be re-identified before surgery. Clearly marking the positive nodes from the onset, prior to NAC, may significantly aid re-identification of benign and cancerous lesions prior to surgery. This may be accomplished by ultrasound-guided percutaneous placement of biopsy markers or clips into the positive node(s) and identified breast lesion(s). The insertion of the radiological clips is motivated by the expected changes in or normalization of appearance of the tumors and lymph nodes over the course of NAC treatment. However, conventional approaches to clip design are insufficient for ultrasound localization after months spent in vivo, resulting in inefficient, awkward, and uncomfortable ancillary localization setups to compensate. For example, factors such as tissue buildup around the clip site and inherent changes due to tissue response to NAC may result in complications whenever attempts are being made to image clips pre-surgery. Where ultrasound fails, secondary methods of imaging may be leveraged, but switching to a secondary system is inefficient and may lead to cumbersome imaging setups and even patient discomfort. Additionally, where there may be multiple sites of interest or a particularly large region to bracket, multiple clips of different designs may be used. However, much of the resolution which aids in distinguishing clip designs in other radiological imaging modalities is not present in ultrasound, so identifying individual prior technology clips is even more difficult. The inability to correctly identify a clip in an image provides ambiguity to the surgeon when resecting tissue like a positive lymph node or tumors and lesions in a patient's breast after NAC.

In recent years, various clips have been designed and manufactured with the goal of providing better image contrast and identification of marked tissues under real-time imaging with modalities such as ultrasound, as well as minimal migration of the clips. Ultrasound imaging may be beneficial in these applications due to its safety, real-time imaging capabilities, portability, and convenience of bedside use. Early expectations were that simple clip designs made from metal would provide sufficiently high contrast for ultrasound imaging to facilitate straightforward locating of the clips in B-mode ultrasound. However, in practice, it has been found that identification of radiological clips such as these may be difficult due to multiple bright scatterers in the imaging field that may appear similar to the signal from a clip, or due to the clip signal being too low in intensity because of the relative orientation of the clip with respect to the imaging probe. To address this, new clips have been developed over time to have a variety of shapes and sizes, different surface textures, and compound material properties. Although manufacturers have asserted that these clip designs solve the problem of visualization on ultrasound B-mode and facilitate identification of different tissues, these claims of solving the problem of visualization have not been realized in practice. The problem of proper visualization is still significant and these clips may still not be identifiable, especially in follow-on imaging studies after initial clip placement.

Described herein is a new type of radiological clip with improved visualization and localization by ultrasonic imaging that may also be used to identify the specific clip in the patient's imaged tissue via unique ID tags. The novel radiological clip may include a small biocompatible ultrasonic source and driving circuit that is operable to detect an ultrasonic imaging pulse. In response to the detection of the ultrasonic imaging pulse, the novel clip may In an example, the novel clip may emit narrowband tone bursts associated with a specific identification protocol. For example, the ultrasonic imaging pulse may trigger the driving circuit, which may include several small oscillators, to drive the ultrasonic source to emit a specific encoded ultrasonic signal. The encoded ultrasonic signal may include one or more narrowband signals that together provide a unique identification code to facilitate the clip being clearly visualized and localized with specificity via ultrasound imaging, and also to identify the specific clip, e.g., via ultrasound identification (USID). Each of the one or more narrowband signals may correspond to a single bit in a multiple-bit ID tag.

In an example, the novel clip may perform phase modulation encoding of carrier frequencies in association with a specific identification protocol. For example, the ultrasonic imaging pulse may trigger the driving circuit, which may include electronic circuits (e.g., implemented in an application-specific integrated circuit (ASIC) that perform the phase modulation of one or more carrier frequencies, to drive the ultrasonic source to emit a specific encoded ultrasonic signal. The encoded ultrasonic signal may include one or more ID signals encoded with phase modulation that together provide a unique identification code to facilitate the clip being clearly visualized and localized with specificity via ultrasound imaging, and also to identify the specific clip, e.g., via ultrasound identification (USID). Each of the one or more phase modulation encoded signals may correspond to a single bit in a multiple-bit ID tag. The ASIC may perform digital signal processing to encode a signal with a USID number through phase modulation.

The new radiological clip's visibility does not depend on the echogenicity of the clip, but rather on the unique clip signal that is emitted and processed. The new radiological clip may disrupt the marketplace by replacing currently available radiological clips used in breast cancer therapy and potentially other cancer therapies, including prostate cancer.

The novel radiological clip described herein may have much higher visibility on ultrasound imaging compared to prior commercially available clips and may also provide ultrasound identification (USID) so that multiple breast lesions may be tagged and distinguished from each other during surgical resection. Unlike prior commercial radiological clips, the visibility of the novel radiological clips described herein may not depend on the echogenicity of the clip, but rather on the unique signal emitted from the clip. In practice, a physician may place multiple instances of the novel clips having different unique IDs in multiple different tumors, lesions or lymph nodes and come back later in time, e.g., after NAC and prior to surgery, to locate and identify specific tissue targets. For example, lymph nodes could be specifically labeled at the time of placement of the novel clips and still be identified even after their appearance changes months down the road.

Significance:

Breast cancer is the most common malignancy and also the leading cause of cancer death in women worldwide [Wcr19]. According to data from the Surveillance, Epidemiology, and End Results Program at the National Institutes of Health, there were approximately 276,480 new cases of female breast cancer in the United States in 2020, and about 42,170 people died of this disease [Can21].

Treatment of patients having breast cancer typically includes the selective application of neoadjuvant chemotherapy (NAC) followed by breast-conserving surgery on shrunken tumors [Nur05, Gen16, Sak18b]. Precise identification and localization of multiple breast lesion(s) may help optimize surgical outcomes [Kim13]. NAC may result in changes in the size and shape of the cancerous tumor(s) and lesions, including a complete response. Thus, marker clips are routinely placed in the tumors and lesions at the time of biopsy to facilitate identification of the original tumors' and legions' sites post-NAC, facilitating radiologic guidance and surgical excision [Bur97, Sha18]. The placement of these markers may help prevent re-biopsy of benign lesions, distinguish multiple biopsied lesions from one another, facilitate correlation of image findings from multiple modalities, guide pre-operative localization, and confirm surgical target removal [Sha18].

In addition to breast lesions, axillary lymph nodes (ALNs, a subset of lymph nodes (LNs)) are involved in approximately 30-40% of newly diagnosed breast cancers in women. Previously, identification of metastatic ALNs in patients with breast cancer was determined through complete ALN dissection (ALND). Unfortunately, ALND can result in significant complications and morbidities including wound infection, lymphedema, paresthesia and decreased range of motion [Ash10, Luc07]. Given this, sentinel lymph node biopsy (SLNB) may first be used to determine whether to perform ALND [Alv06] and has largely replaced ALND as a staging and prognostic modality in patients who are clinically node negative [Ozc17]. More recently, ALND may even be avoided in select patients who are found to be lymph node positive. The American College of Surgeons Oncology Group (ACOSOG) Z0011 found equivalent outcomes for SLNB alone compared to completion ALND for women with one (1) to two (2) positive sentinel lymph nodes (LNs) undergoing breast-conserving surgery, whole-breast radiotherapy, and systemic therapy [Giu10, Giu11, Pil16].

FIG. 1A is an exemplary ultrasound image showing a shaft of a small-gauge needle 110 being inserted into the cortex of an axillary lymph node (ALN) 115 during ultrasound-guided fine-needle aspiration. When ultrasound evaluation identifies suspicious ALNs (e.g., ALN 115), the most worrisome LN undergoes ultrasound-guided fine-needle aspiration, where a small-gauge needle (e.g., 110) is inserted into the cortex of the lymph node (see A, where arrows point to the shaft of needle 110).

FIG. 1B is an exemplary ultrasound image showing a clip 120 that has been inserted into the ALN 115 that has been determined to be positive for malignancy via an invasive needle-guided procedure in order to mark the positive ALN 115. When the ALN 115 is tested to be positive for malignancy, it is marked with a clip 120 (see B, arrow), another invasive needle-guided procedure.

FIG. 1C is an exemplary mammogram image confirming presence of the previously inserted clip 120 in the ALN 115. Mammogram confirms placement of the marker clip 120 in the axilla (see C, arrow). Following this confirmation, NAC is performed on the patient.

FIG. 1D is an exemplary image showing that the positive ALN 115 has been normalized in appearance after NAC (see D, thin white arrows) and the clip 120 is barely conspicuous (see D, thick white arrow).

FIG. 1E is an exemplary image showing preoperative I-125 seed localization being performed using a seed 130 (see E, thick arrow).

FIG. 1F is an exemplary post-localization mammogram image confirming that the seed 130 (see F, thick arrow) is in close proximity to the clip 120 (see F, thin arrow).

Breast cancer staging often includes targeted ultrasound of the ALNs with an ultrasound-guided fine-needle aspiration or biopsy of the most suspicious ALN when one or more suspicious ALNs are present. If pathology of a biopsied suspicious LN is positive for malignancy, the patient joins the population of patients with node-positive disease (according to TNM staging [Bri16]). In patients undergoing NAC who have an excellent radiographic response, a SLNB may be selectively performed to determine if the previously positive malignancy of the LN has converted to negative pathologically. The elapsed time between determination of the positive LN and SLNB is usually several months. In the setting of excellent treatment response, the treated positive LN normalizes in imaging appearance, making the previously identified positive LN no longer readily identifiable on its own. Ensuring that the previously positive identified LN is removed is important for assuring the lowest possible false negative rate (e.g., where negative SLN and positive non-SLNs left in the axilla) [Bou13, Bou16, Cau16]. This reduction in false negative rates involves two invasive procedures: marker or clip placement at time of the biopsy, and a percutaneous localization of a marker that may be identified intraoperatively. The marker or clip placement is typically accomplished by ultrasound-guided percutaneous placement of a biopsy clip 120 into the positive LN (e.g., ALN 115 shown in FIGS. 1B-1C). Therefore, use of radiological clips (e.g., clip 120) has become standard practice in the treatment of breast cancer and a vital part of overall patient management.

Over the passage of time, the visibility of the clip 120 in ultrasound imaging can become less clear, as shown in the ultrasound B-mode image of FIG. 1D. While FIGS. 1D-1F show a case of positive clip identification using ultrasound after NAC, it should be noted that there is little to differentiate the clip 120 (shown as a bright spot in FIG. 1D) from other bright targets or scatterers in the image. As has been noted in the literature, in many cases the orientation of the marker clip with respect to the imaging array of the diagnostic imaging equipment results in low echogenicity and a clip signal that is not distinguishable from the tissue background [Bou14, Ngu17, Tan20]. The inability to specifically identify the clip 120 in ultrasound B-mode images makes targeting of the LNs for resection after NAC very difficult and localization procedures are suboptimal [Hyd19]. This is a significant handicap, at least because when the clip 120 cannot be sonographically identified in the LN post NAC, tomosynthesis localization or CT guidance may be required. Tomosynthesis localization of LNs is very uncomfortable for the patient, awkward for the radiologist, and time consuming (personal communication JWJ Mayo Clinic) [Cho19]. Therefore, a novel radiological clip as described herein that has better and consistent visibility is highly medically significant for surgical resection of positive, clipped LNs.

To meet these important medical needs described above, we describe herein a novel radiological clip that may have much higher visibility on ultrasound images compared to prior (e.g., commercially available) clips and may also provide ultrasound identification (USID) features to facilitate multiple breast lesions being tagged and distinguished from each other during surgical resection. In contrast to prior radiological clips, the visibility of the novel radiological clips described herein do not depend on the echogenicity of the clip but is rather enhanced by a unique signal emitted from the clip. The unique signal may also provide a unique identifier number for a specific clip to facilitate specific marking of different breast lesions.

In the past few years, radiologists at Mayo Clinic (in Rochester, MN), for example, have used up to twelve (12) different styles of commercially available radiological clips to specifically identify different breast lesions. Even with using these different styles, it has been found to still be difficult to identify different lesions based on their ultrasound appearance, where the clip may appear as a bright blob regardless of the style of clip. Furthermore, because of their changes in appearance after NAC, it may not be possible to differentiate different masses and identify a specific mass after NAC that had been previously identified prior to NAC without using markers that provide unique identification features.

In contrast to prior marker clip technologies, the novel radiological clips described herein may offer better visibility and the distinct identification of the specific clip and corresponding lesion using ultrasound imaging. A prior marker clip technology based on a twinkle artifact, a phenomenon in Doppler imaging in which Doppler imaging pulses scatter randomly across a rough surface, may give a bright shimmering effect in color flow imaging as the "speed" of the stationary clip appears to randomly change. The ULTRA- COR® TWIRL™ (Bard, Inc.) clip generates the twinkle artifact due to its characteristic rough surface, and the artifact may appear a few millimeters below the clip in the image. The twinkle artifact effect may be enhanced by adjusting system settings [Tan et al., 2020 12], but this clip technology does not address distinguishing individual clips from one another. Other radiological clip technologies (e.g., the Faxitron LOCalizer™ from Hologic, Inc.) may use a radio frequency identification (RFID) technology to identify specific breast lesions up to a depth of 60 mm. This other technology requires an additional proprietary probe to detect the RFID signal that is separate from the ultrasound probe and often still requires ultrasound guidance [Mal19]. However, these clips are only cleared to be placed in a patient's body for a maximum of 30 days before removal [Malter et al., 2019]. Another radiological clip technology (e.g., the SAVI Scout from Cianna Medical) includes a small clip having an electrical circuit that when activated may be detected through a nonradioactive radar signal [Man16]. The active circuit included in this other radiological clip does not provide ID capabilities. The exemplary LOCalizer and SAVI Scout technologies provide information regarding the distance between the probe and the clip in millimeters, but do not provide anatomical context like sonography may provide. This is an example of the significant and ongoing handicaps that these prior clip technologies have. The novel radiological clip technology described herein provides beneficial capabilities not provided by prior existing technologies, for example, clip USID and clear visualization and localization of the clip under ultrasound imaging.

Innovation

Figure 2:
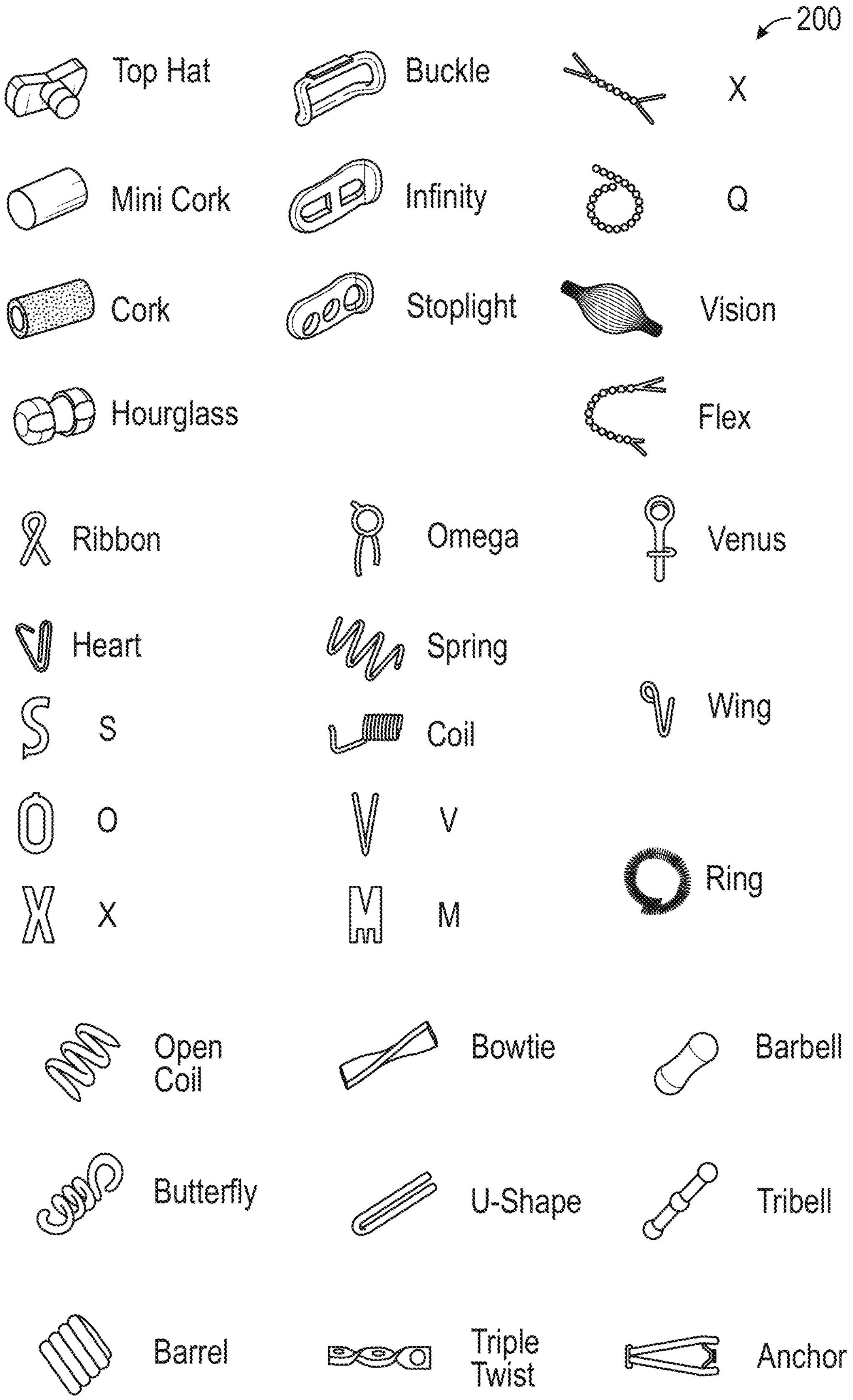
FIG. 2 is an exemplary image showing prior technology radiological clips having a variety of shapes, configurations and sizes.
Figure 3A:
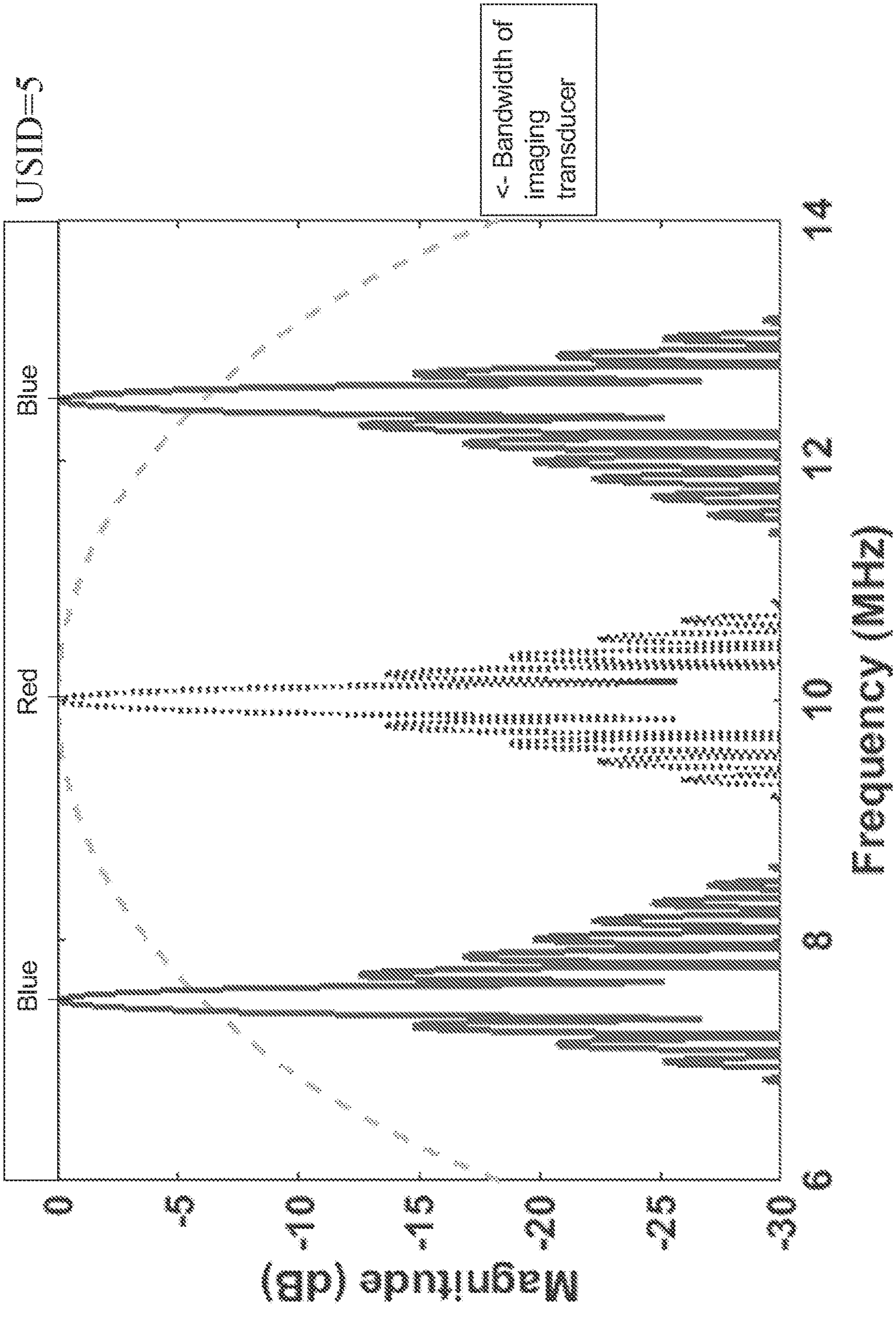
FIGS. 3A, 3B, 3C, and 3D are exemplary frequency spectra graphs that show the frequency spectra associated with different ID configurations supported by three (3) separate binary narrowband signals.
Figure 3B:
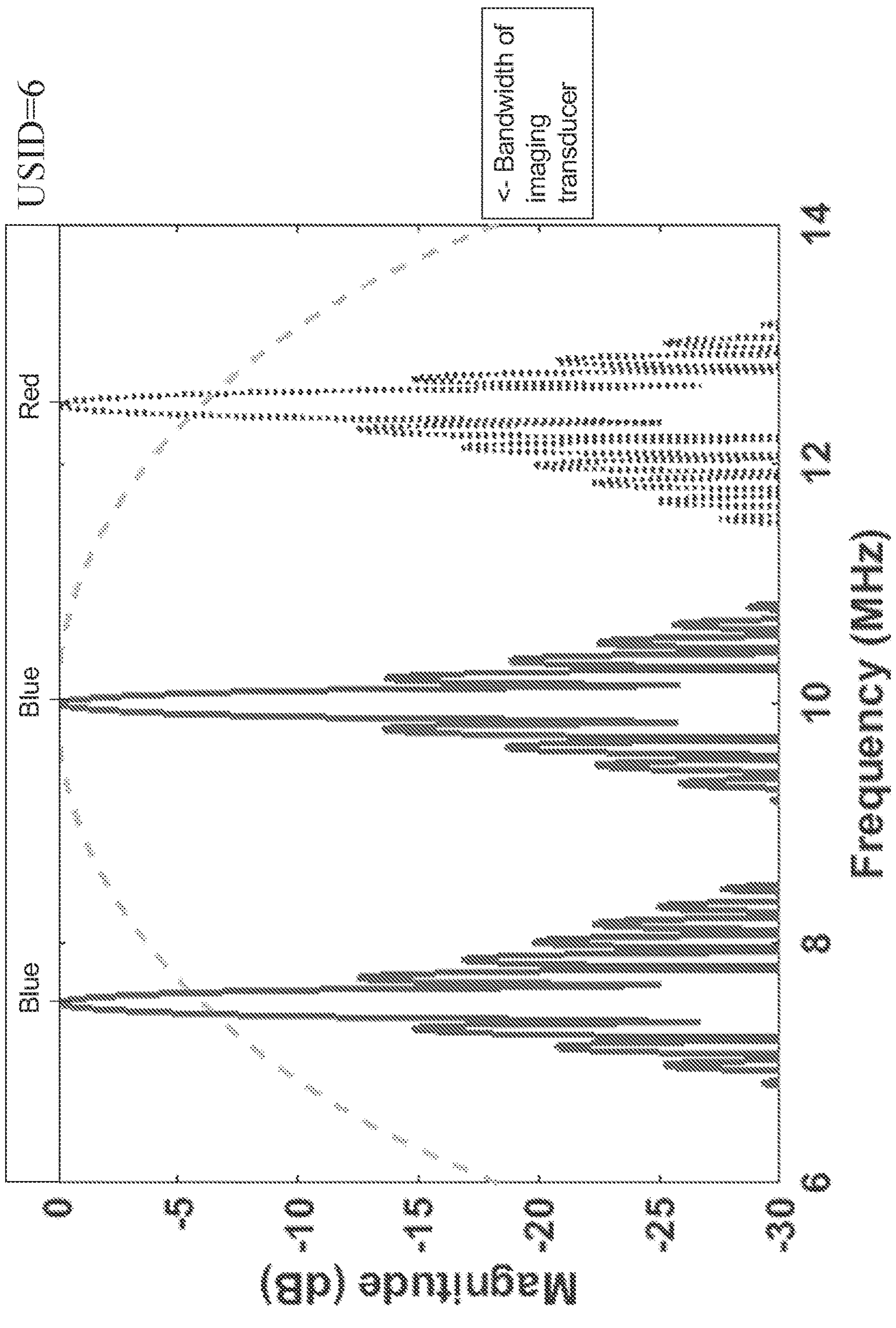
Figure 3C:
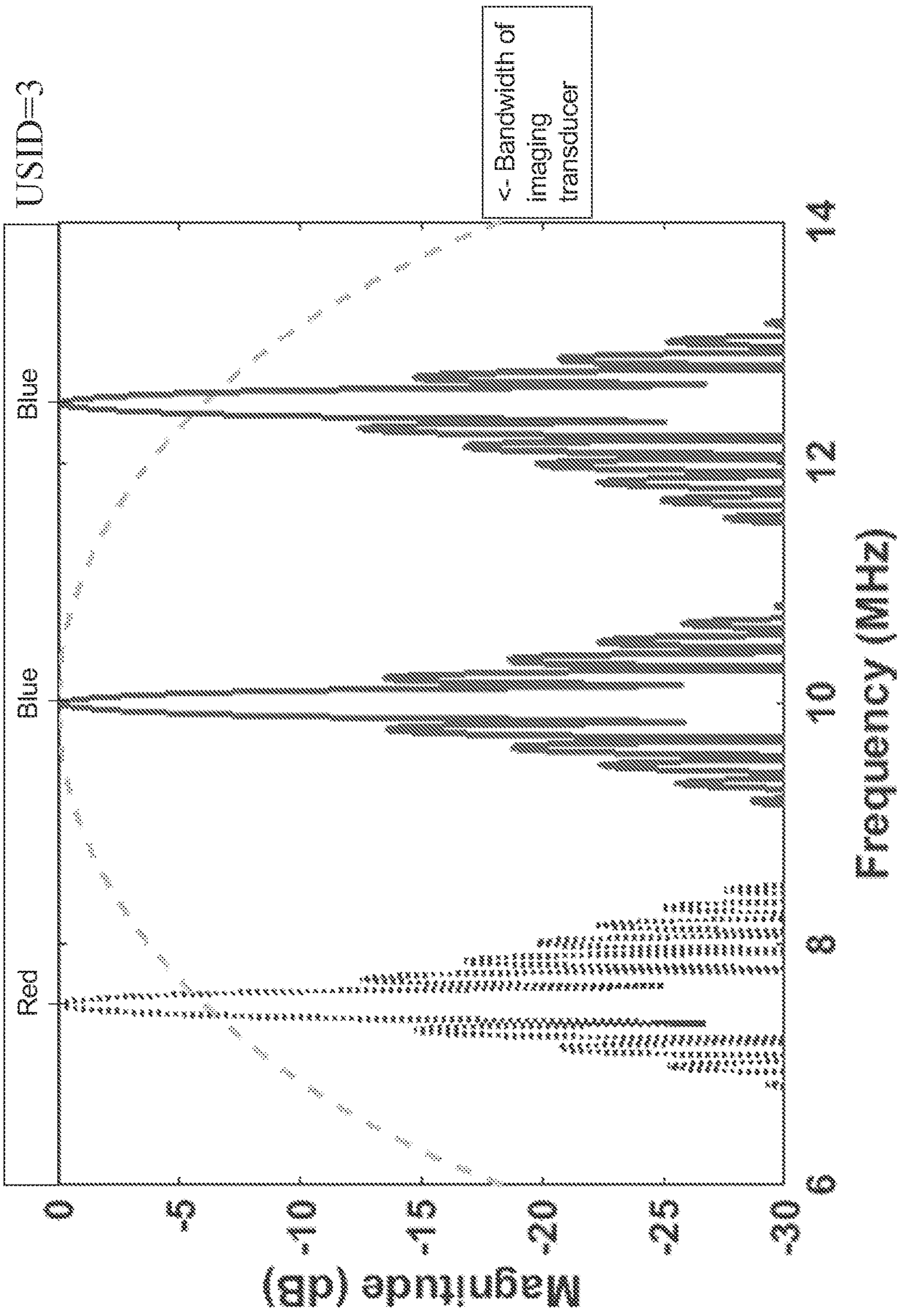
Figure 3D:
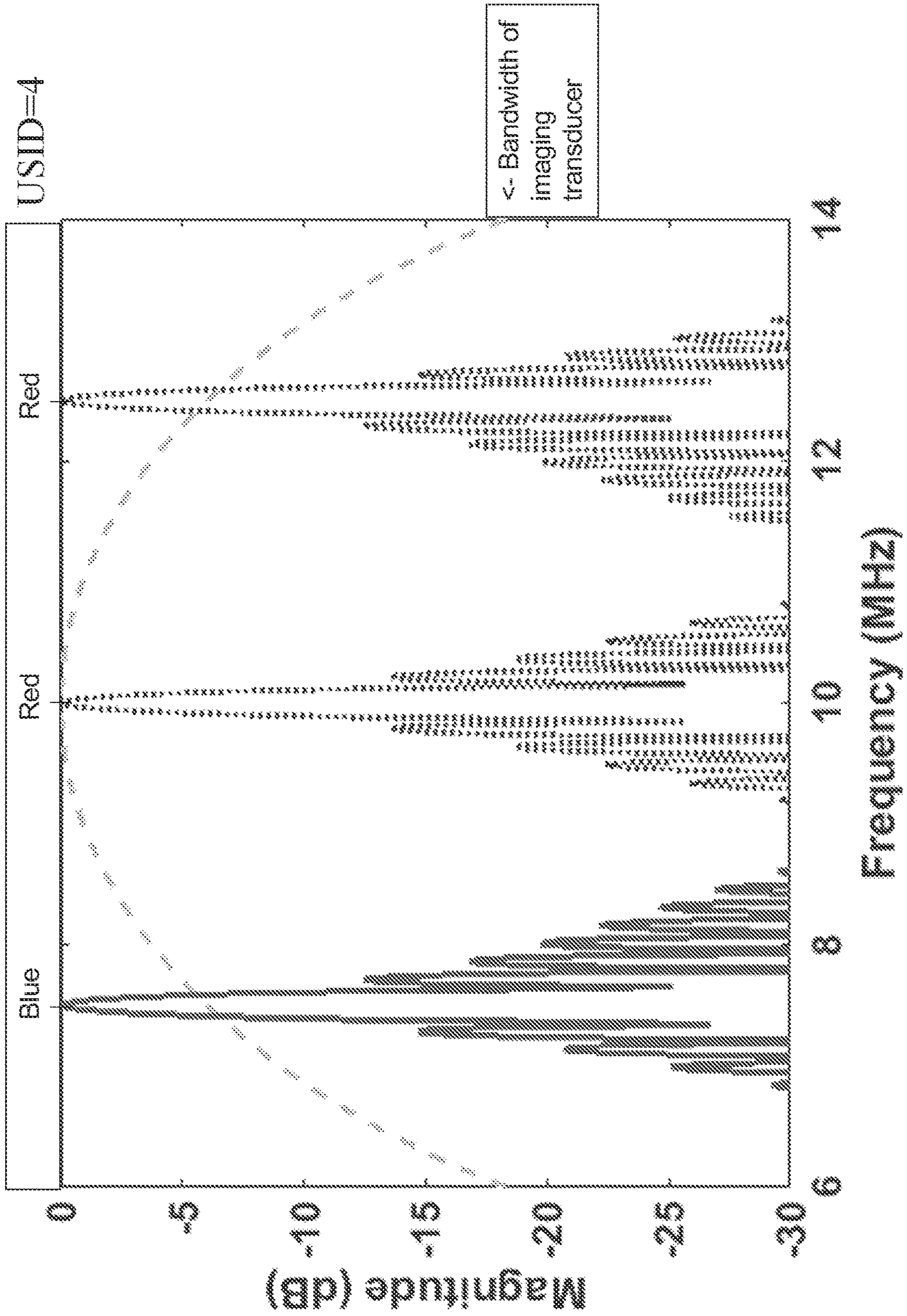

FIG. 2 is an exemplary image showing prior technology radiological clips having a variety of shapes, configurations and sizes [Por19]. Over the past decades, a multitude of radiological clips have been developed in an effort to provide superior visibility during imaging and to reduce migration. In 2019, for example, 38 different radiological clips were commercially available. The intent of the prior technology radiological clips has been to be visible to X-ray. As the clinical practice has evolved more recently, being able to identify the clips on ultrasound images is also important. The material and shape of the clips provides an impedance contrast for ultrasound that is much higher than surrounding soft tissue. As a result, the clips may provide a bright target for ultrasound. However, as noted earlier, the orientation of the clip relative to the ultrasound probe may reduce clip image intensity relative to surrounding tissue. Furthermore, many structures in human soft tissue may also give rise to bright scatterers in ultrasound B-mode, which may reduce the ability to pinpoint a specific clip in the image (e.g., see FIG. 1D).

Herein we describe novel radiological clips that may be visible to both ultrasound and X-ray, be compatible with MRI applications, and also provide a unique identification signature for ultrasound imaging resulting in target specificity, i.e., USID. The novel clip described herein may interact with an ultrasonic imaging pulse used for B-mode imaging and emit an ultrasonic signal in the bandwidth of the imaging probe, thereby providing USID of the clip. Novel imaging software may superimpose the identity of the USID clip, e.g., a number associated with the clip, on the B-mode image providing a real time identification of the clip in the anatomical context. Clips may be associated with specific tumor sites and specific lymph nodes for better targeting and resection and for improved patient follow up. The novel clips described herein may be compatible with currently available clinical ultrasound machines used for breast imaging. Novel electronic circuitry for demonstrating stand-alone clips in tissue-mimicking phantoms and tissue samples in vivo are also described.

Approach

A novel USID radiological clip and software as described herein may be used, for example, in clinical settings, in conjunction with one another to detect clip signals within imaged tissue and display their ID on a B-mode image of the imaged tissue.

A radiological clip circuit integrated with the clip may be triggered by an incoming imaging pulse from an ultrasonic imaging array. Once triggered, the clip circuit may cause the clip to emit a signal that is unique to the clip identification (e.g., similar to commercial RFID tags except with ultrasound instead of radio frequency electromagnetic waves). The emitted signal may have its identification encoded through a binary scheme supporting various ranges of ID numbers, for example, 1 through 7, 1 through 15, 1 through 31, or other ranges of numbers. As an example, if the imaging pulse is broadband and centered around 10 MHz for breast imaging, the clip may emit one (1), two (2), or three (3) narrowband signals that are within the bandwidth of the imaging array to represent an ID number from 1 through 7. Specifically, one, two, or three narrowband tone bursts may be summed and transmitted by a small transducer that is part of the clip to represent an ID number from 1 through 7. Emission of as many as four (4) narrowband signals may represent an ID number up through 15, while emission of as many as five (5) narrowband signals may represent an ID number up through 31.

FIGS. 3A, 3B, 3C, and 3D are exemplary frequency spectra graphs that show the frequency spectra transmitted by the USID clips described herein that are associated with different ID configurations supported by up to three (3) separate binary narrowband signals. The ID provided by the narrowband signals of FIGS. 3A-3D may be a binary number comprising three (3) bits that may be either on or off. If all the bits are on, the represented ID may be decimal number 7, e.g., [1 1 1]. If the clip emits the narrowband signals associated with bits 1 and 3, i.e., [1 0 1], the corresponding represented ID may be decimal number 5 (see FIG. 3B). Dotted lines labeled "Red" represent 'off' or '0' bits, solid lines labeled "Blue" represent 'on' or '1' bits, and dashed overarching lines labeled "Bandwidth" represent the bandwidth of the imaging transducer.

Figure 4:
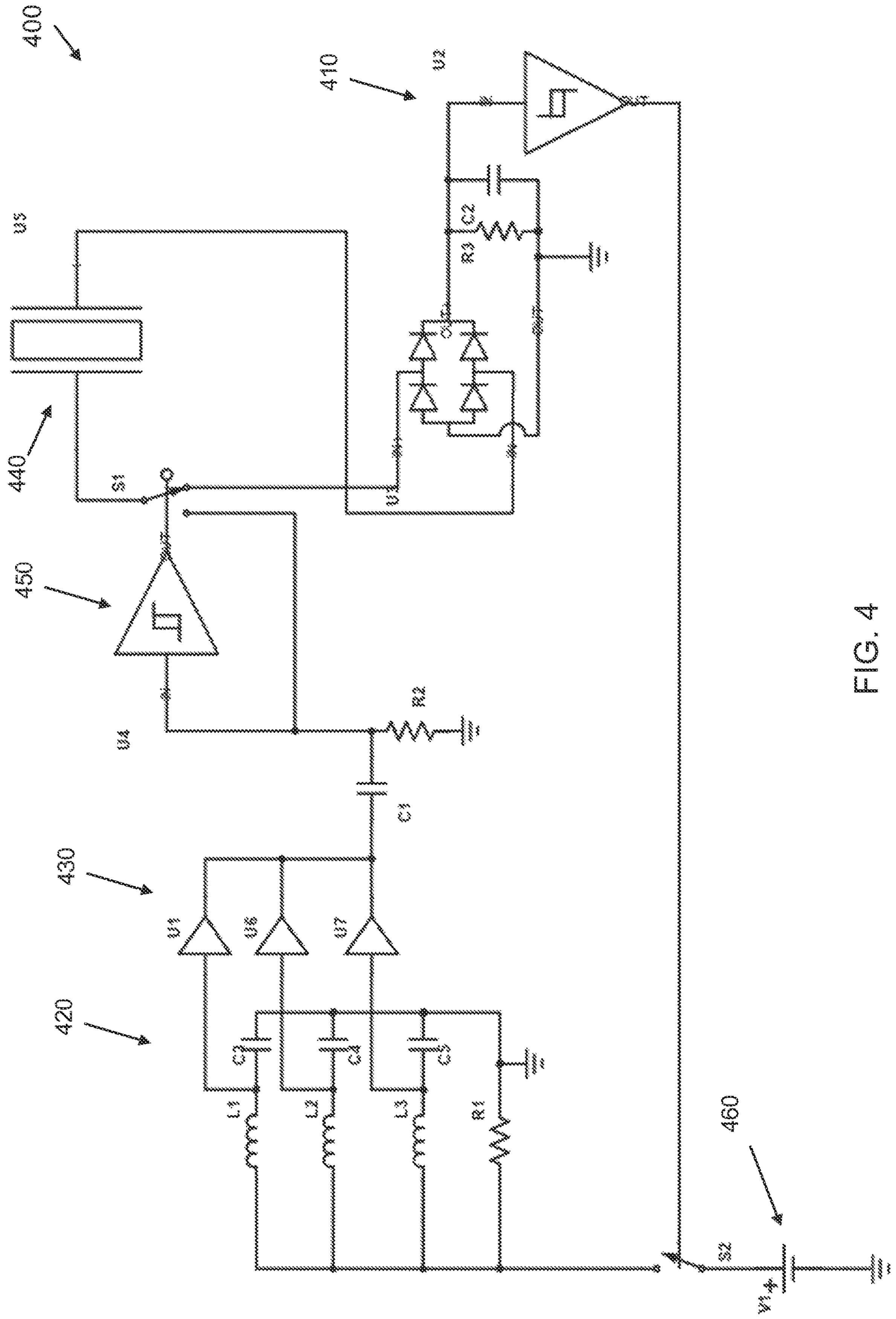
FIG. 4 is an exemplary schematic diagram of an electronic circuit for the novel ultrasound identification (USID) clip described herein.

FIG. 4 is an exemplary schematic diagram of an electronic circuit 400 for the novel USID clip described herein. The electronic circuit 400 may comprise three circuit modules. A Schmitt trigger module 410 may detect when an imaging ultrasonic pulse is incident on the clip, or more specifically, a transducer attached to the clip. The imaging pulse may be a broadband pulse (e.g., >66% fractional bandwidth) coming from an ultrasonic array attached to a scanner in order to provide good ultrasonic imaging. These bandwidths are typical of clinical imaging systems and modern imaging arrays. However, the imaging pulse may have pressure values up to a few MPa. The Schmitt trigger may have a threshold set to be activated only from incoming imaging pulses and not from scattered waves or reverb present in the field, which may be expected to have pressure levels much smaller than the incident imaging pulse levels (e.g., tens (10s) of dB smaller). In an in vivo setting, a clip may be placed at depths up to 6 cm and imaging pulses incident on the clip transducer may have varying pressure levels. Therefore, the threshold may be set so that the Schmitt trigger is activated by a range of values while not being activated by small signals coming from scattering or reverb. A range of output levels from an imaging source may be explored to tabulate threshold differences between incident imaging pulses and signals scattered from tissue structures in order to determine an optimal value to set as the trigger threshold in an application. An exemplary design instance may include a specific minimum power level from the ultrasonic scanning system, and may be considered as a part of the operational mode of the scanner for clip imaging.

In an example, the trigger from the imaging pulse may result in the excitation of up to three (3) LC oscillators in an oscillator module 420 that are tuned to specific frequencies and tuned to have high Q values between about 20 and 60, for example, 40-50, or greater, representing output tone bursts on the order of more than 20 cycles. In a transducer module 440, the output signal from the oscillators in the oscillator module 420 may be isolated via buffers 430 before being summed, and the summed signal may be used to re-excite the clip transducer module 440 for transmission back to the imaging source. The buffers 430 facilitate the oscillator signal outputs (e.g., oscillations generated by LC circuits of the oscillator module 420) to be combined. The transducer module 440 may be connected such that only one of the transmit or receive pathways may be connected at any given time; an additional Schmitt trigger 450 may be used with the rectified summed signal to control this connection and prevent the transmission signal from retriggering the clip circuit. When the signal rings down, the original switch may be opened, facilitating the clip to await triggering from the imaging pulse. A small battery 460 may be used to excite the LC oscillator circuits of the oscillator module 420. The battery 460 may be sized to power the buffers and oscillators when triggered by ultrasound. However, because the triggering events may be very sparse in time and only occur during three time points, which mainly occur at implantation, localization before surgery and intraoperatively at the time of surgical retrieval often after completion of NAC, the battery life may sustain for several months (e.g., 2, 3, 4, or more months) for the duration of clip operation. For a given design instance, power draw calculations may be determined for the final circuit design to select the smallest battery for the clip that will provide the full power anticipated to be used during the life of the clip. The power draw calculations may also be used to verify power draw during operation of the clip.

The signal that returns to the imaging array from the clip may be of low pressure similar to sound scattered back to the transducer. Because the clip may comprise a lumped circuit with no delay lines, the signal re-emitted from the clip may be nearly instantaneous with its triggering. Therefore, the signal arriving at the imaging array from the clip may be used to range the clip location via pulse-echo processing assuming the sound speed in the tissue is known or approximated, e.g., assumed sound speed of 1540 m/s for soft tissue. However, the signal returned to the imaging array may have properties allowing the clip to not only be clearly identified in the image but also to provide a unique identification number allowing the clip to be correlated to a specific lymph node or tumor site designated at the time of implantation. The broadband nature of the imaging pulse may allow each of the oscillators to be excited because the oscillators may be tuned to have outputs within the bandwidth of the imaging probe. Each oscillator may have different resonant frequencies and be a high Q resonator. Therefore, the output signals from the oscillators may operate in orthogonal bands and each of these bands may be detected separately through appropriate signal processing steps to identify that a clip is in the imaging field and the ID of the clip in the field. For example, with a 3-bit system operating at a center frequency of 10 MHz, capturing tone bursts at 8, 10 and 12 MHz may utilize a 40% bandwidth. Moving to a higher bit count may utilize either a larger bandwidth or narrower band (higher Q) oscillators. Using a multiple-bit system, if multiple clips were in the imaging field of the imaging array, each clip could be separately identified in real time.

Various implementations of the USID clip technology described herein may be realized via design, build, and test of a radiological clip circuit as described herein. The radiological clip circuit corresponding to an exemplary implementation may be simulated using LTSpice and then physically constructed using breadboards. This approach facilitates adjustment of different circuit components and corresponding parameter values, tuning the oscillators, and adjusting threshold values for the two triggers in the circuit design. To test and evaluate an implementation of the clip in an application, the transducer may be separated from the breadboard and connected via a longer cable. This connection via the longer cable may facilitate testing and evaluating the clip in a water tank by just immersing the transducer or by embedding the transducer, while still connected to the circuit, into a tissue-mimicking material or tissue sample. Small piezo crystals (e.g., Sonometrics) may be cut to have a center frequency of 10 MHz when combined with epoxy backing, which also enables broadband signaling and a low directivity making them near omnidirectional. These crystals may be used as the small transducer in the radiological clip. Imaging may take place using an L14-5/38 transducer connected to a Verasonics Vantage system, for example. The L14-5/38 array probe may provide frequencies that span five (5) to fourteen (14) MHz. The Verasonics system may facilitate capturing the raw RF signals from the imaging probe and utilizing custom software to detect, identify and image the clip signals in B-mode ultrasound.

Software including computer-readable instructions that when read by a computing processor cause the computer processor to perform a sequence of specific operations based on various input values may process signals from clips and display the signals corresponding to clips along with corresponding IDs on registered B-mode images in real time. Software may perform image and/or signal processing to detect the presence of one or more clips within a field of image data and determine the identification number (e.g., USID) of each detected clip. To isolate a radiological clip signal from different background signals, a pulse-inversion scheme may be used to eliminate the fundamental tissue signal. Pulse-inversion imaging techniques may be used to create harmonic images and are ubiquitous on modern clinical ultrasound machines. Pulse inversion ultrasound includes creating an image first with a positive pulse and then another image with a negative pulse (e.g., the negative pulse being 180 degrees out of phase with the positive pulse). These two images may then be summed together resulting in subtraction of odd harmonics, including the fundamental band, and leaving even harmonics for image formation. The software for use with the USID clips described herein may use pulse-inversion ultrasound to eliminate the tissue signal at the fundamental band leaving behind the radiological clip signal, which may also be within the fundamental band but not changing its polarity with positive or negative imaging pulses. On the clip, circuitry may rectify the signal transmitted from the transducer to the trigger switch so that the circuitry may be triggered by the same image pulse location whether the pulse is a positive or negative imaging pulse.

Figure 5A:
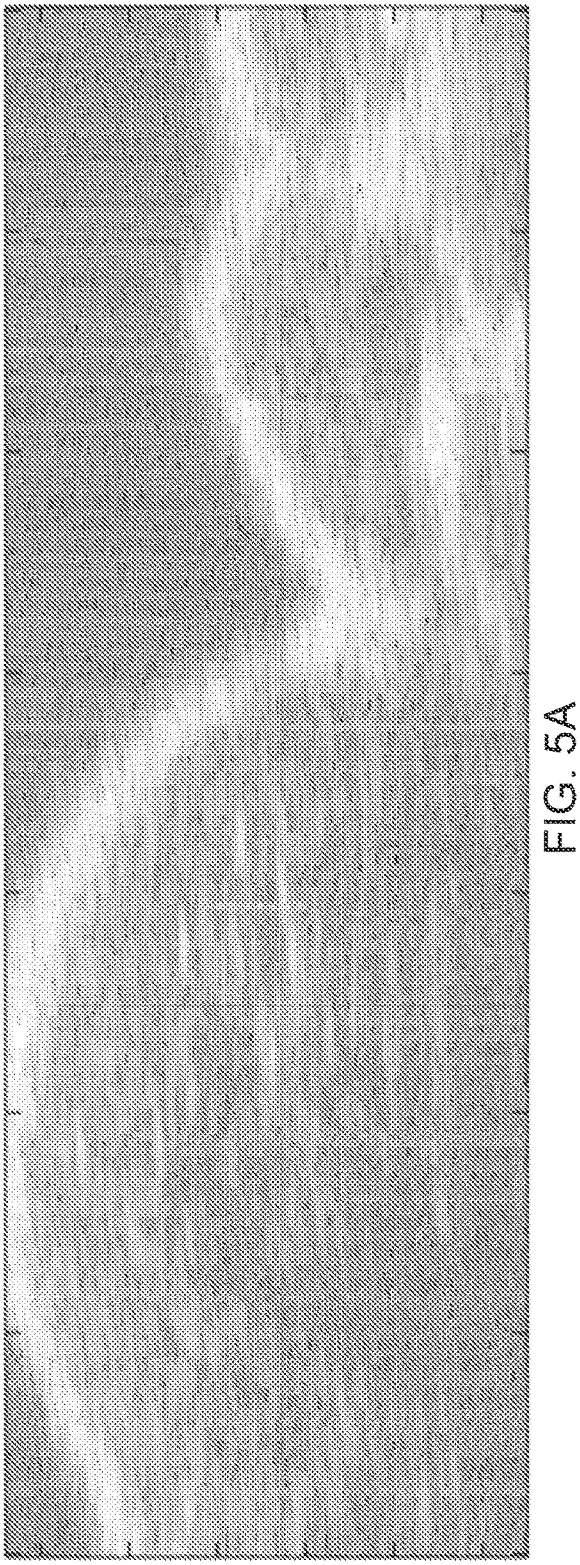
FIG. 5A illustrates an exemplary simulated B-mode image of a tumor with a clip signal embedded.
Figure 5B:
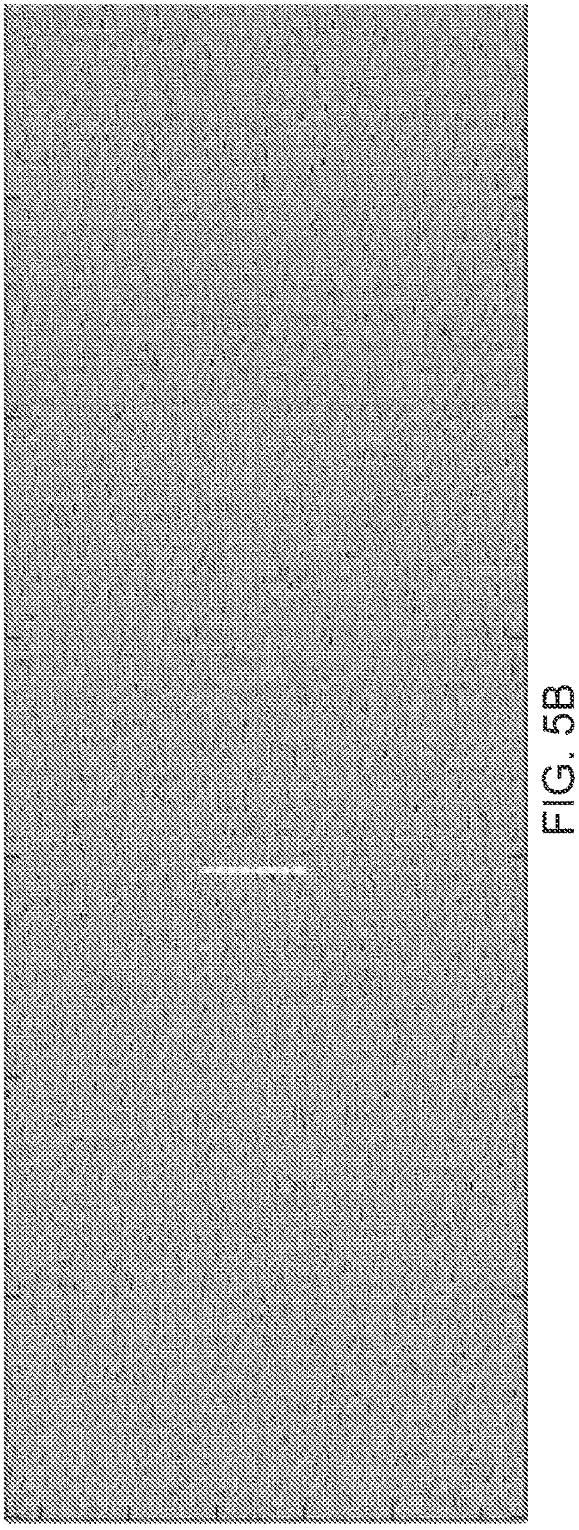
FIG. 5B illustrates an exemplary simulated clip signal after pulse inversion processing to remove tissue signal leaving only the clip signal.
Figure 5C:
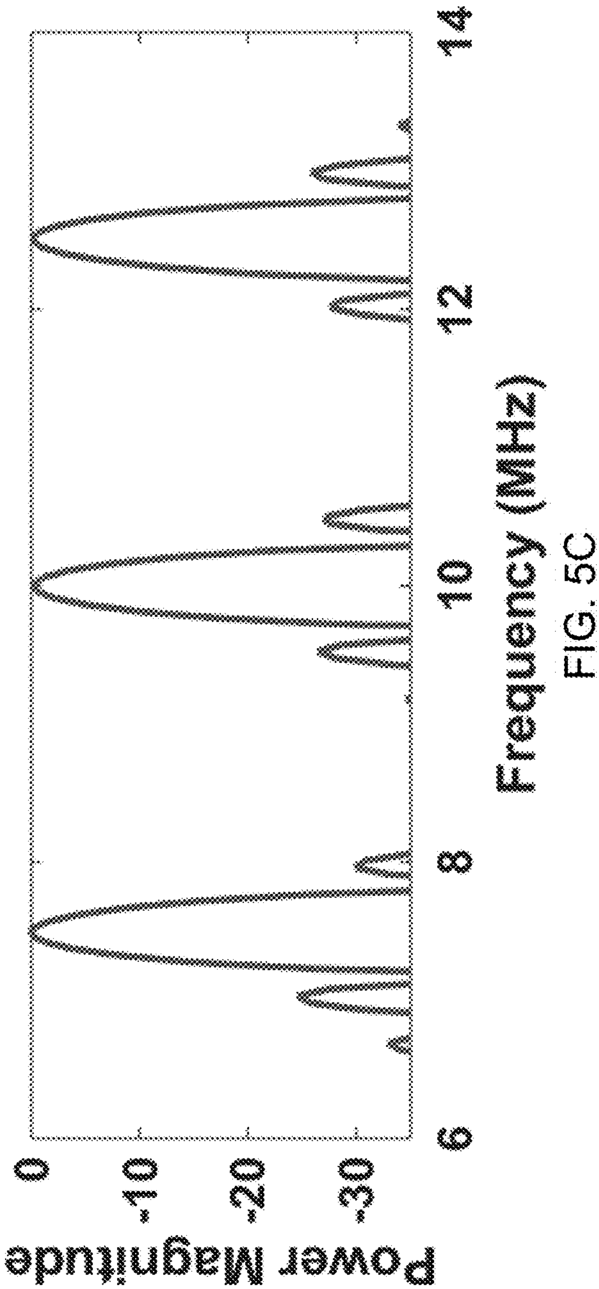
FIG. 5C illustrates an exemplary frequency spectrum of a clip signal.
Figure 5D:
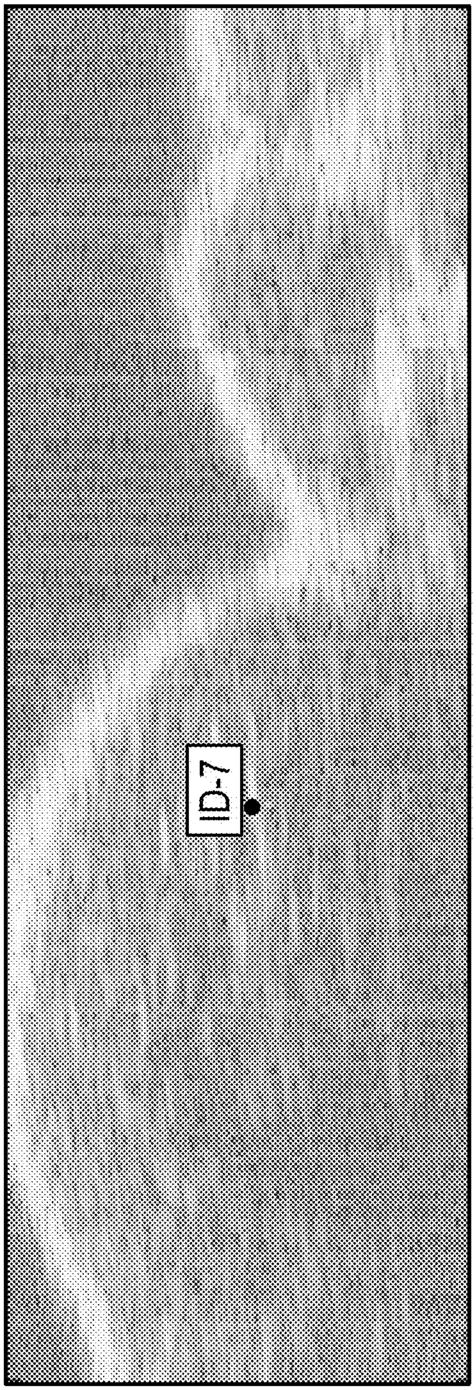
FIG. 5D illustrates a B-mode ultrasound image including a clip USID.

FIG. 5A illustrates an exemplary simulated B-mode image of a tumor with a clip signal embedded. FIG. 5B illustrates an exemplary simulated clip signal after pulse inversion processing to remove tissue signal leaving only the clip signal. FIG. 5C illustrates an exemplary frequency spectrum of a clip signal. FIG. 5D illustrates a B-mode ultrasound image including a clip USID. While FIGS. 5A-5D show a single clip within the B-mode image, in various examples, multiple clips may be shown within the B-mode image, and the multiple clips may each have a different corresponding USID to distinguish them from each other in the image.

Figure 6:
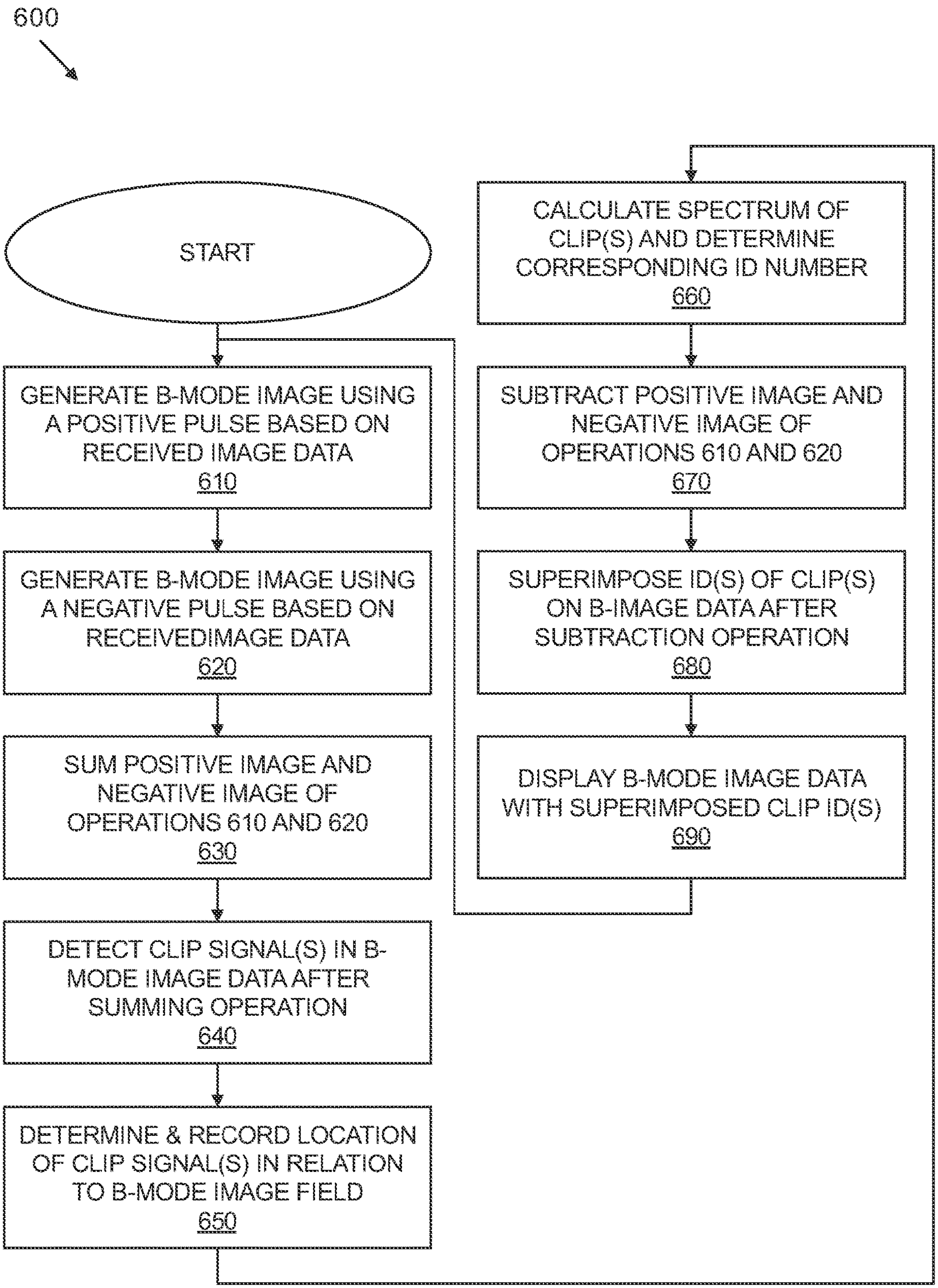
FIG. 6 is a flow chart that illustrates an exemplary method of processing ultrasound image data and clip signal data to display a B-mode ultrasound image with an overlaid USID of a corresponding clip within the image.

FIG. 6 is a flow chart that illustrates an exemplary method 600 of processing ultrasound image data and clip signal data to display a B-mode ultrasound image with an overlaid USID of a corresponding clip within the image. In various examples, multiple clips may provide their respective clip signal data and be represented by their different respective USID numbers within the displayed B-mode image to distinguish them from each other in the image.

In an operation 610, an image may be generated using a positive pulse. The generated image may be similar to the simulated B-mode image of a tumor with a clip signal embedded therein as shown in FIG. 5A. In an operation 620, an image may be generated using a negative pulse. The generated image may also be similar to the simulated B-mode image of a tumor with a clip signal embedded therein as shown in FIG. 5A. In an operation 630, the images generated in operations 610 and 620 may be summed to eliminate tissue signal in the fundamental band. The summed image may be similar to the image of FIG. 5B.

In an operation 640, the clip signal(s) of one or more clips may be detected through thresholding of the signal strength. In an operation 650, a location of the clip signal(s) may be determined in relation to the B-mode image field and the location(s) may be recorded. For each of one or more clips in the B-mode image field, the lateral location of the clip may be identified by the particular scan line(s) in which the clip signal is detected. The axial location may be estimated based on the time sample at which the clip signal is first detected in the field. The time sample index may be used to calculate the physical depth of the clip in relation to the transducer surface through the speed of sound.

In an operation 660, the spectrum of each clip signal may be calculated and the ID corresponding to the clip signal may be estimated based on the presence of signal or lack of signal at selected narrow frequency bands. An exemplary clip signal spectrum is shown in FIG. 5C. For example, referring to FIG. 5C, in the case of a clip that may either transmit or not transmit a narrow band signal centered around any of about 7.5 MHz, 10 MHz, or 12.5 MHz, the presence of a narrow band signal centered around the respective frequency may indicate a binary 1 corresponding to the position indicated by the respective frequency. A decimal number from 1 to 7 may be represented by the presence of a narrow band signal in one or more of the narrow frequency bands centered around any of about 7.5 MHz, 10 MHz, or 12.5 MHz. The presence of a narrow band signal in each of the frequency bands as illustrated in FIG. 5C may correspond to an ID of 7 as represented in decimal base. The clip signal spectra for each of multiple clips within the B-mode image may be separated from the signal spectra for other clips for separate analyses using various beamforming techniques.

In an operation 670, the positive and negative pulse image data generated in operations 610 and 620, respectively, may be subtracted to generate a B-mode image without the clip signal. Various different beamforming techniques may be applied to create the B-mode image from the raw subtracted data.

In an operation 680, the ID of each of the one or more clips as determined in operation 660 may be superimposed on the B-mode image generated in operation 670 for display, as shown in FIG. 5D. Note that the clip marker may be artificially generated for the display and placed on top of the B-mode image. Its visibility may be set in an ON or OFF state, unlike prior commercial clips whose echogenicity in the image depends on the orientation of the clip with the transducer and can, therefore, range from visible to invisible in the image. In an operation 690, B-mode image data including the superimposed clip ID(s) from operation 680 may be displayed on a video display.

Operational parameters for clip circuitry, for example, thresholds, in different applications may be determined according to experimental measurements simulating the different applications. The radiological clips may be triggered by an ultrasonic imaging pulse. When ultrasonic imaging pulses of different powers are sent to the clip, for example, when embedded within tissue, the received signal levels at which the switch is triggered may be monitored electronically. Clip activation may be further quantified as the beam passes over the clip in the elevational direction. Experimental measurements may also determine and/or verify threshold values for the circuitry that facilitate the clip to be triggered as desired from the ultrasonic imaging pulses, but not by scattering or reverb of ultrasonic pulses, such as would be encountered in human tissues. These experimental measurements may be performed by placing the clip transducer in a reverberant setting, such as a chicken breast sample, to ensure that the detection switch is not triggered by scattered pulses or reverb at different threshold values and/or other parameter values. Experimental measurements may verify that the clip transmits a single tone burst in response to a single trigger event. An imaging pulse may be transmitted to the clip transducer and the output of the clip transducer upon triggering may be recorded. The software processing operations may be verified to detect the presence of one or more clip signals in the field of view when the threshold and any other parameters have been set to desired values according to the intended application of the clips. An example measurement may involve configuring two clips on two different breadboards having different IDs and placing their transducers in the field of the imaging array. The response of the clips may be measured while the software may be employed to localize and ID the clips as well as superimpose their locations and/or ID numbers on B-mode images of the medium.

Figure 7:
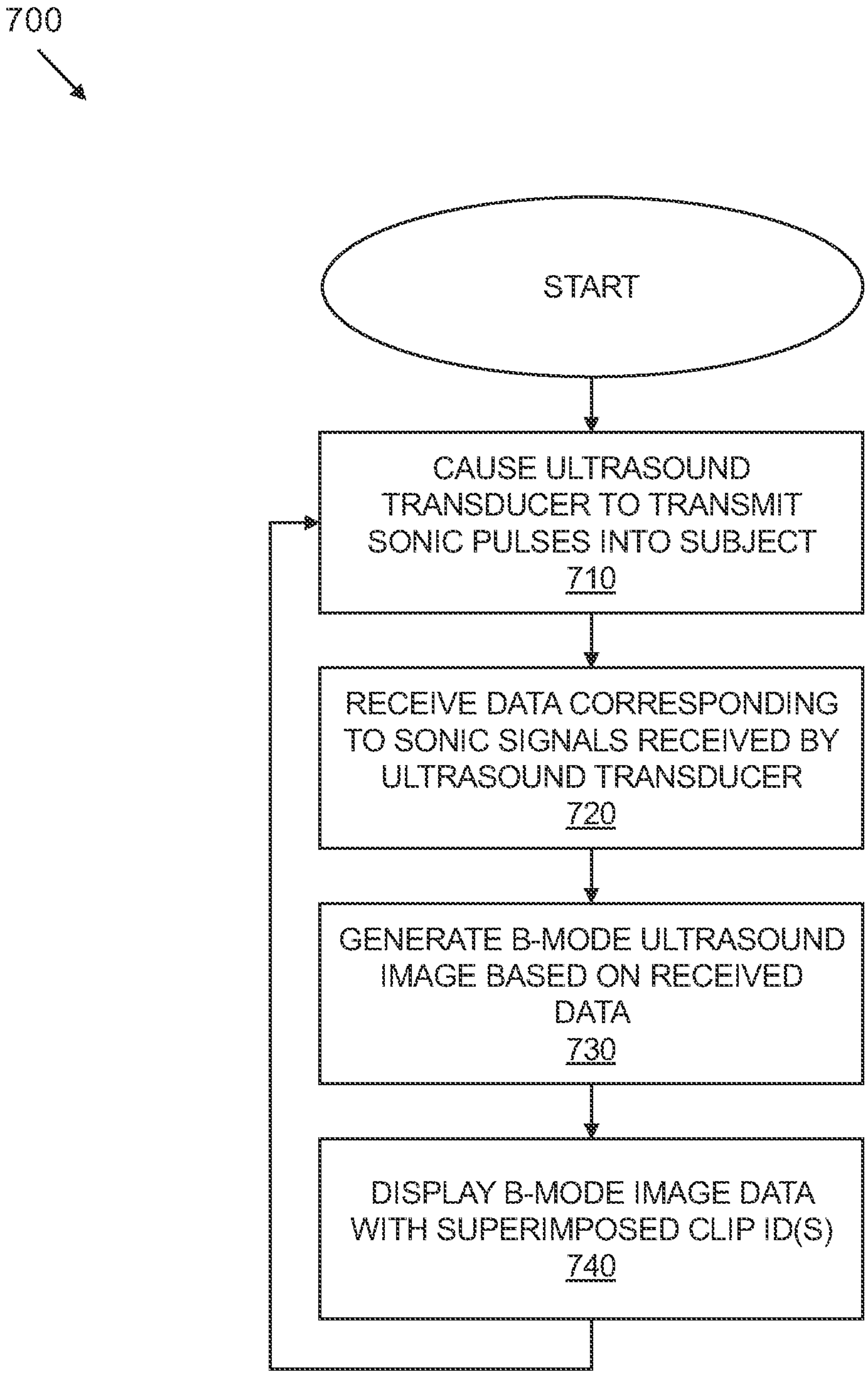
FIG. 7 is a flow chart that illustrates an exemplary method of performing ultrasound imaging of a subject having a marker clip that emits an identifying signal in response to receipt of an ultrasound signal.

FIG. 7 is a flow chart that illustrates an exemplary method 700 of performing ultrasound imaging of a subject having a marker clip that emits an identifying signal in response to receipt of an ultrasound signal. In an operation 710, an ultrasound transducer may be controlled to transmit sonic pulses toward or into a subject. Information regarding the transmitted sonic pulses may be stored in a database and/or electronic memory device for subsequent use in analyses of received signals and image generation. The stored information may include frequency, amplitude, phase, and/or time of pulse transmission data for the ultrasound transducer overall and/or for each of one or more transmission elements (e.g., piezoelectric crystals) included in the ultrasound transducer.

In an operation 720, data corresponding to sonic signals received by the ultrasound transducer may be received. The received data may include frequency, amplitude, phase, and/or time of receipt data for the ultrasound transducer overall and/or for each of one or more receiver elements included in an imaging array of the ultrasound transducer. The received data may include data corresponding to tissues within the subject and also data corresponding to USID signals transmitted by one or more marker clips (e.g., the novel radiological clip described herein) within the subject. The novel radiological clip described herein may include an electronic circuit that transmits an encoded signal providing USID when triggered by a received ultrasonic image pulse (e.g., a sonic pulse transmitted by the ultrasound transducer). The encoded signal may be received by the imaging array and included in the received data provided by the ultrasound transducer.

In an operation 730, a B-mode ultrasound image may be generated based on the received data. The B-mode ultrasound image may be generated according to method 600 described herein. The data corresponding to the encoded signal provided by a clip may be processed to localize the clip as well as provide an ID of the imaged clip. In the potential event that noise in the signal from the imaging pulses using the pulse inversion scheme described with reference to method 600 causes consecutive triggers between positive and negative pulsing to result in offsets between outputs leading to potential partial cancellation of the clip signals, initial input from the clip may be adjusted and a low pass filter may be added to reduce noise artifacts.

In an operation 740, the B-mode ultrasound image including the superimposed clip ID(s) may be displayed on a video display, for example, as described with reference to method 600 illustrated in FIG. 6.

An implementation of the novel marker clip technology described herein may include a printed circuit board (PCB) having all components of the clip attached thereon and encapsulated within a waterproof and/or hermetically sealed container, for example, silicon-modified conformal coatings and small metal sheath to prevent degradation of the circuit components when immersed in water or embedded in tissue material. Encapsulation may further include wrapping the PCB and/or circuitry and associated components in thin plastic material to isolate the circuit components. Encapsulation of the novel clip may prevent degradation of clip's electronics when embedded within subjects such as phantom materials, biological tissue samples, patients, water, etc. Some implementations of the PCB may have dimensions (e.g., in a double stack implementation) that are larger than 1 $cm^2$. Some implementations of the PCB may have dimensions that are smaller than 1 $cm^2$.

An implementation of the novel marker clip technology described herein may include an application-specific integrated circuit (ASIC) designed to replace the PCB to further miniaturize the design for use in applications within patient tissues. The ASIC may be designed to take into consideration likely environmental conditions of the patient during cancer treatment, for example, radiation therapy, radiological imaging, changes in tissues surrounding the USID clip in response to treatment, etc. The ASIC may be designed for X-ray and MRI compatibility and to address migration issues. An ASIC design may enable millimeter-sized circuits, minus battery and transducer, to be constructed, facilitating miniaturization of the USID clip for in vivo and human use. In an example, the USID clip may be encapsulated in a small titanium shell for biocompatibility. Additional methods may also be utilized to make the USID clips biocompatible for long-term use [Bou19].

The described clip design may have superior signal-to-noise ratio (SNR) compared to prior commercial clip designs relative to the background tissue signal, at least because prior commercial clips change visibility according to transducer orientation. Because clip orientation plays a large role in SNR, SNR may vary greatly in prior commercial clips depending upon whether they are oriented favorably or unfavorably for imaging relative to the ultrasound transducer. In contrast to prior commercial marker clips, the visibility of the novel clip described herein does not depend upon the echogenicity of the clip, but rather on the unique clip signal that is emitted by the novel clip, received by the ultrasound transducer, and processed by the novel methodology described herein. The SNR and visibility for the novel clip described herein may not depend upon orientation of the clip. As long as the ultrasound transducer receives a USID signal from the novel clip described herein, the SNR and visibility of the novel clip may be independent of the clip's orientation within a subject relative to the ultrasound transducer.

Example System Architecture

Figure 8A:
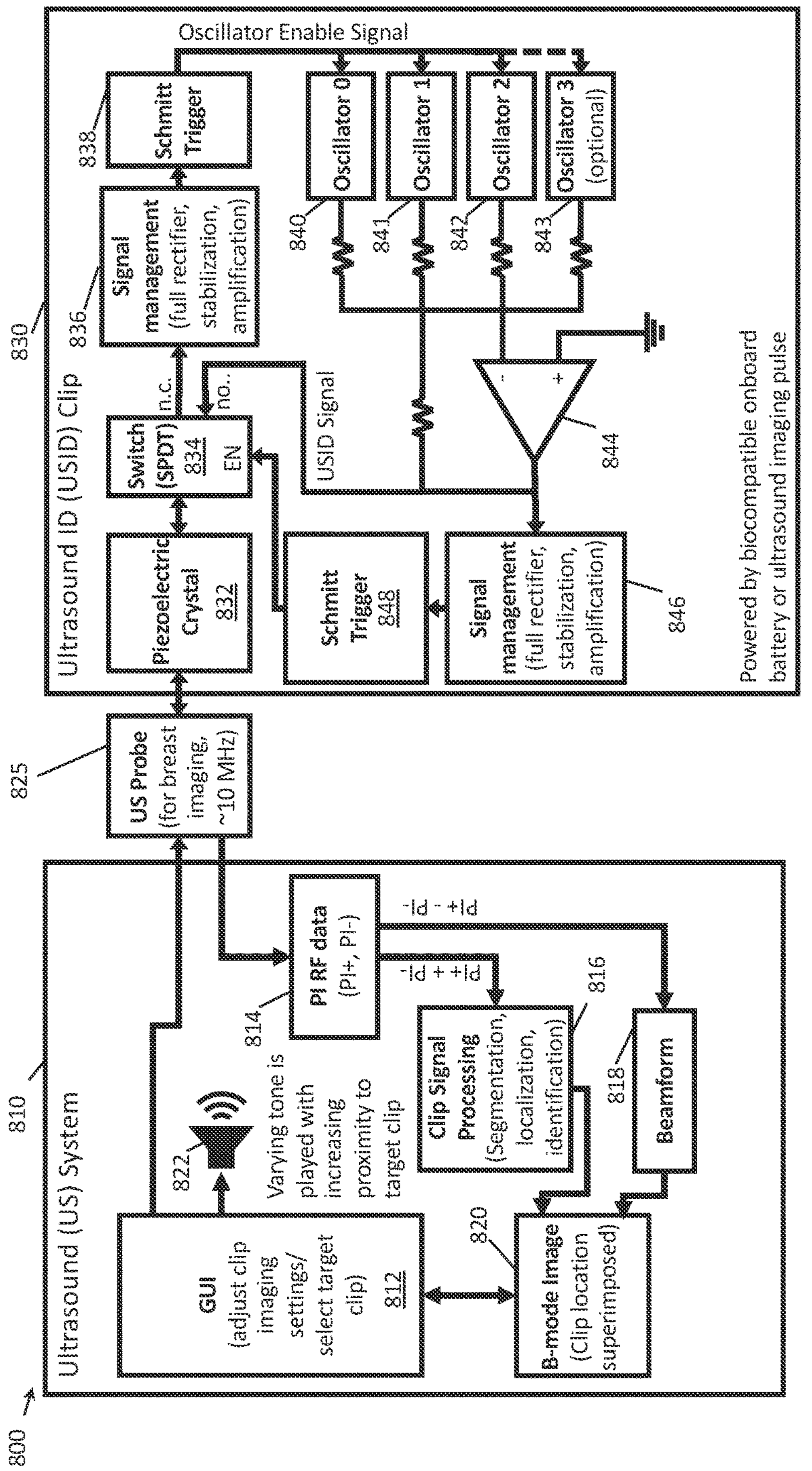
FIG. 8A is a block diagram illustrating an exemplary system architecture of an ultrasound (US) system that is configured to visualize and locate one or more novel USID clips as described herein.

FIG. 8A is a block diagram illustrating an exemplary system architecture 800 of an ultrasound (US) system 810 and novel USID clips 830 as described herein which the US system 810 is configured to visualize and locate during ultrasound imaging operations. FIG. 8A also illustrates exemplary process and signal flow between components of the architecture 800. The specific components and circuits illustrated and described with reference to the exemplary system architecture 800 herein may potentially be replaced with other components and circuits having similar functionality and/or capabilities in other exemplary architectures or use cases without departing from the principles, scope, or spirit of this disclosure. The US system 810 may include a graphical user interface (GUI) 812 that facilitates adjustments to various clip imaging settings and setting one or more different target clips 830 to visualize and locate based on unique ID numbers associated with the target clips 830. The GUI 812 may be displayed on a visual monitor or display according to computer-readable instructions stored in a memory device that are executed by a computing processor of the US system 810. An ultrasound system probe 825 may be controlled by the US system 810 according to settings of the GUI 812 to perform a diagnostic imaging operation, for example, diagnostic imaging of breast tissue. The US probe 825 may emit ultrasound pulses toward a subject of the diagnostic imaging operation via an array of ultrasound transducers (e.g., piezoelectric crystals). The US probe 825 may also detect ultrasound signals returned by the subject in response to the emitted ultrasound pulses. The US probe 825 may generate radio frequency (RF) signals corresponding to the detected returned ultrasound signals and provide the RF signals to the US system 810 for processing. The detected ultrasound signals may include ultrasound identification (USID) signals received from one or more USID clips 830 present in the subject and/or imaging field.

The US system 810 may perform signal processing on the RF signals received from the US probe 825 to generate pulse inverted (PI) RF data 814 corresponding to the received RF signals. The PI RF 814 data may include both positive pulse RF data and negative pulse RF data as described elsewhere herein. A clip signal processing component 816 may perform signal processing on the PI RF data, for example, summed PI+ RF data and PI− RF data, and perform segmentation, localization, and identification operations on the PI RF data. A beamforming component 818 may perform beamforming signal processing operations on the PI RF data, for example, subtracted PI+ RF data and PI− RF data. Outputs of both the clip signal processing component 816 and the beamforming component 818 may be input to and used by a B-mode imaging component 820 to generate a B-mode ultrasound image of the subject based on ultrasound signals sent and received by the US probe 825. The generated B-mode image may include both an image of the tissues and/or other materials that respond to the ultrasound pulses transmitted by the US probe 825 within the image field of the subject, and a location and ID of the USID clip(s) 830 located within the image field of the subject. FIG. 5D may include an example of a B-mode ultrasound image produced by the B-mode imaging component 820.

The USID clip 830 may be a minitiarized, self-contained, and/or hermetically sealed capsule including electronic circuitry and an ultrasound transducer (e.g., piezoelectric crystal) to both receive and send ultrasound signals. The USID clip 830 may include a power source to drive its electrical circuitry and ultrasound transducer. The power source may include a biocompatible onboard battery and/or components and/or circuitry to generate sufficient power from received ultrasound energy (e.g., from an ultrasound imaging pulse) to drive the USID clip 830's circuitry to transmit a USID signal in response to receipt of the ultrasound imaging pulse.

The USID clip 830 may include a piezoelectric crystal 832 that generates an electrical signal corresponding to ultrasound signals received from the US probe 825. The piezoelectric crystal 832 may send the generated electrical signal through signal management circuitry 836 to a Schmitt trigger 838 to trigger generation of an ultrasound ID (ISID) signal when a switch (e.g., an SPDT switch) 834 is enabled to pass the electrical signal from the piezoelectrical crystal 832 to trigger generation of the USID signal by the USID clip 830. The signal management circuitry 836 may include a full rectifier, stabilization, and/or amplification of the electrical signal to reliably cause the Schmitt trigger 838 to trigger when an ultrasound signal is received from the US probe 825 and avoid false triggers in response to other signals, reflections, reverberations, noise, etc. that impact the piezoelectric crystal 832. As described below, the switch 834 may be configured to be enabled during normal operation of the USID clip 830 except for periods of time in which the USID clip 830 is transmitting a USID signal via the piezoelectric crystal 832 in response to a previously received ultrasound signal from the US probe 825.

When the Schmitt trigger 838 is triggered by an electrical signal representing an ultrasound signal received from the US probe 825 by the piezoelectric crystal 832, the Schmitt trigger 838 may transmit an oscillator enable signal to cause generation of electrical signals by one or more of oscillators 840, 841, 842, 843 representing binary bit positions 0, 1, 2, and 3, respectively, of a binary identification number which the USID clip 830 instance is configured (e.g., programmed, wired, etc.) to transmit. While up to four oscillators are illustrated, this should not be considered limiting, as any number of oscillators may potentially be used within the USID clip subject to practical considerations of the application in which the USID clip 830 is to be utilized. The specific ones of the oscillators 840, 841, 842, 843 that are configured to generate electrical signals may correspond to '1' bits within a multiple-bit binary number representing the ID of the specific USID clip 830 instance. Each of the oscillators 840, 841, 842, 843 may generate a sinusoidal signal at a different frequency than the other of the oscillators 840, 841, 842, 843 when enabled and configured to operate as described elsewhere herein. The signals output by each of the enabled and operating oscillators 840, 841, 842, 843 may be summed together and amplified by an amplifier 844 to generate a USID signal. The generated USID signal may be operated upon by signal management circuitry 846, which may include full rectifier circuitry, stabilization circuitry, and/or amplification circuitry, and then drive a Schmitt trigger 848 to change an enable state of the switch 834. When the USID signal is generated by the USID clip 830's oscillator and amplifier circuitry, the generated USID signal may trigger a change in the enable state of the switch 834 via the Schmitt trigger 848 to prevent electrical signals generated by the piezoelectric crystal 832 in response to received ultrasound pulses to pass through the switch 834 toward the Schmitt trigger 838, and instead to pass the USID signal from the amplifier 844 through the switch 834 to the piezoelectric crystal 832 to transmit the USID signal from the USID clip 830 back to the US probe 825.

Example System Demonstration

Figure 8B:
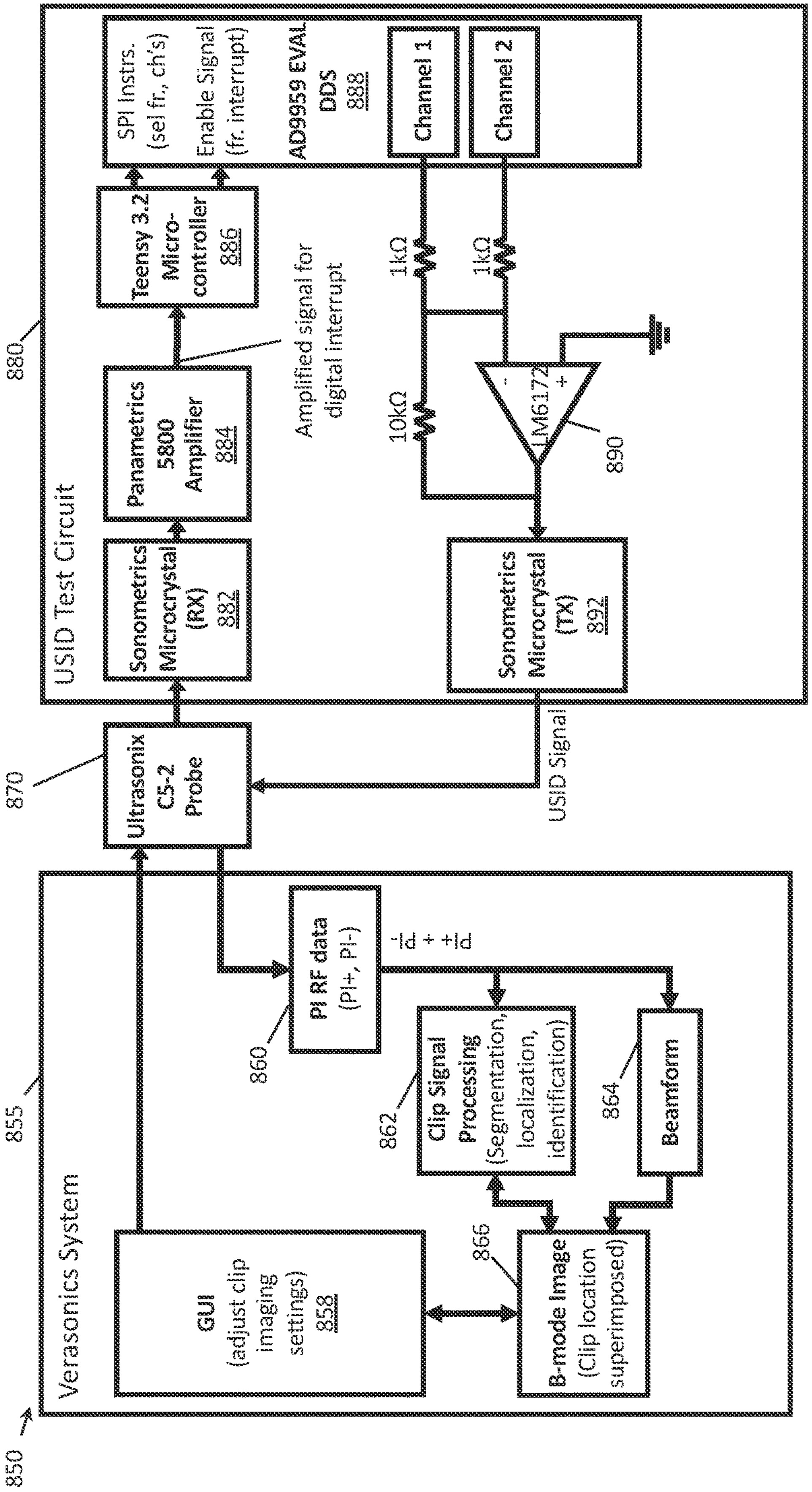
FIG. 8B is a block diagram illustrating an exemplary system architecture of a Verasonics ultrasound (US) system that is configured to visualize and locate a USID test circuit as described herein.

FIG. 8B is a block diagram illustrating an exemplary system architecture 850 of a Verasonics ultrasound (US) system 855 that is configured to visualize and locate a USID test circuit 880 as described herein. The exemplary system architecture 850 represents a demonstration platform for experimentally demonstrating aspects of the exemplary system architecture 800 described herein, including with reference to FIG. 8A. FIG. 8B also illustrates exemplary process and signal flow between components of the architecture 850. The Verasonics system 855 may include an example of the US system 810 and the USID test circuit 880 may be an example of the USID clip 830. The system architecture 850 may also include an Ultrasonix C5-2 probe 870 as an example of the US probe 825. The specific components illustrated and described with reference to the experimental demonstrations described herein may potentially be replaced with other components having similar functionality and/or capabilities in other demonstrations or use cases without departing from the principles, scope, or spirit of this disclosure. For example, the Verasonics US system 855 was used as a test platform in the experimental demonstrations described herein, but any of a variety of other systems may potentially be used. For example, an FDA approved clinical ultrasound system may be used in a medical practice setting instead. In addition, specific frequencies described with respect to performing this experimental demonstration may be chosen to be different in further experimental demonstrations and/or in field applications of the described technologies in clinical settings. For example, the experimental demonstration described herein was performed using lower frequencies than are anticipated to be used in clinical settings.

The Verasonics system 855 may include a graphical user interface (GUI) 858 that facilitates adjustments to various clip imaging settings and setting one or more different target USID test circuits 880 to visualize and locate based on unique ID numbers associated with the target USID test circuits 880. The GUI 858 may be an example of the GUI 812. The GUI 858 may be displayed on a visual monitor or display according to computer-readable instructions stored in a memory device that are executed by a computing processor of the Verasonics system 855. The Ultrasonix C5-2 probe 870 may be controlled by the Verasonics system 855 according to settings of the GUI 858 to perform a diagnostic imaging operation, for example, diagnostic imaging of phantom tissue simulating biological tissue. The probe 870 may emit ultrasound pulses toward a subject of the diagnostic imaging operation via an array of ultrasound transducers (e.g., piezoelectric crystals). The probe 870 may also detect ultrasound signals returned by the subject in response to the emitted ultrasound pulses. The probe 870 may generate radio frequency (RF) signals corresponding to the detected returned ultrasound signals and provide the RF signals to the Verasonics system 855 for processing. The detected ultrasound signals may include ultrasound identification (USID) signals received from one or more USID test circuits 880 including ultrasound transducers present in the subject and/or imaging field.

The Verasonics system 855 may perform signal processing on the RF signals received from the probe 870 to generate pulse inverted (PI) RF data 860 corresponding to the received RF signals. The PI RF data 860 may include an example of the PI RF data 814. The PI RF data 860 may include both positive pulse RF data and negative pulse RF data as described elsewhere herein. A clip signal processing component 862 may perform signal processing on the PI RF data, for example, summed PI+ RF data and PI− RF data, and perform segmentation, localization, and identification operations on the PI RF data. The clip signal processing component 862 may include an example of the clip signal processing component 816. A beamforming component 864 may perform beamforming signal processing operations on the PI RF data, for example, summed PI+ RF data and PI− RF data. The beamforming component 864 may include an example of the beamforming component 818. Outputs of both the clip signal processing component 862 and the beamforming component 864 may be input to and used by a B-mode imaging component 866 to generate a B-mode ultrasound image of the subject based on ultrasound signals sent and received by the probe 870. The B-mode imaging component 866 may include an example of the B-mode imaging component 820. The generated B-mode image may include both an image of the subject materials that respond to the ultrasound pulses transmitted by the probe 870 within the image field of the subject, and a location and ID of the USID test circuit(s) 880 (or ultrasound transducers thereof, as the case may be according to the demonstration described herein) located within the image field of the subject. FIG. 5D may include an example of a B-mode ultrasound image produced by the B-mode imaging component 866.

The USID test circuit 880 may be an experimental representation or simulation of a design of the USID clip 830, as described below. The USID test circuit 880 may include a Sonometrics microcrystal 882 configured as a receiver to receive ultrasonic pulses from the Ultrasonix C5-2 probe 870 and generate a corresponding electrical signal. The Sonometrics microcrystal 882 may send the generated electrical signal through a Panametrics 5800 amplifier 884 to generate an amplified signal for digital interrupt to input into a Teensy 3.2 microcontroller 886 for triggering generation of USID signal by the USID test circuit 880. The Teensy 3.2 microcontroller 886 may send electrical signals into an AD9959 Eval DDS board 888 including SPI instructions (e.g., to select frequencies and channels for the USID signal components) and enable signals (e.g., from the amplified signal for digital interrupt input into the Teensy 3.2 microcontroller 886).

In response to the AD9959 Eval DDS board 888 receiving signals from the Teensy 3.2 microcontroller 886 corresponding to receipt of an ultrasound imaging pulse by the Sonometrics microcrystal RX 882, the AD9959 Eval DDS board may cause generation of sinusoidal signal components of a USID signal in one or both of channel 1 and channel 2 according to the particular USID number that the particular instance of the USID test circuit 880 is configured to transmit. The two channels 1 and 2 may represent any two '1' bit values of a binary number having any total number of bits in simulating a USID clip 830. For example, channels 1 and 2 of the AD9959 Eval DDS board 888 may represent any two of oscillators 840, 841, 842, 843 representing binary bit positions 0, 1, 2, and 3, respectively, of a binary identification number which the USID clip 830 instance being simulated may be configured (e.g., programmed, wired, etc.) to transmit. The signals output by each of the channels 1 and 2 may be summed together and amplified by an amplifier 890, e.g., an LM6172 amplifier, to generate an electronic USID signal. The amplifier 890 may include an example of the amplifier 844. The amplifier 890 may pass the electronic USID signal to a Sonometrics microcrystal TX 892 to transmit a corresponding USID signal to the Ultrasonix C502 probe 870. The Sonometrics Microcrystal TX 892 may include an example of the piezoelectric crystal 832 for transmitting a USID signal from the USID test circuit 880 back to the probe 870.

An exemplary implementation of the novel USID clip 830 described herein, similar to that described with reference to FIG. 8B above, was demonstrated experimentally. A USID signal was generated by an AD9959 evaluation board 888 controlled by a Teensy 3.2 microcontroller 886, simulating a USID clip 830, and imaged in water via pulse inversion imaging on a Verasonics ultrasound system 855 as an example of the ultrasound system 810 coupled with a commercial ultrasonic probe (e.g., an Ultrasonix C5-2 probe 870) as an example of the US probe 825. Spectral visualizations of the received signal showed clear differences between the six tested ID numbers.

The example implementation of the novel marker clip described herein synthesized the localization and identification problems of marker clips for ultrasound imaging into a single solution that may be readily and accurately imaged under ultrasound. The example radiological clip is a powered electronic device, instead of a passive object which merely reflects or scatters acoustic energy. This powered device may have four major components: a piezoelectric element which may receive and send electrical signals through tissue as acoustic pressure waves; circuitry to generate an ultrasound identification (USID) signal ready for transmission in response to being triggered by a logic signal; circuitry to prevent the outgoing transmit signal from retriggering the USID signal generating circuitry; and a power source for the clips circuitry as a whole. The final novel USID clip product using these components should be small in size, around 1-10 mm in length, to remain competitive with available marking clips for use in human patients. This small size facilitates the clips to mark a wider array of tumors and be inserted in a minimally invasive manner. Maintaining a power delivery device able to fit the required size profile while still having enough charge to last for several months idle during NAC is a driver for the circuit design to use power efficiently and incorporate a limited set of features. The novel clip may be encased in a biocompatible shell or outer layer. Just as important as the circuit design is the design of the USID signal itself, which the USID circuitry is designed to generate. The USID signal may have the following desirable features:

- Information may be extracted from the signal with minimal processing resources, so as to maintain high frame rates which facilitate responsive visual feedback for operators,
- The USID signal may be tunable, e.g., the clip circuitry may be capable of generating multiple identification signals from one clip circuitry design with minimal alteration, and • The USID signal may be of a sufficient time duration so that it does not "bleed into" the next ID acquisition period or be so short as to be unable to encode information or provide additional visibility with which to localize the clip.

Based on these considerations, the novel marker clip described herein may generate a USID signal as an analog signal with three (or more) sinusoidal components generated by oscillators. Each sinusoidal component may have a fixed, pure tone frequency which falls within the imaging bandwidth of the US probe; these signals may be turned on and off, either programmatically or manually by an operator of the US system, or at time of manufacture by simply leaving certain sections of a fabricated circuit board depopulated of active circuit elements. Because the frequencies of the pure tone sinusoidal components would be known, the signal received by the US system may be evaluated to determine if each individual frequency component of the full USID signal is present or absent. If it is present, this would represent a binary 1, while an absence would represent binary 0. With three different sinusoidal component signal frequencies, a three-bit number may be generated, for a total of 7 identification numbers. (The case where all three different sinusoidal component signal frequencies are absent, 000, does not represent a valid visible signal, and so is excluded from the supported USIDs.) With four different sinusoidal component signal frequencies, a four-bit number may be generated, for a total of 15 identification numbers. Information encoded in this way may be readily and quickly decoded by an ultrasound system by windowing the received data to the area where the signal is present and finding the spectral representation of that data via the fast fourier transform (FFT). Checking for the presence or absence of frequencies may be readily performed by a computing processor and/or electronic circuitry in the US system; if at any of the given frequencies, there were local maxima which passed a certain threshold above the baseline noise, those frequencies may be marked as present.

Both the background signal in vivo and the systems used to perform imaging may vary greatly. To further increase the signal-to-noise ratio (SNR) of the novel clips and mitigate these variables, pulse inversion imaging may be employed. Pulse inversion imaging may arise in ultrasound technologies from modeling the relationship between pressure and density in an imaging medium as a Taylor series:

$$P(\rho) = P_0 \frac{\partial P}{\partial \rho}|_{\rho_0}(\rho - \rho_0) + \frac{1}{2}\frac{\partial^2 P}{\partial \rho^2}|_{\rho_0}(\rho - \rho_0)^2 + \dots \tag{1}$$

where P is pressure, and $\rho$ and $\rho_0$ are the time-varying and initial densities, respectively. In this series, the first two partial derivative terms may be of the most interest as they are the highest-magnitude contributions; comparatively, the higher-order terms which follow have only small contributions to the expression. This series can also be further rewritten by re-defining pressure with respect to base pressure $P_0$ by defining $p(\rho)=P(\rho)-P_0$. Condensation $$s = \frac{(\rho - \rho_0)}{\rho_0}$$

is also introduced, alongside parameters A and B, which represent empirically determined coefficients of a given material experiencing the adiabatic pressure changes of an acoustic wave. A and B are composed mathematically of the partial derivatives of P with respect to $\rho$, multiplied by a power of $\rho_0$ to form s. Given these new definitions, Equation 1 may be rewritten as:

$$p(s) = As + \frac{B}{2}s^2. \tag{2}$$

Tissue is a nonlinear medium which can often be modeled, at low pulse energies, as approximately linear, meaning the second term is also assumed to be sufficiently small. In order to model the nonlinearities more clearly, pulse inversion (PI) may be used. In pulse inversion, one image is constructed from two pulses which are identical except for their opposite polarities: if the first pulse is represented by $p_+$ dependent on s, then the second pulse is p–, and p– will be the result of a net opposite change in density $-(\rho-\rho_0)$. Thus, $$s_- = \frac{-(\rho - \rho_0)}{\rho_0} = -s \text{ and } p_+(s) + p_-(s) = As + \frac{B}{2}s^2 + A(-s) + \frac{B}{2}(-s)^2 = Bs^2. \tag{3}$$

When the two pulses are summed together, the linear, first-order response vanishes; conversely, the nonlinear, second-order response will be doubled in magnitude. Other, higher-order terms that were excluded in this analysis will follow a similar pattern of even harmonics doubling and odd harmonics vanishing. Pulse inversion is applicable in this work since the USID circuit of the novel clip uses the incoming imaging pulses as a trigger for the circuit; regardless of the pulse polarity, the response remains the same. Effectively, the USID signal may appear to have behavior more like a second-order response. Furthermore, the imaging pulse energy may be low enough that the majority of the tissue's response may be linear and thus nullified by PI.

Demonstration Methods

A. Generating Sinusoids. The demonstration was performed in three stages, the first of which was to establish the AD9959 evaluation board (from Analog Devices, Inc.) as an appropriate means of generating the USID signal. This board may be configured to generate up to four independent signals on each of its output channels. For the demonstration, this board was configured to generate three pure-tone sinusoids that are comprised by the USID signal. This evaluation board was connected to a 3.3 VDC power source for overall board power, a 1.8 VDC power source for digital logic, and an externally generated reference clock signal provided by a Keysight 33210A arbitrary waveform generator which was set to output a 10 MHz square wave with a 50% duty cycle and an output voltage range between 0 and 1 V. This external reference clock signal facilitated the AD9959 to receive instructions, which could either be PC-driven input from Analog Devices' proprietary test software or commands sent in serial peripheral interface (SPI) protocol from another source such as a microcontroller. Board functionality was first verified using PC control, ensuring all required inputs and outputs were functional. Signals were observed by connecting a BNC-SMA cable directly from the board's filtered channel outputs to an oscilloscope. Next, a summing amplifier was constructed to combine the outputs of multiple channels. Each channel, of the three used in the demonstration, was outfitted with a 1 kΩ resistor into the inverting input on an LM6172 (from Texas Instruments) high speed op-amp, with a 10 kΩ resistor providing the feedback loop between the op-amp output and inputs. Once the summing amplifier functionality was verified with the AD9959 signals, a Teensy 3.2 microcontroller (from PJRC) board was used to control the AD9959, facilitating simulation of an ultrasound triggering mechanism.

B. Teensy Control. Shifting control to the Teensy board involved making adjustments to jumpers on the AD9959 board, and all digital inputs and outputs were now sourced through an onboard 13×2 header instead of the USB cable connector. The Teensy 3.2 was chosen to control the AD9959 for its ability to be powered by a 3.3 V power source and its high clock rate of up to 96 MHz, which would lead to minimal delays incurred due to processing. To interface with the Teensy, the AD9959 used SPI communication protocols. SPI communication with the AD9959 involves first transmitting a two-byte register address followed by the data stored in that register. Register lengths vary, and by default all incoming instructions are interpreted as being part of the addressed register until all of its bits have been written. Less than all registers were addressed, which included those used to initiate external SPI communication, select and program the different channels with sinusoids, and adjust board power-down settings. Other digital inputs not linked to chip registers augmented the information stored on the board, such as by triggering the board to save input changes and resetting the chip's programming to default values. To test the Teensy-controlled board configuration, the same tests as were used for PC control were adapted into SPI, with the goal of generating pure tone sinusoids at three different frequencies on multiple channels simultaneously.

C. Circuit Triggering. To trial the ultrasound-triggering mechanism, a controlled electrical logic signal was used. This signal, generated externally, was supplied to a Teensy pin by physically reconnecting wires and observing the summing amplifier output. Under correct operation, logic HIGH may cause the board to enable, outputting signals at the initially-coded frequencies. Logic LOW may cause the board to enter into power-down mode, preserving the register information while disabling output. This quick-recovery mode allowed the delay between triggering and signal output to be minimal. Once manually-triggered operation was achieved, the setup was expanded to include piezoelectric elements that transmitted and received pulses. In this setup, two microcrystals (from Sonometrics) were added to the breadboard that included the Teensy and its inputs. In the intended circuit design for a completed end-user or commercial novel USID clip, there may be a single piezoelectric element with input and output controlled by a switch, but the setup with two elements as used in this test circuit facilitated greater detail in system evaluation and debugging. The two crystals, denoted receive (RX) and transmit (TX), handled the two directions of communication between a single element transducer (e.g., 2.5 MHz center frequency, f #2). The RX crystal's output was supplied to a Panametrics 5800 signal amplifier before being connected into the breadboard, while the TX crystal signal was transmitted directly from the board without any intermediate processing. This setup with the two crystals and a single element transducer was submerged into a water tank. The transducer's output was also connected to amplification from a Panametrics 5900 before being displayed on an oscilloscope. This setup had some shortcomings in terms of the ability to synchronize the transducer pulse and the TX crystal output on the chosen oscilloscope, so a SYNC signal from the Panametrics 5900 was used as a signal to the Teensy to inform it of an incoming pulse. In this way, the transducer's and the two crystals' signals may be observed synchronously on one oscilloscope to verify that the triggering was operating appropriately. Additionally, the ability to alter the output energy from the transducer was somewhat limited, and the RX signal was not powerful enough to trigger a logical change that may be used by an interrupt routine in the Teensy's code. This was resolved by using a threshold system to read an analog baseline noise value after the SYNC signal was received, waiting a set amount of time for the expected pulse to arrive, and then reading an analog value again during the pulse. The two analog read values were then compared, and if this result was above a set threshold, the TX signal would be transmitted. In practice, this type of logic scheme would not be desirable because it also includes a process of being tuned to a specific depth. The tuning issue was quickly eliminated when the USID clip system was revised for compatibility with a linear array probe and its ultrasound imaging system. To facilitate B-mode scans with an ultrasound imaging system, the microcontroller code was again revised. The ultrasound imaging system used a Verasonics research system with a C5-2 probe attached, and provided better resolution and contrast limits and more control over input voltage. Along with the fact that visualization no longer depended upon syncing on one oscilloscope, this meant that the SYNC signal and coded timing aspects may be eliminated in favor of an interrupt routine dependent on the imaging pulse. In this setup, the RX crystal input, e.g., now from the imaging probe, was still amplified by the Panametrics 5800. Calculating the spectrum of the USID signal output was achieved by adding a new function process to the configuration code for the Verasonics system. In this code, the received RF data from the probe was windowed both axially and laterally to the approximate location of the signal; the lines were averaged laterally and the resulting vector of averaged RF values was visualized as a power spectral density in the frequency domain. This routine ran continuously within the acquisition period, with the spectrum updating in real time.

D. Pulse Inversion. Lastly, alterations were made to the processing on the Verasonics system to facilitate pulse inversion imaging. This system comes pre-equipped with several example code sets; the example code to perform pulse inversion was altered to be compatible with the C5-2 probe and also to display a live visualization of the frequency spectrum alongside the B-mode data. Data was again location-windowed. For this code, however, acquisitions in time, e.g., the two different pulse polarities, were collected into one longer data stream than was used for the earlier B-mode imaging. More precise windowing of the static setup was performed to correctly capture both responses in the pair. However, once these two windows were summed, frequency was still visualized in much the same way as before. This information, alongside the PI B-mode images, enabled visualization of correct operation, ON and OFF states, and the effect of changing frequencies and pulse weighting on the system.

Demonstration Results

The AD9959 may generate a wide range of signals, from approximately 2.33 mHz to over 100 MHz, so the limiting factor in choosing the frequencies for the USID bits was the overlap between the bandwidth of the sonomicrocrystals and the C5-2 probe. The crystals had a center frequency around 1 MHz with acceptable bandwidth up to 3 MHz. The probe's lower bandwidth limit was 2 MHz, so the region between 2 and 3 MHz was chosen to host the USID bits. Many frequencies were tested in and outside this range, but 2, 2.5, and 3 MHz were ultimately chosen to carry the USID bits in this setup. Numbering convention for identifying each of the bits was determined left-to-right, much as the spectra would be read, so the most significant bit was indicated by the 2 MHz signal and the least significant bit by the 3 MHz signal.

The TX crystal output was successfully visualized and was verified to be dependent on the receipt of an amplified incoming pulse by the RX crystal.

Figure 9:
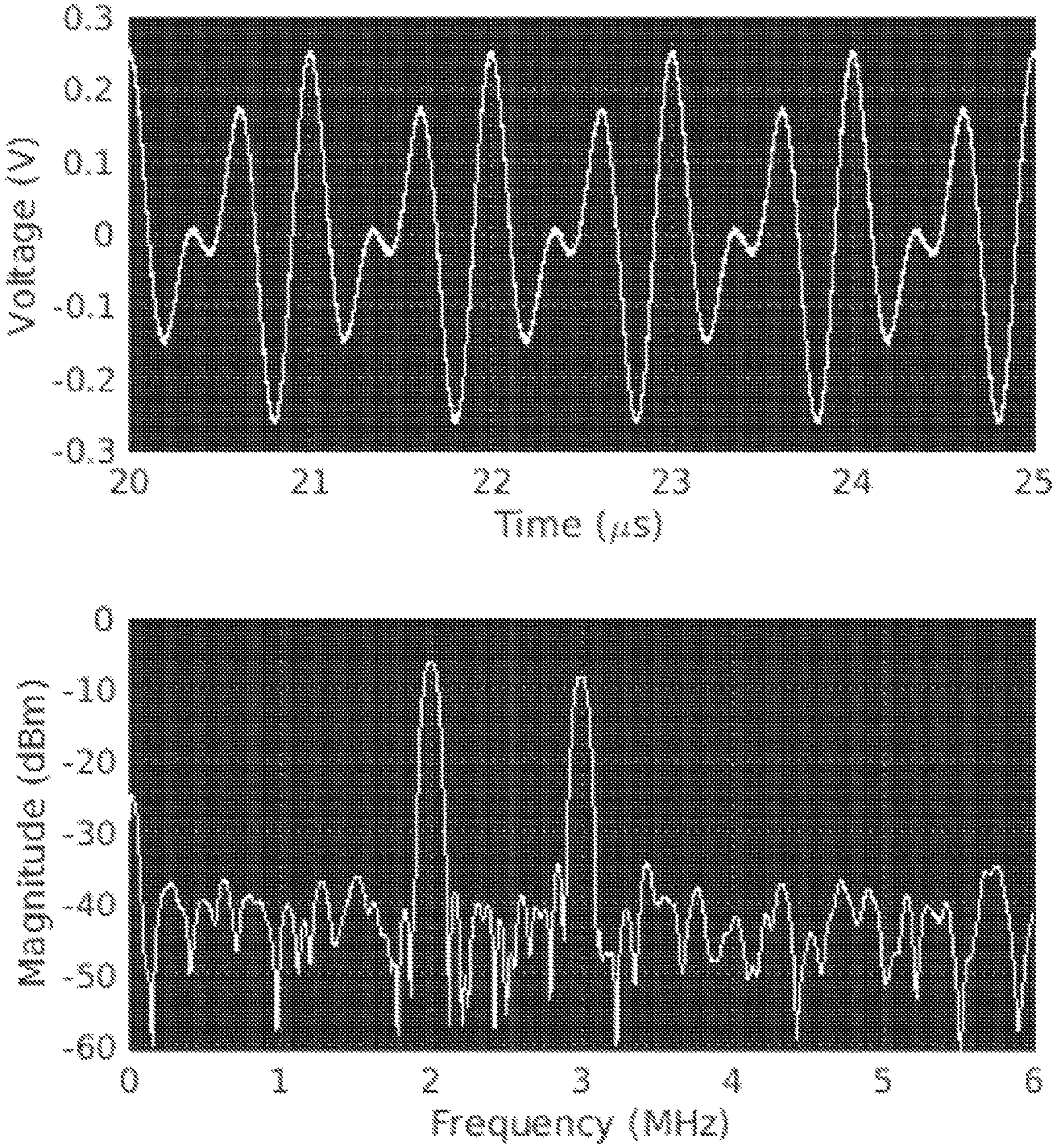
FIG. 9 is a graph illustrating a transmitted signal (ID 5) in both Time and Frequency domains.

FIG. 9 is a graph illustrating a transmitted signal (ID 5) in both Time and Frequency domains. The spectrum was calculated from a 40 μs window of the signal. A 5 μs portion of the 50 μs outgoing USID signal is shown in FIG. 9. The nature of the wave as a composite of two sinusoids is apparent, and the two frequency components are visible at approximately 30 dBm above the noise in this visualization. The data in FIG. 9 was obtained with the triggering dependence removed to more clearly visualize the spectrum. When the crystal system was imaged under ultrasound, it showed strong responsiveness to the imaging pulse, with USID signal visible as a trail behind the TX crystal when active.

Figure 10A:
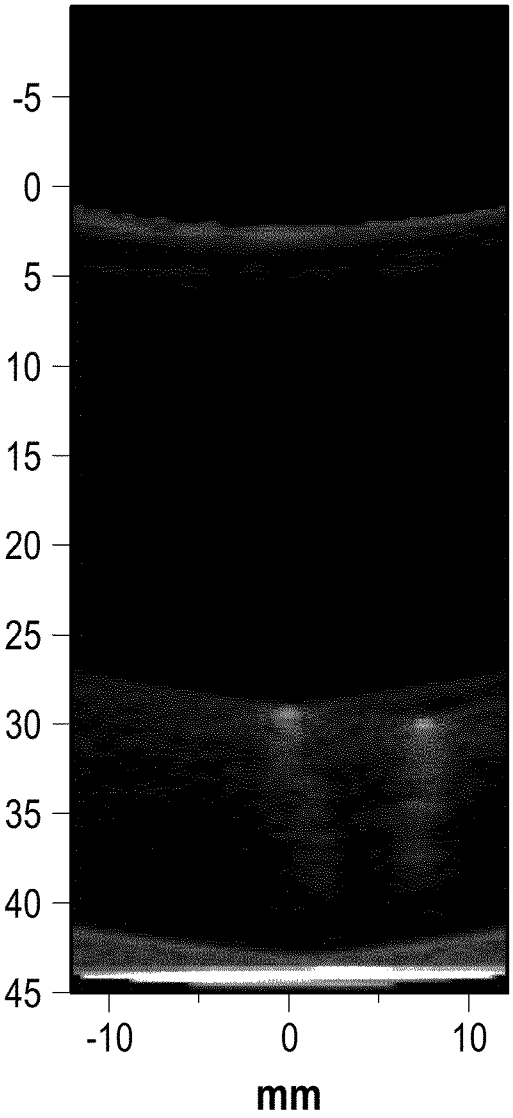
FIG. 10A illustrates a B-mode image of the exemplary two-crystal setup with the USID system inactive.
Figure 10B:
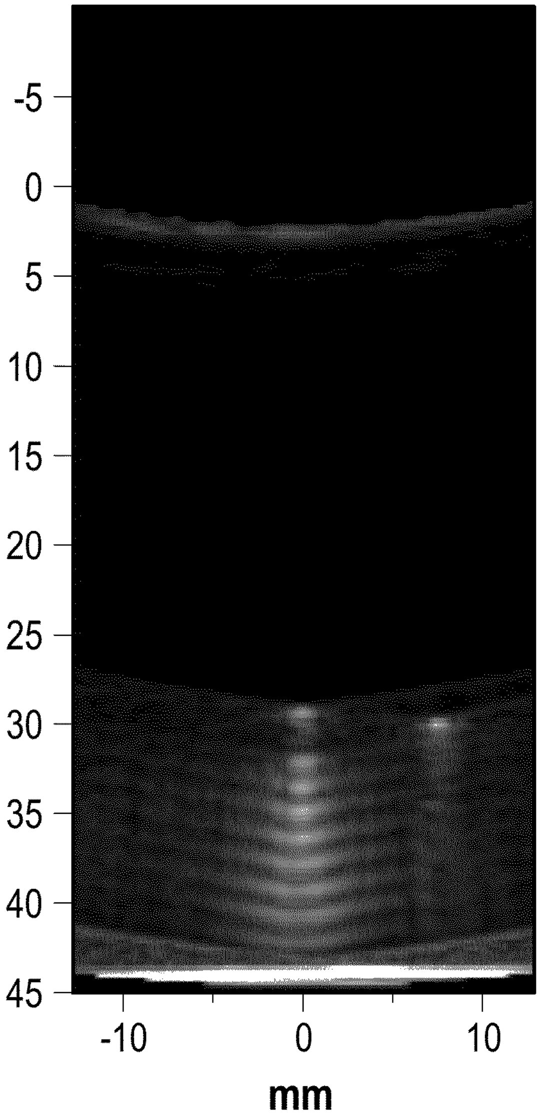
FIG. 10B illustrates a B-mode image of the exemplary two-crystal setup with the USID system active.

FIG. 10A illustrates a B-mode image of the exemplary two-crystal setup with the USID system inactive. FIG. 10B illustrates a B-mode image of the exemplary two-crystal setup with the USID system active. FIGS. 10A and 10B reflect a system in which the TX crystal is at a lateral position 0 mm. FIGS. 10A and 10B show the difference in B-mode imaging between the inactive (FIG. 10A) and active (FIG. 10B) circuit. The system was found to respond when a probe voltage of 4.0 V minimum was used, given amplification of the RX signal by the Panametrics 5800 to a gain of 60 dB and attenuation of 10 dB. The large amplification may be due, in part, to the method used to code the USID triggering, which relies upon a digital change on 3.3 V logic being recognized.

Figure 11A:
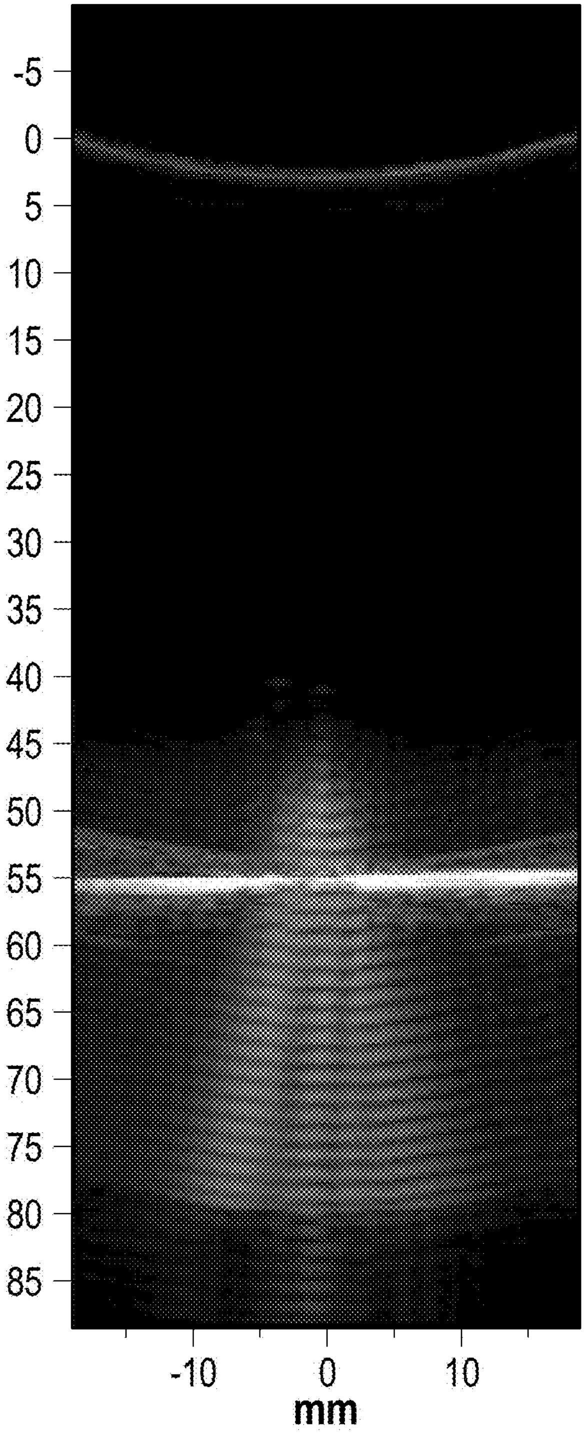
FIGS. 11A and 11B are exemplary B-mode images of the crystal and USID signal using the same settings under standard imaging (FIG. 11A) and pulse inversion with equally weighted pulses (FIG. 11B).
Figure 11B:
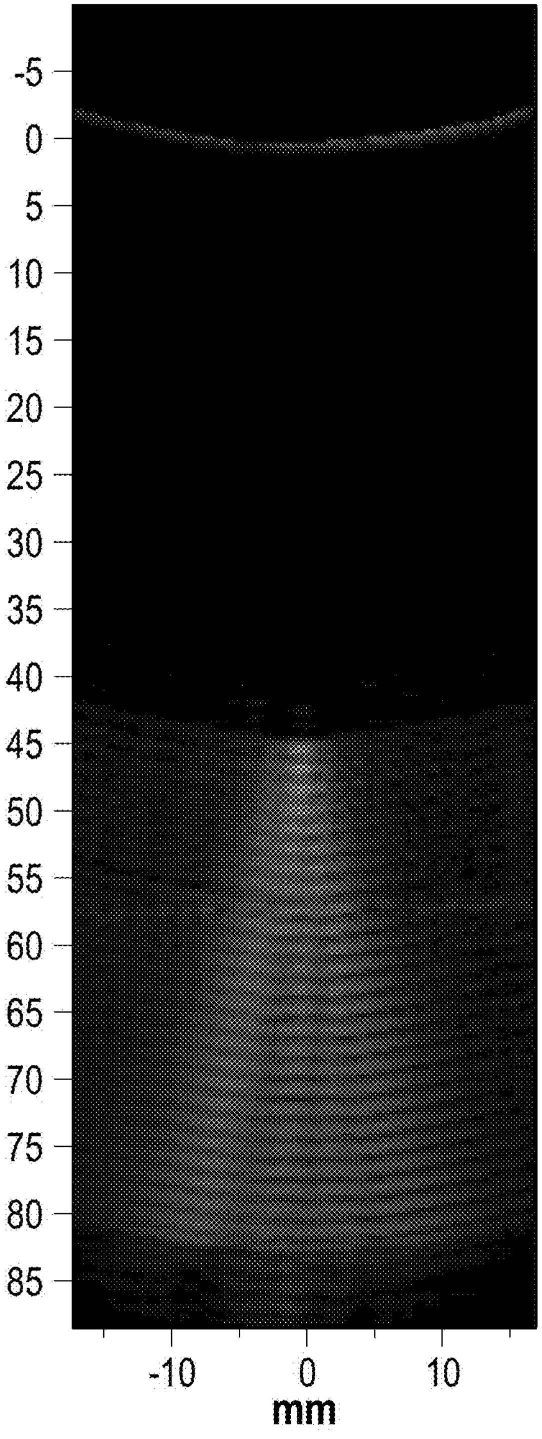

FIGS. 11A and 11B are exemplary B-mode images of the crystal and USID signal using the same settings under standard imaging (FIG. 11A) and pulse inversion (PI) with equally weighted pulses (FIG. 11B). Pulse inversion provided further isolation of the clip signal, eliminating the appearance of the crystal itself and lowering the visibility of the bottom of the water tank while leaving the USID signal intact as seen in FIGS. 11A (no PI) and 11B (with PI). The ability of the USID signal to persist under pulse inversion as demonstrated may allow for accurate automated isolation in a noisier tissue environment.

Figure 12:
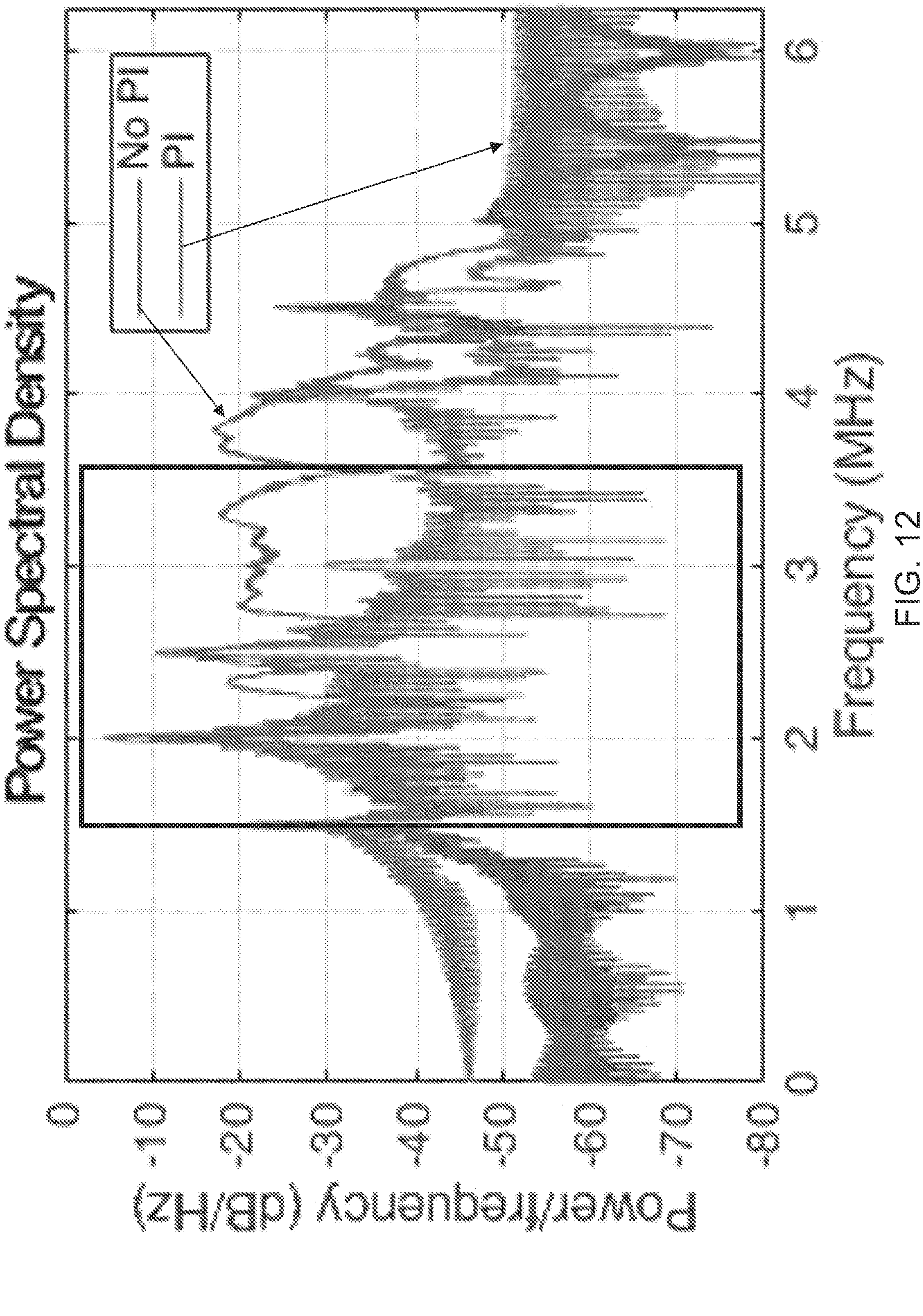
FIG. 12 is an exemplary power spectral density graph illustrating the frequency spectra obtained for the USID signals shown in FIGS. 11A and 11B.

FIG. 12 is an exemplary power spectral density graph illustrating the frequency spectra obtained for the USID signals shown in FIGS. 11A (no PI) and 11B (with PI). Visualizations of the spectra in FIG. 12 corresponding to the USID signal in FIGS. 11A and 11B benefit from the improved contrast provided by pulse inversion. Using pulse inversion, the fundamental response from the probe itself is reduced, particularly in the region between 2.5 and 4 MHz. Reductions in system noise such as this may improve the accuracy of clip identification from the isolated signal.

FIGS. 13A, 13B, 13C, 13D, 13E, and 13F are exemplary power spectral density graphs of USID clips having IDs 1-6, respectively, as determined by their spectral content, including comparisons between the transmitted signal and the signal obtained from pulse inversion (PI) on the Verasonics system. In total, 6 of the 7 different USID signals proposed were able to be visualized clearly. Each of the obtained USID signals is shown in FIGS. 13A-13F: this data represents both the spectra of the transmitted signal (dotted curves) from the TX crystal and the spectra as received by the Verasonics system after pulse inversion (solid curve). The seventh signal required signals from 3 channels of the AD9959 to work, but two of the four channels were found to be faulty at this point in the experiment and this signal could therefore not be generated.

Figure 13A:
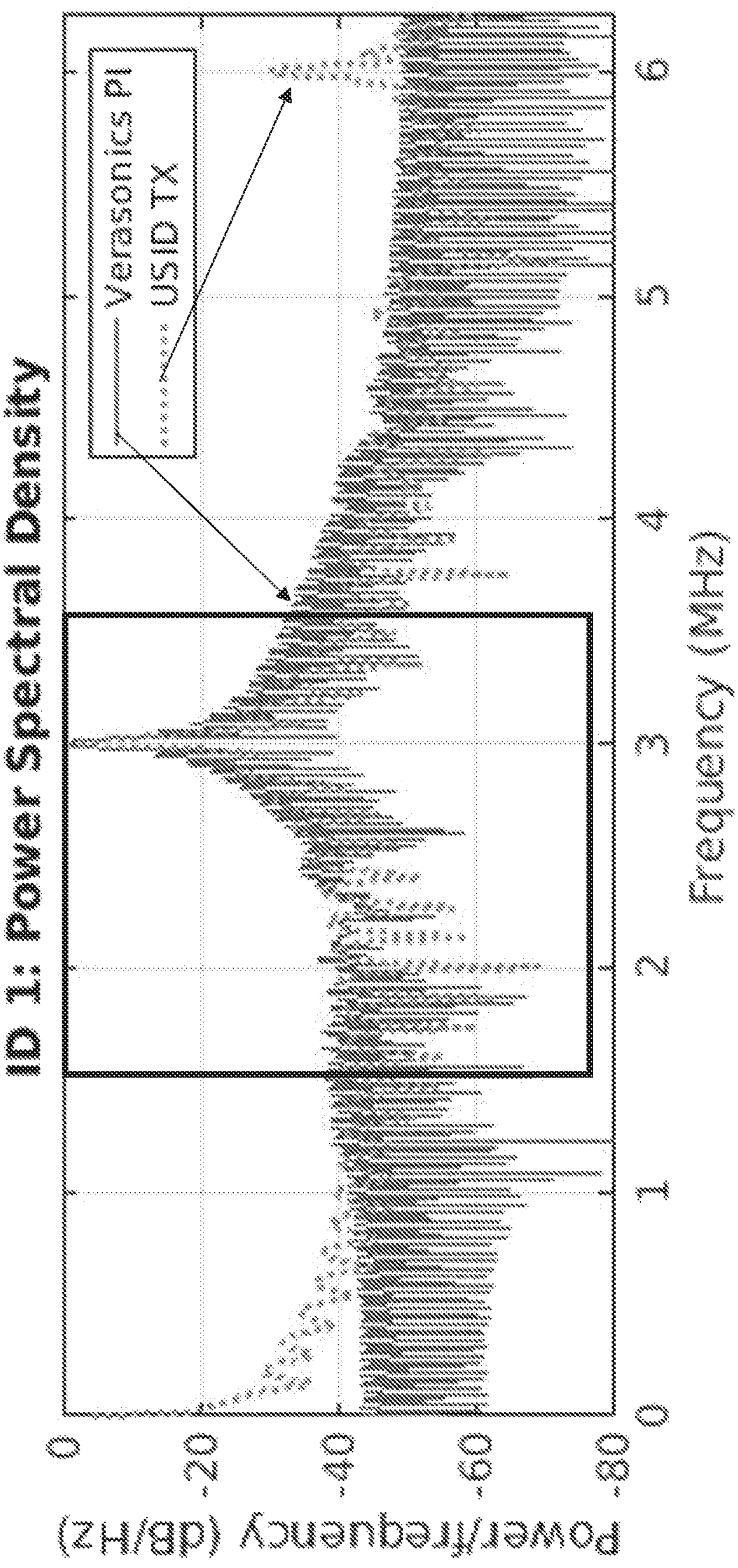
FIGS. 13A, 13B, 13C, 13D, 13E, and 13F are exemplary power spectral density graphs of USID clips having IDs 1-6, respectively, as determined by their spectral content, including comparisons between the transmitted signal and the signal obtained from pulse inversion (PI) on the Verasonics system.
Figure 13B:
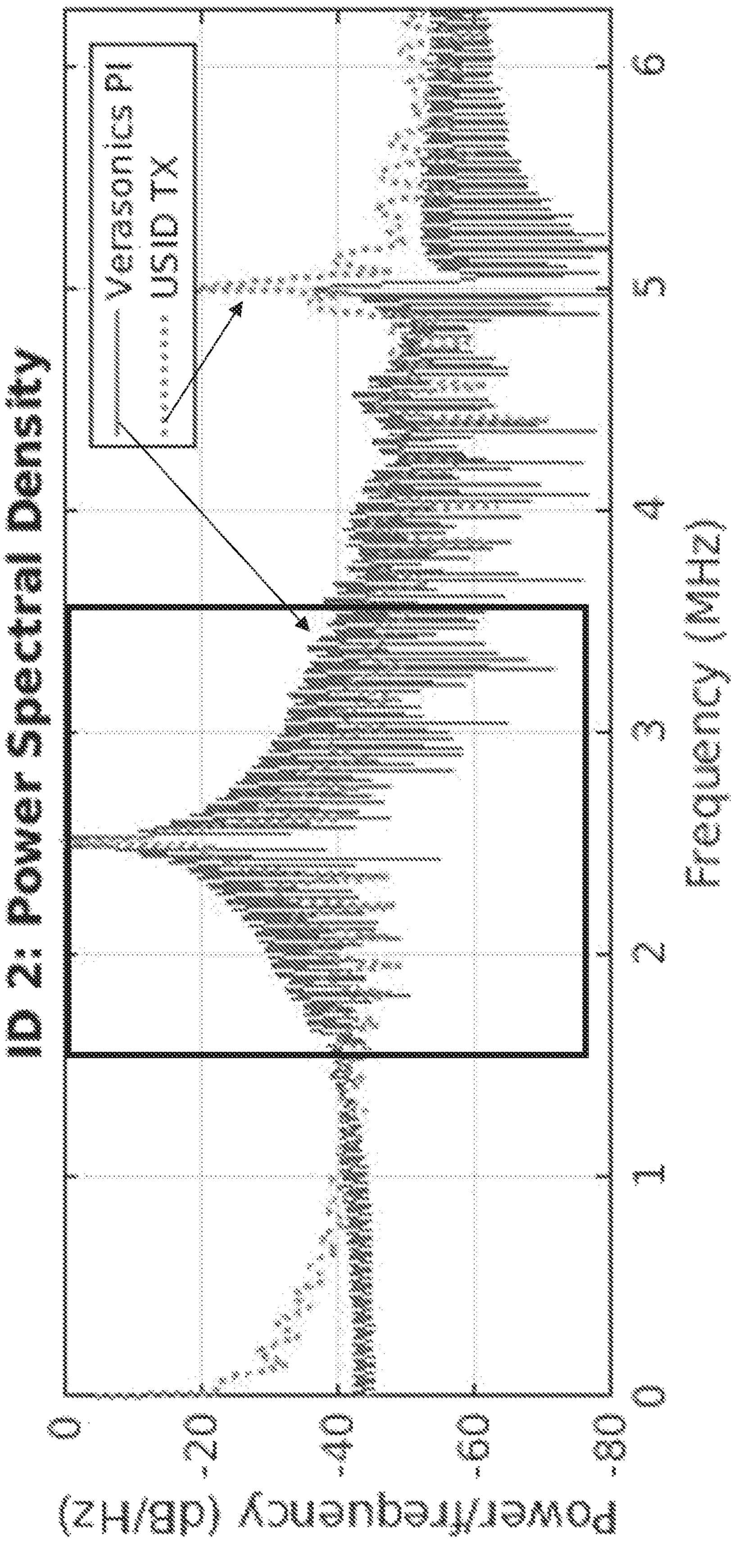
Figure 13C:
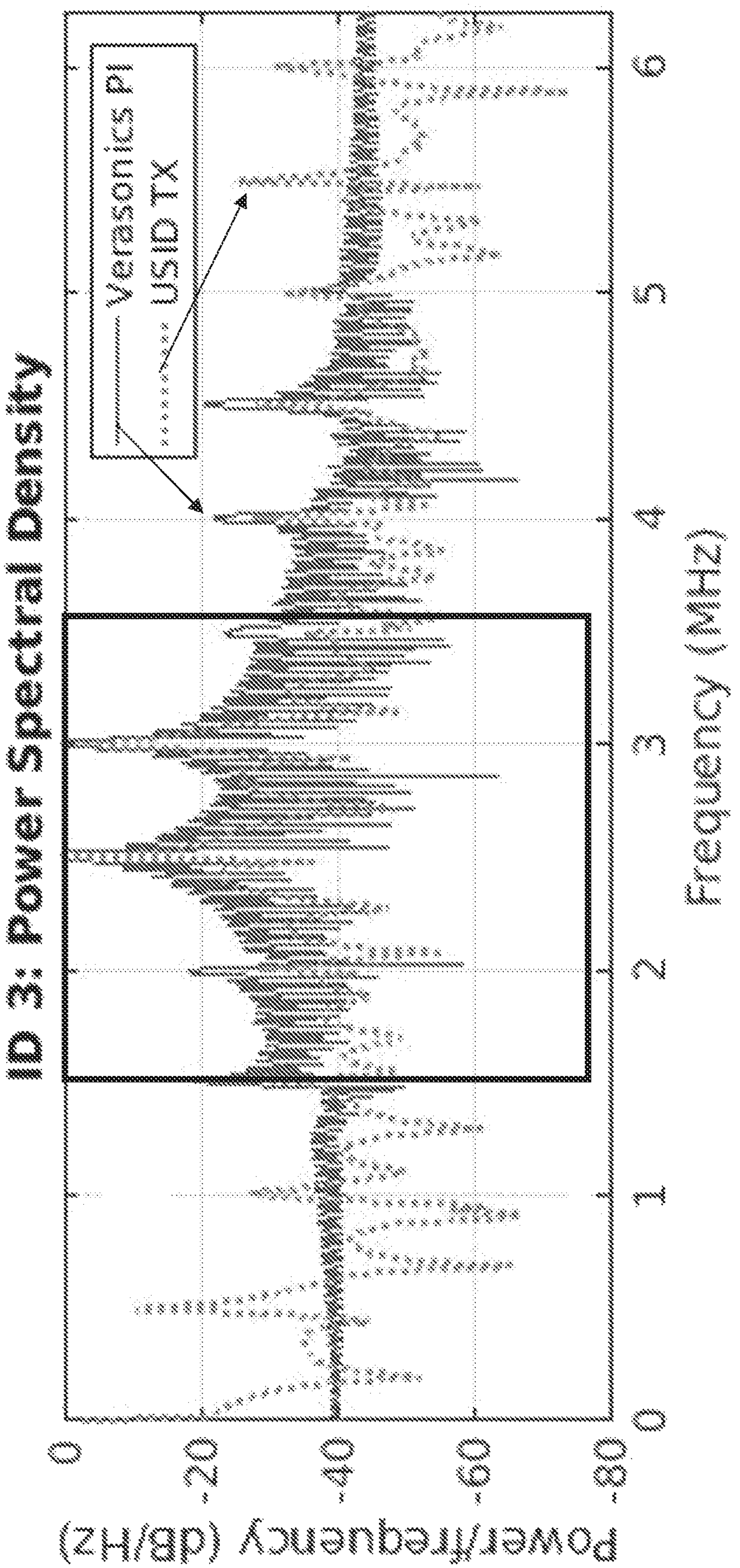
Figure 13D:
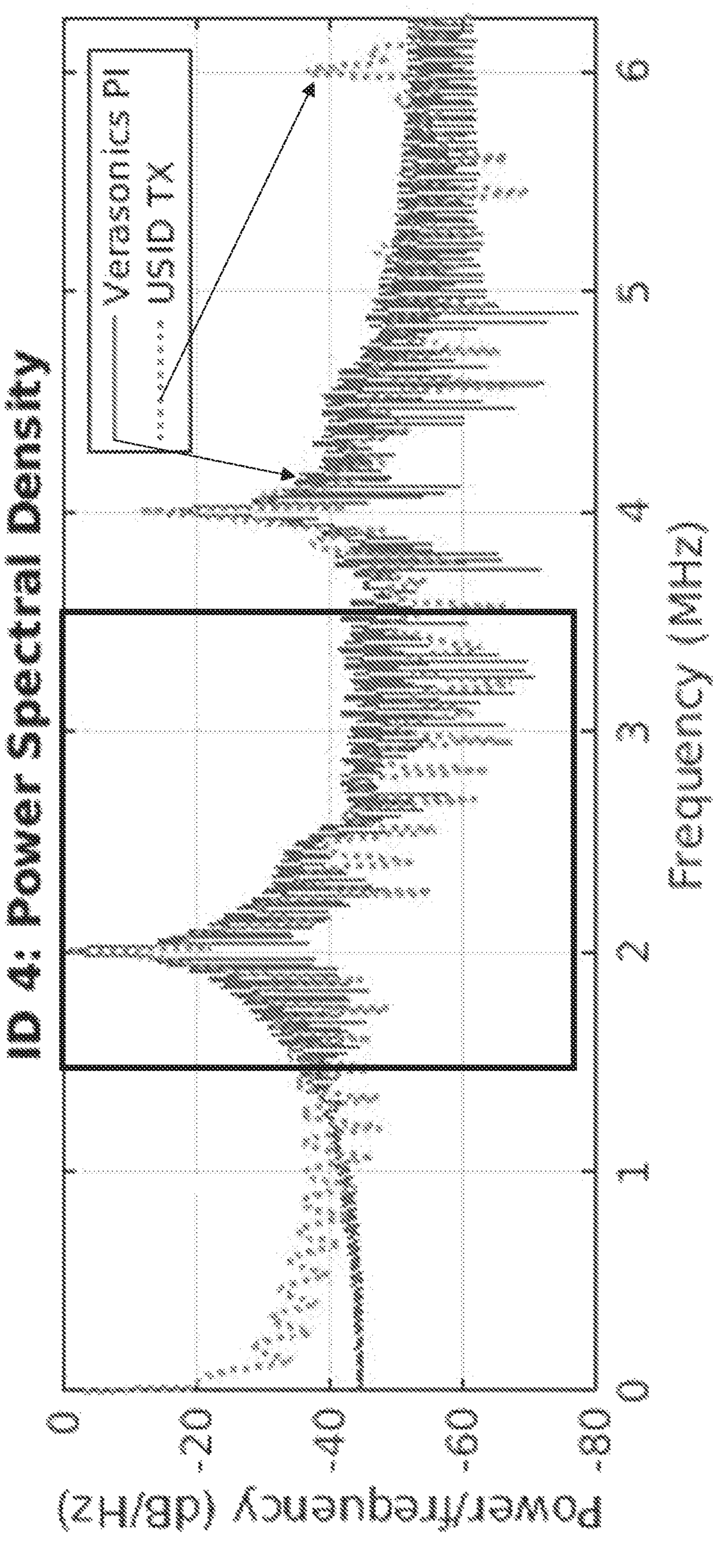
Figure 13E:
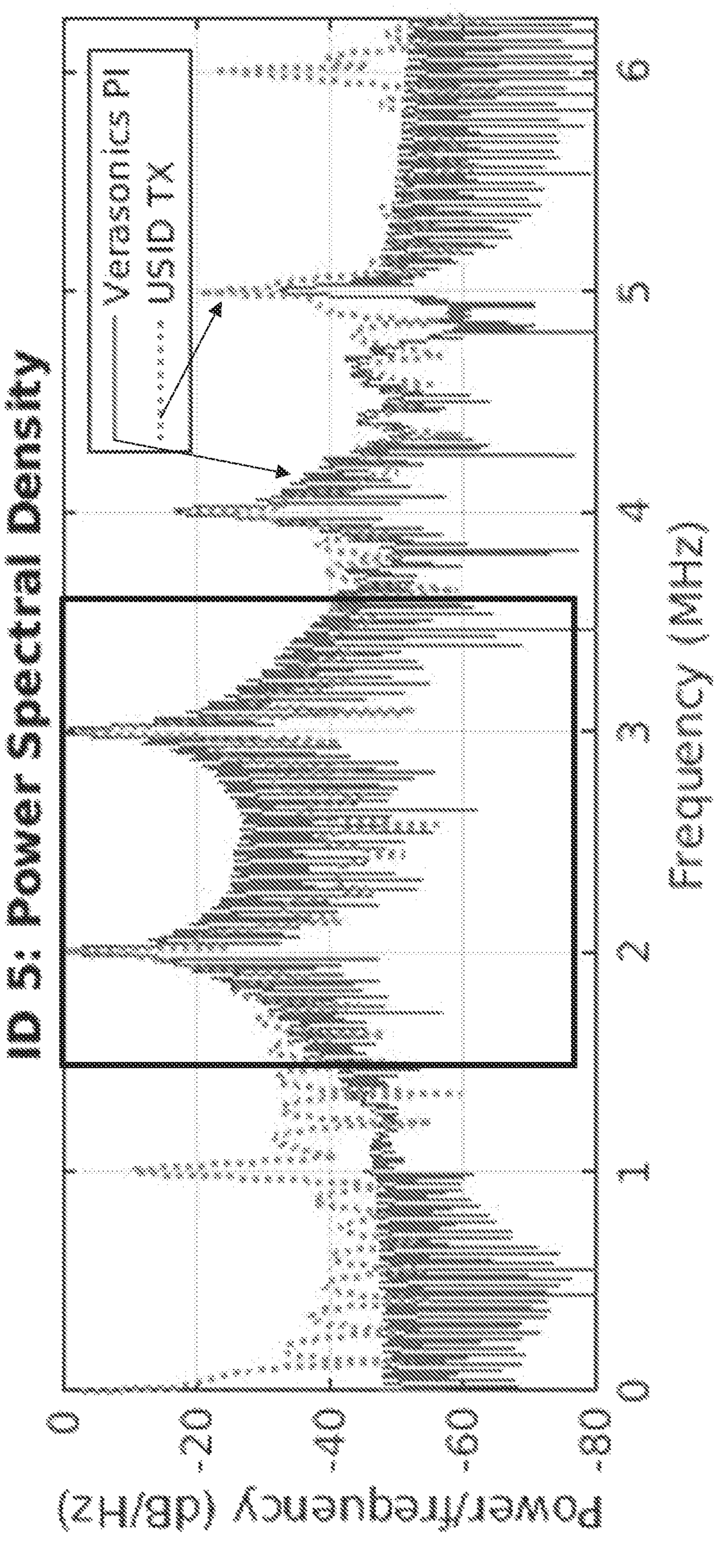

It was also found that nonlinear effects in the generated signal produced harmonics, which can also be seen in FIGS. 13A-13F. In some cases, such as for ID 2 as shown in FIG. 13B, this harmonic is filtered out by either the bandwidth of the crystal or the receiving probe. In other cases, such as with ID 5 as shown in FIG. 13E, the second harmonic of the 2 MHz component remains prominent on receipt and can be easily located within the spectrum. As such, care should be taken in choosing component frequencies such that they are not harmonics of one another for ease of identification. Ideally, the component signals should all be less than $2f_0$, where $f_0$ is the lowest of the component frequencies; this will allow any signal larger than $f_2$, the highest component frequency, to be filtered or ignored when labeling the USID signal.

Figure 13F:
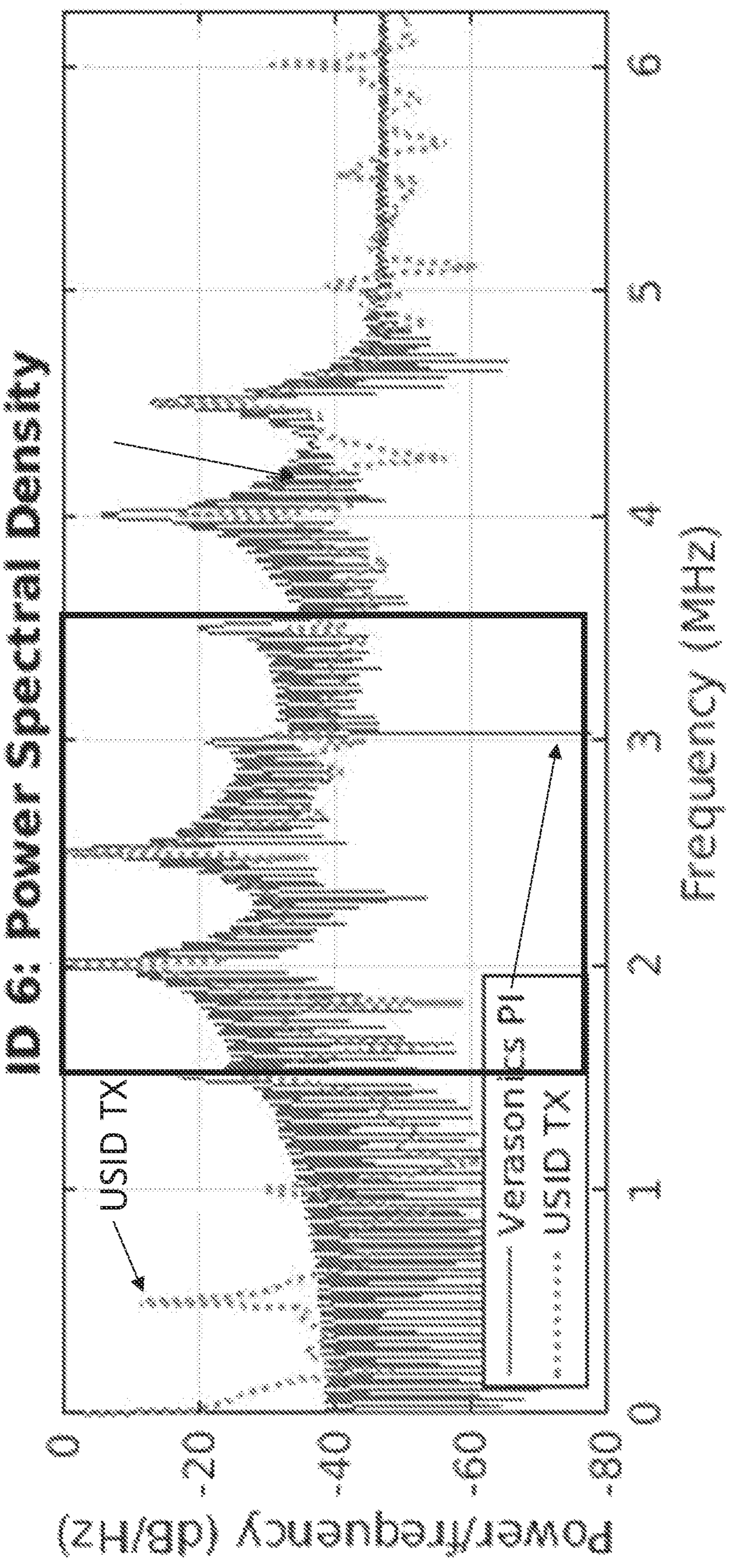

In the spectra shown, the ID signals remain prominent even against their harmonics; in all cases except for ID 6, as shown in FIG. 13F, there was nearly 20 dB of difference between the USID signal's fundamental frequencies and the most prominent harmonic. If signals retain similar behavior in tissue, determination of the ID number can be obtained through simple means such as by setting a threshold.

It should be noted that the real-time spectrum could be highly variable, depending on the stability of the wires in the circuit, and it was not always possible to clearly see the USID signal components in a single frozen capture. This suggests that in future work, it might be more valuable to average multiple acquisition's spectra together before attempting to determine the transmitted ID. The drop in frame rate incurred by this process would most likely be of minimal impact to a system operator but would improve localization and identification accuracy.

CONCLUSION

This work demonstrates that a USID signal, which encodes identification information via combinations of spectral pulses, can be successfully localized and identified in water. The generation of such a signal can be triggered via insonification by an ultrasound system probe whose bandwidth overlaps with the USID source's frequencies. The tissue environment, being considerably more complex than water, will most likely require the use of PI imaging to properly isolate the USID signal: PI has been shown to be able to preserve the USID signal while reducing that of the tissue background. Thus, PI can be used to improve localization accuracy in a sufficiently linear environment. The basic construction of the clip leveraging the USID signal was also found to trigger by ultrasound and remain idle when no pulse was present, reaffirming that the proposed device can, from an electronic standpoint, be constructed. Future work will explore the ability to differentiate between multiple active clips, the effect of attenuators and scatterers on the ability to trigger and receive the USID signal, and the construction of electronics which move away from the AD9959 board and toward the use of oscillators and other electronic components that may be used for an implantable clip design. In addition, code will be created to allow the USID signal to automatically be accurately localized and identified in real-time.

In one aspect, a method may be an operation, an instruction, or a function and vice versa. In one aspect, a clause or a claim may be amended to include some or all of the words (e.g., instructions, operations, functions, or components) recited in other one or more clauses, one or more words, one or more sentences, one or more phrases, one or more paragraphs, and/or one or more claims.

To illustrate the interchangeability of hardware and software, items such as the various illustrative blocks, modules, components, methods, operations, instructions, and algorithms have been described generally in terms of their functionality. Whether such functionality is implemented as hardware, software, or a combination of hardware and software depends upon the particular application and design constraints imposed on the overall system in an application. Skilled artisans may implement the described functionality in varying ways for each particular application.

As used herein, the phrase "at least one of" preceding a series of items, with the terms "and" or "or" to separate any of the items, modifies the list as a whole, rather than each member of the list (e.g., each item). The phrase "at least one of" does not require selection of at least one item; rather, the phrase allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

The word "exemplary" is used herein to mean "serving as an example, instance, or illustration." Any embodiment described herein as "exemplary" is not necessarily to be construed as preferred or advantageous over other embodiments. Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A reference to an element in the singular is not intended to mean "one and only one" unless specifically stated, but rather "one or more." The term "some" refers to one or more. Underlined and/or italicized headings and subheadings are used for convenience only, do not limit the subject technology, and are not referred to in connection with the interpretation of the description of the subject technology. Relational terms such as first and second and the like may be used to distinguish one entity or action from another without necessarily requiring or implying any actual such relationship or order between such entities or actions. All structural and functional equivalents to the elements of the various configurations described throughout this disclosure that are known or later come to be known to those of ordinary skill in the art are expressly incorporated herein by reference and intended to be encompassed by the subject technology. Moreover, nothing disclosed herein is intended to be dedicated to the public regardless of whether such disclosure is explicitly recited in the above description. No claim element is to be construed under the provisions of 35 U.S.C. § 112, sixth paragraph, unless the element is expressly recited using the phrase "means for" or, in the case of a method claim, the element is recited using the phrase "step for."

While this specification contains many specifics, these should not be construed as limitations on the scope of what may be claimed, but rather as descriptions of particular implementations of the subject matter. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination.

The subject matter of this specification has been described in terms of particular aspects, but other aspects may be implemented and shall be within the scope of any claims submitted in this application. For example, while operations are depicted in the drawings in a particular order, this should not be understood as requiring that such operations be performed in the particular order shown or in sequential order, or that all illustrated operations be performed, to achieve desirable results. The actions recited in claims submitted in this application may be performed in a different order and still achieve desirable results. As one example, the processes depicted in the accompanying figures do not necessarily require the particular order shown, or sequential order, to achieve desirable results. In certain circumstances, multitasking and parallel processing may be advantageous. Moreover, the separation of various system components in the aspects described above should not be understood as requiring such separation in all aspects, and it should be understood that the described program components and systems can generally be integrated together in a single software product or packaged into multiple software products.

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of any claims. In addition, in the detailed description, it can be seen that the description provides illustrative examples and the various features are grouped together in various implementations for the purpose of streamlining the disclosure. The method of disclosure is not to be interpreted as reflecting an intention that any claimed subject matter requires more features than are expressly recited in each claim. Rather, as the claims shall reflect, inventive subject matter lies in less than all features of a single disclosed configuration or operation. Any claims shall be incorporated into the detailed description, with each claim standing on its own as a separately claimed subject matter.

Claims shall not be intended to be limited to the aspects described herein, but are to be accorded the full scope consistent with the language of such claims and to encompass all legal equivalents. Notwithstanding, claims shall not be intended to embrace subject matter that fails to satisfy the requirements of the applicable patent law, nor should they be interpreted in such a way.

REFERENCES

[Akk19] Akkus Z, Cai J, Boonrod A, Zeinoddini A, Weston A D, Philbrick K A, Erickson B J. A Survey of Deep- Learning Applications in Ultrasound: Artificial Intelligence-Powered Ultrasound for Improving Clinical Workflow. J Am Coll Radiol. 2019 September; 16(9 Pt B):1318-1328. doi: 10.1016/j.jacr.2019.06.004. PubMed PMID: 31492410.

[Alv06] Alvarez, Soledad, et al. "Role of sonography in the diagnosis of axillary lymph node metastases in breast cancer: a systematic review." American Journal of Roentgenology 186.5 (2006): 1342-1348.

[And10] J. J. Anderson, M.-T. Herd, M. R. King, A. Haak, Z. T. Hafez, J. Song, M. L. Oelze, E. L. Madsen, J. A. Zagzebski, W. D. O'Brien, Jr. and T. J. Hall. Interlaboratory Comparison of Backscatter Coefficient Estimates for Tissue-mimicking Phantoms. Ultrasonic Imaging, 32, 48-64, 2010.

[Ash10] Ashikaga, T., et al. "National Surgical Adjuvant Breast, Bowel Project. Morbidity results from the NSABP B-32 trial comparing sentinel lymph node dissection versus axillary dissection." J Surg Oncol 102.2 (2010): 111-118.

[Azi16] Azizi, Ghobad, et al. "Shear wave elastography and cervical lymph nodes: predicting malignancy." Ultrasound in medicine & biology 42.6 (2016): 1273-1281.

[Bay18] Bayramoglu, Zuhal, et al. "Diagnostic performances of superb microvascular imaging, shear wave elastography and shape index in pediatric lymph nodes categorization: a comparative study." The British joumal of radiology 91.1087 (2018): 20180129.

[Bed08] Bedi, Deepak G., et al. "Cortical morphologic features of axillary lymph nodes as a predictor of metastasis in breast cancer: in vitro sonographic study." American Journal of Roentgenology 191.3 (2008): 646-652.

[Big08] T. A. Bigelow, B. L. McFarlin, W. D. O'Brien, Jr. and M. L. Oelze. In Vivo Ultrasound Attenuation Slope Estimates for Detecting Cervical Ripening in Rats: Preliminary Results. Journal of the Acoustical Society of America, 123, 1794-1800, 2008. PMCID: PMC2637349 (Also, published in the Mar. 15, 2008 issue of Virtual Journal of Biological Physics Research; http://www.vjbio.org)

[Bla17] Black, Dalliah. "Axillary ultrasound: for all, for none, to diagnose positive nodes, or to support avoiding sentinel lymph node biopsy altogether." Annals of surgical oncology 24.1 (2017): 64-69.

[Bou13] Boughey, Judy C., et al. "Sentinel lymph node surgery after neoadjuvant chemotherapy in patients with node-positive breast cancer: the ACOSOG Z1071 (Alliance) clinical trial." Jama 310.14 (2013): 1455-1461.

[Bou14] Bourke, Anita Geraldine, Prasant Peter, and Chaitra Lesli Jose. "The disappearing clip: an unusual complication in MRI biopsy." Case Reports 2014 (2014).

[Bou16] Boughey, Judy C., et al. "Identification and resection of the clipped node decreases the false negative rate of sentinel lymph node surgery in patients presenting with node positive breast cancer (T0-T4, N1-2) who receive neoadjuvant chemotherapy-results from ACOSOG Z1071 (Alliance)." Annals of surgery 263.4 (2016): 802.

[Bou19] Boutrand, Jean-Pierre, ed. Biocompatibility and performance of medical devices. Woodhead Publishing, 2019.

[Bra18] Brattain L J, Telfer B A, Dhyani M, Grajo J R, Samir A E. Machine learning for medical ultrasound: status, methods, and future opportunities. Abdom Radiol (NY). 2018 April; 43(4):786-799. doi: 10.1007/s00261-018-1517-0. PMID: 29492605; PMCID: PMC5886811.

[Bre01] Breiman L. Random forests. Machine Learning, 45(1): 5-32, 2001.

[Bri16] Brierley, James D., Mary K. Gospodarowicz, and Christian Wittekind, eds. TNM classification of malignant tumours. John Wiley & Sons, 2016.

[Byr16] Byra M, Nowicki A, Wróblewska-Piotrzkowska H, Dobruch-Sobczak K. Classification of breast lesions using segmented quantitative ultrasound maps of homodyned K distribution parameters. Medical Physics 43, 10: 5561-5569, 2016.

[Bur97] Burbank, Fred, and Nancy Forcier. "Tissue marking clip for stereotactic breast biopsy: initial placement accuracy, long-term stability, and usefulness as a guide for wire localization." Radiology 205.2 (1997): 407-415.

[Can21] https://seer.cancer.gov/statfacts/html/breast.html (Last visited 2/9/2021)

[Car89] Carter, Christine L., Carol Allen, and Donald E. Henson. "Relation of tumor size, lymph node status, and survival in 24,740 breast cancer cases." Cancer 63.1 (1989): 181-187.

[Cau15] Caudle, Abigail S., et al. "Selective surgical localization of axillary lymph nodes containing metastases in patients with breast cancer: a prospective feasibility trial." JAMA surgery 150.2 (2015): 137-143

[Cau16] Caudle, Abigail S., et al. "Improved axillary evaluation following neoadjuvant therapy for patients with node-positive breast cancer using selective evaluation of clipped nodes: implementation of targeted axillary dissection." Journal of Clinical Oncology 34.10 (2016): 1072.

[Che17] Chen S, Abhinav S, Saurabh S, Abhinav G. Revisting unreasonable effectiveness of data in deep learning era. In: ICCV; 2017. p. 843-52

[Che17] H. Chen, Y. Zhang, M. K. Kalra, F. Lin, Y. Chen, P. Liao, J. Zhou, and G. Wang, "Low-Dose C T With a Residual Encoder-Decoder Convolutional Neural Network," in IEEE Transactions on Medical Imaging, vol. 36, no. 12, pp. 2524-2535, December 2017.

[Che18] Cheng, B., Wei, Y., Shi, H., Chang, S., Xiong, J., Huang, T. S. 2018. Revisiting Pre-training: An Efficient Training Method for Image Classification. arXiv e-prints arXiv:1811.09347

[Chi16] Chiorean, Liliana, et al. "Transcutaneous ultrasound: Elastographic lymph node evaluation. Current clinical applications and literature review." Ultrasound in medicine & biology 42.1 (2016): 16-30.

[Cho18] J. Choo and S. Liu, "Visual Analytics for Explainable Deep Learning" in IEEE Computer Graphics and Applications, vol. 38, no. 04, pp. 84-92, 2018.

[Cho19] Choudhery, Sadia, et al. "Tomosynthesis-guided needle localization of breast and axillary lesions: our initial experience." American Journal of Roentgenology 212.4 (2019): 943-946.

[Coh18] Cohen, T., Freytsis, M. & Ostdiek, B. J. "(Machine) learning to do more with less", High Energ. Phys. (2018) 2018: 34.

[Cor95] C. Cortes and V. Vapnik, "Support-vector networks," Machine Learning, 20 (3): 273-297, 1995.

[Cor12] Coron, Alain, et al. "A quantitative ultrasound-based method and device for reliably guiding pathologists to metastatic regions of dissected lymph nodes." Biomedical Imaging (ISBI), 2012 9th IEEE International Symposium on. IEEE, 2012.

[Cot99] Cote, R. J., et al. "Role of immunohistochemical detection of lymph-node metastases in management of breast cancer." The Lancet 354.9182 (1999): 896-900.

[Cri00] N. Cristianini and J. Shawe-Taylor, "An Introduction to Support Vector Machines and other kernel-based learning methods," Cambridge University Press, 2000.

[Cri13] A. Criminisi and J. Shotton, "Decision Forests for Computer Vision and Medical Image Analysis," Springer 2013.

[Deh17] Mostafa Dehghani, Hamed Zamani, Aliaksei Severyn, Jaap Kamps, and W. Bruce Croft. 2017. Neural Ranking Models with Weak Supervision. In Proceedings of the 40th International ACM SIGIR Conference on Research and Development in Information Retrieval (SIGIR '17). ACM, New York, N Y, USA, 65-74.

[Den15a] Denis M, Mehrmohammadi M, Song P, Meixner D D, Fazzio R T, Pruthi S, Chen S, Fatemi M, Alizad A*, "Comb-push Ultrasound Shear Elastography of Breast Masses: Initial Results Show Promise," PLoS ONE, 10(3): e0119398, 2015.

[Den15b] Denis M, Bayat M, Mehrmohammadi M, Gregory A, Song P, Whaley D H, Pruthi S, Chen S, Fatemi M, Alizad A*, "Update on Breast Cancer Detection Using Comb-push Ultrasound Shear Elastography," IEEE Transactions on Ultrasonics, Ferroelectrics, and Frequency Control, vol. 62, no. 9, pp. 1644-1650, 2015.

[Don18] Dong, Yuhao, et al. "Preoperative prediction of sentinel lymph node metastasis in breast cancer based on radiomics of T2-weighted fat-suppression and diffusion-weighted MRI." European radiology 28.2 (2018): 582-591.

[ElH16] El Hage Chehade H, Headon H, El Tokhy O, et al. Is sentinel lymph node biopsy a viable alternative to complete axillary dissection following neoadjuvant chemotherapy in women with node-positive breast cancer at diagnosis? An updated meta-analysis involving 3,398 patients. Am J Surg 2016; 212(5):969-81.

[Esc17] Hugo Jair Escalante, Sergio Escalera, Isabelle Guyon, Xavier Baró, Yagmur Gugluturk, et al., Explainable and interpretable models in computer vision and machine learning. Springer Verlag, 2018, The Springer Series on Challenges in Machine Learning, 9783319981307. (10.1007/978-3-319-98131-4).

[Far51] J. J. Faran Jr. Sound scattering by solid cylinders and spheres. J. Acoust. Soc. Am., vol. 23, no. 4, pp. 405-418, 1951.

[Fis83] Fisher B, Bauer M, Wickerham L, Redmond C K, Fisher E R. Relation of number of positive axillary nodes to the prognosis of patients with primary breast cancer: an NSABP update. Cancer 1983; 52: 1551-57.

[Fra00] Fraile, M., et al. "Sentinel node biopsy as a practical alternative to axillary lymph node dissection in breast cancer patients: an approach to its validity." Annals of Oncology 11.6 (2000): 701-705.

[Fre14] B. Frenay and M. Verleysen, "Classification in the Presence of Label Noise: A Survey," in IEEE Transactions on Neural Networks and Learning Systems, vol. 25, no. 5, pp. 845-869, May 2014.

[Fri10] Friedman J, Hastie T, Tibshirani R. Regularization Paths for Generalized Linear Models via Coordinate Descent. J Stats Software, 33(1), 1-22, 2010.

[Gee17] Geert L, Thijs K, Babak E B, Arnaud A A S, Francesco C, Mohsen G, Jeroen A W M, van Brain G, Clara I S. A survey on deep learning in medical image analysis. Med Image Anal. 2017; 42:60-88.

[Gen16] Gentile L F, Himmler A, Shaw C M, Bouton A, Vorhis E, Marshall J, et al. Ultrasound-guided segmental mastectomy and excisional biopsy using hydrogel-encapsulated clip localization as an alternative to wire localization. Ann Surg Oncol. 2016; 23(10):3284-9.

[Giu10] Giuliano A E, McCall L, Beitsch P, et al. Locoregional recurrence after sentinel lymph node dissection with or without axillary dissection in patients with sentinel lymph node metastases: the American College of Surgeons Oncology Group Z0011 randomized trial. Ann Surg. 2010; 252:426-32.

[Giu11] Giuliano A E, Hunt K K, Ballman K V, et al. Axillary dissection vs no axillary dissection in women with invasive breast cancer and sentinel node metastasis: a randomized clinical trial. JAMA. 2011; 305:569-75.

[Gon19] Gong P, Song P, Huang C, Fazzio R T, Ruddy K J, Ghosh K, Meixner D D, Ling W*, Chen S, "Ultrasensitive Ultrasound Microvessel Imaging for Characterizing Benign and Malignant Breast Tumors," Ultrasound in Medicine and Biology (in press).

[Guo19] Z. Guo, X. Li, H. Huang, N. Guo and Q. Li, "Deep Learning-Based Image Segmentation on Multimodal Medical Imaging," in IEEE Transactions on Radiation and Plasma Medical Sciences, vol. 3, no. 2, pp. 162-169, March 2019. doi: 10.1 109/TRPMS.2018.2890359.

[Guy03] Guyon, Isabelle, and Andre Elisseeff "An introduction to variable and feature selection." Journal of machine learning research 3. March (2003): 1157-1182.

[Hal09] Halevy A, Norvig P, Pereira F. The unreasonable effectiveness of data. IEEE Intell Syst. 2009; 24:8-12.

[Hal19] Halimu, Chongomweru, Asem Kasem, and S. H. Newaz. "Empirical Comparison of Area under ROC curve (AUC) and Mathew Correlation Coefficient (MCC) for Evaluating Machine Learning Algorithms on Imbalanced Datasets for Binary Classification." Proceedings of the 3rd International Conference on Machine Learning and Soft Computing. ACM, 2019.

[Hou16] L. Hou, D. Samaras, T. M. Kurc, Y. Gao, J. E. Davis and J. H. Saltz, "Patch-Based Convolutional Neural Network for Whole Slide Tissue Image Classification," 2016 IEEE Conference on Computer Vision and Pattern Recognition (CVPR), Las Vegas, NV, 2016, pp. 2424-2433. doi: 10.1109/CVPR.2016.266.

[Hru09] Hruska, David P., and Michael L. Oelze. "Improved parameter estimates based on the homodyned K distribution." IEEE transactions on ultrasonics, ferroelectrics, and frequency control 56.11 (2009).

[Hua19] Huang C, Song P, Gong P, Trzasko J D, Manduca A, Chen S, "Debiasing-based Noise Suppression for Ultrafast Ultrasound Microvessel Imaging," IEEE Transactions on Ultrasonics, Ferroelectrics, and Frequency Control, vol. 66, no. 8, pp. 1281-1291, 2019.

[Hua19b] Huang C, Lowerison M R, Lucien F, Wang D, Gong P, Song P, Chen S, "Noninvasive Contrast-Free 3D Evaluation of Tumor Angiogenesis with Ultrasensitive Ultrasound Microvessel Imaging," Scientific Reports, vol. 9, no. 4907, pp. 1-11, 2019.

[Hyd19] Hyde, Brenda, Jennifer Geske, and Christine Lee. "Challenges to I-125 Seed Localization of Metastatic Axillary Lymph Nodes Following Neoadjuvant Chemotherapy." Journal of Breast Imaging 1.3 (2019): 223-229.

[Jof18] Joffrey L L, Taghi M K, Richard A B, Naeem S. A survey on addressing high-class imbalance in big data. Springer J Big Data. 2018; 5:42.

[Jun15] Jung, Woo Sang, et al. "Shear wave elastography in evaluation of cervical lymph node metastasis of papillary thyroid carcinoma: elasticity index as a prognostic implication." Annals of surgical oncology 22.1 (2015): 111-116.

[Kar14] Karaman, Sinem, and Michael Detmar. "Mechanisms of lymphatic metastasis." The Journal of clinical investigation 124.3 (2014): 922-928.

[Kar16] Karl W, Taghi M K, DingDing W. A survey of transfer learning. J Big Data. 2016; 3:9.

[Kau19] Kaushiki Roy, Debapriya Banik, Debotosh Bhattacharjee, Mita Nasipuri, Patch-based system for Classification of Breast Histology images using deep learning, Computerized Medical Imaging and Graphics, Vol. 71, 2019, pp. 90-103, doi.org/10.1016/j.compmedimag.2018.11.003.

[Kim13] Kim, Soo-Yeon, et al. "US-guided clip implantation for tumor localization in breast cancer patients who undergo neoadjuvant chemotherapy: feasibility study." (2013): 51-58.

[Kin10] M. R. King, J. J. Anderson, M.-T. Herd, D. Ma, A. Haak, L. A. Wirtzfeld, E. L. Madsen, J. A. Zagzebski, M. L. Oelze, T. J. Hall and W. D. O'Brien, Jr. Ultrasonic backscatter coefficients for weakly scattering, agar spheres in agar phantoms. Journal of the Acoustical Society of America, 128, 903-908, 2010.

[LeC15] Y. LeCun, Y. Bengio, and G. Hinton. "Deep learning." Nature 521, no. 7553, pp. 436-444, 2015.

[Lee13] Lee, Eun Jung, et al. "Diagnostic performances of shear wave elastography: which parameter to use in differential diagnosis of solid breast masses?." European radiology 23.7 (2013): 1803-1811.

[Li18] Li, J., Wong, Y., Zhao, Q., Kankanhalli, M. 2018. Learning to Learn from Noisy Labeled Data. arXiv e-prints arXiv:1812.05214.

[Lin05] Ling, Rui, et al. "Lymphatic chemotherapy induces apoptosis in lymph node metastases in a rabbit breast carcinoma model." Journal of drug targeting 13.2 (2005): 137-142.

[Lin15] S. C. Lin, E. Heba, T. Wolfson, B Ang, A. Gamst, A. Han, J. W. Erdman, Jr., W. D. O'Brien, Jr., M. P. Andre, C. B Sirlin and R. Loomba. Noninvasive Diagnosis of Nonalcoholic Fatty Liver Disease and Quantification of Liver Fat using a New Quantitative Ultrasound Technique. Clinical Gastroenterology and Hepatology, 13, 1337-1345, 2015.

[Lit17] Litjens, G., and 8 colleagues 2017. A Survey on Deep Learning in Medical Image Analysis. arXiv e-prints arXiv:1702.05747.

[Liu17] Liu X, Song J L, Wang S H, Zhao J W, Chen Y Q. Learning to Diagnose Cirrhosis with Liver Capsule Guided Ultrasound Image Classification. Sensors 17: 149, 2017.

[Liu18] Liu, K., Li, Y., Xu, N., Natarajan, P. Learn to Combine Modalities in Multimodal Deep Learning. arXiv e-prints arXiv:1805.11730.

[Luc07] Lucci, Anthony, et al. "Surgical complications associated with sentinel lymph node dissection (SLND) plus axillary lymph node dissection compared with SLND alone in the American College of Surgeons Oncology Group Trial Z0011." Journal of Clinical Oncology 25.24 (2007): 3657-3663.

[Lud90] International (Ludwig) Breast Cancer Study Group. Prognostic importance of occult axillary lymph node micrometastases from breast cancers. Lancet 1990; 335: 1565-68.

[Mal8] Ma et al. Ma, X., and 7 colleagues 2018. Dimensionality-Driven Learning with Noisy Labels. In Proceedings of the International Conference on Machine Learning (ICML), 2018.

[Mad05] Madsen, Ernest L., et al. "Tissue-mimicking agar/gelatin materials for use in heterogeneous elastography phantoms." Physics in Medicine & Biology 50.23 (2005): 5597.

[Mak16] Maksuti, Elira, et al. "Arterial stiffness estimation by shear wave elastography: Validation in phantoms with mechanical testing." Ultrasound in medicine & biology 42.1 (2016): 308-321.

[Mal19] Malter, Wolfram, et al. "First reported use of the Faxitron LOCalizer™ Radiofrequency Identification (RFID) system in Europe-A feasibility trial, surgical guide and review for non-palpable breast lesions." in vivo 33.5 (2019): 1559-1564, doi: 10.21873/invivo.11637.

[Mam11] J. Mamou, A. Coron, M. L. Oelze, E. Saegusa-Beecroft, M. Hata, P. Lee, J. Machi, E. Yanagihara, P. Laugier, and E. J. Feleppa, "Three-dimensional high-frequency backscatter and envelope quantification of cancerous human lymph nodes," Ultrasound in Medicine and Biology, 37, 345-357, 2011.

[Mam13] Editors: Mamou J and Oelze M L. "Quantitative Ultrasound in Soft Tissues," Springer, New York, N Y, 2013.

[Man16] Mango, Victoria, et al. "Evaluation of the SAVI SCOUT surgical guidance system for localization and excision of nonpalpable breast lesions: a feasibility study." American Journal of Roentgenology 207.4 (2016): W69-W72.

[Mar10] Marshall, Milton V., et al. "Near-infrared fluorescence imaging in humans with indocyanine green: a review and update." Open surgical oncology journal (Online) 2.2 (2010): 12.

[Moo15] Moorman, A. M., et al. "Pre-operative ultrasonographic evaluation of axillary lymph nodes in breast cancer patients: For which group still of additional value and in which group cause for special attention?." Ultrasound in medicine & biology 41.11 (2015): 2842-2848.

[Mor19] Mon, Naoko, et al. "Perfusion contrast-enhanced ultrasound to predict early lymph-node metastasis in breast cancer." Japanese journal of radiology 37.2 (2019): 145-153.

[Nam11] Nam K, Rosado-Mendez I M, Wirtzfeld L A, Pawlicki A D, Kumar V, Madsen E L, Ghoshal G, Lavarello R J, Oelze M L, Bigelow T A, Zagzebski J A, O'Brien Jr. W D, and Hall T J. Ultrasonic attenuation and backscatter coefficient estimates of rodent-tumor mimicking structures: comparison of results among clinical scanners. Ultrasonic Imaging, 33: 233-250, 2011.

[Nam12] K. Nam, I M. Rosado-Mendez, L. A. Wirtzfeld, V. Kumar, E. L. Madsen, G. Ghoshal, A. D. Pawlicki, M. L. Oelze, R. J. Lavarello, T. A. Bigelow, J. A. Zagzebski, W. D. O'Brien Jr. and T. J. Hall. Cross-imaging system comparison of backscatter coefficient estimates from a tissue-mimicking material. Journal of the Acoustical Society of America, 132, 1319-1324, 2012.

[Nam16] Nam, Hyeonseob, Jung-Woo Ha, and Jeonghee Kim. "Dual attention networks for multimodal reasoning and matching." arXiv preprint arXiv:1611.00471 (2016).

[Nat14] National Comprehensive Cancer Network. NCCN clinical practice guidelines in oncology: breast cancer, version 2. 2014. http://www.nccn.org/. Accessed Nov. 2, 2014.

[Ngi11] Jiquan Ngiam, Aditya Khosla, Mingyu Kim, Juhan Nam, Honglak Lee, and Andrew Y. Ng. 2011. Multimodal deep learning. In Proceedings of the 28th International Conference on International Conference on Machine Learning (ICML'11), Lise Getoor and Tobias Scheffer (Eds.). Omnipress, USA, pp. 689-696.

[Ngu17] T. T. (1) Nguyen, T. J. (1) Hieken, J. C. (1) Boughey, and K. N. (2) Glazebrook, "Localizing the Clipped Node in Patients with Node-Positive Breast Cancer Treated with Neoadjuvant Chemotherapy: Early Learning Experience and Challenges.," Annals of Surgical Oncology, vol. 24, no. 10, pp. 3011-3016, 2017, doi: 10.1245/s10434-017-6023-z.

[Ngu19] Nguyen A., Yosinski J., Clune J. (2019) Understanding Neural Networks via Feature Visualization: A Survey. In: Samek W., Montavon G., Vedaldi A., Hansen L., Muller K R. (eds) Explainable AI: Interpreting, Explaining and Visualizing Deep Learning. Lecture Notes in Computer Science, vol 11700.

[NIBIB19] NIBIB Science Highlights Jun. 10, 2019, "Artificial intelligence enables low-dose C T scans, faster scan time" https://www.nibib.nih.gov/news-events/newsroom/artificial-intelligence-enables-low-dose-ct-scans-faster-scan-time, accessed Sep. 20, 2019.

[Nur05] Nurco J, Mancino A T, Whitacre E, Edwards M J. Surgical benefits conveyed by biopsy site marking system using ultrasound localization. Am J Surg. 2005; 190:618-22.

[Oel02] Oelze M L, Zachary J F and O'Brien, Jr. W D. Characterization of Tissue Microstructure using Ultrasonic Backscatter: Theory and Technique Optimization using a Gaussian Form Factor. Journal of the Acoustical Society of America, 112, 1202-1211, 2002.

[Oel16] Oelze, Michael L., and Jonathan Mamou. "Review of quantitative ultrasound: Envelope statistics and backscatter coefficient imaging and contributions to diagnostic ultrasound." IEEE transactions on ultrasonics, ferroelectrics, and frequency control 63.2 (2016): 336-351.

[Oh18] Oh, Kangrok, et al. "Optimizing between data transformation and parametric weighting for stable binary classification." Journal of the Franklin Institute 355.4 (2018): 1614-1637.

[Ola16] Olah, et al., "Feature Visualization", Distill, 2017. Ribeiro, Marco Tulio et al. "Why should I trust you?: Explaining the predictions of any classifier." SIGKDD 2016.

[Ozc17] Ozcan, Lerna C., and Armando E. Giuliano. "Is Axillary Lymph Node Dissection Necessary After a Positive Sentinel Lymph Node Biopsy?." Advances in surgery 51.1 (2017): 165-178.

[Pai17] Paige, Jeremy S., et al. "A pilot comparative study of quantitative ultrasound, conventional ultrasound, and MRI for predicting histology-determined steatosis grade in adult nonalcoholic fatty liver disease." American Journal of Roentgenology 208.5 (2017): W168-W177.

[Par15] Park, Ah Young, et al. "Shear wave elastography of thyroid nodules for the prediction of malignancy in a large scale study." European journal of radiology 84.3 (2015): 407-412.

[Pen19] Peng A. Y., Sing Koh Y., Riddle P., Pfahringer B. (2019) Using Supervised Pretraining to Improve Generalization of Neural Networks on Binary Classification Problems. In: Berlingerio M., Bonchi F., Gärtner T., Hurley N., Ifrim G. (eds) Machine Learning and Knowledge Discovery in Databases. ECML PKDD 2018. Lecture Notes in Computer Science, vol 11051. Springer.

[Pil16] Pilewskie M, Mautner S K, et al., Does a positive axillary lymph node needle biopsy result predict the need for axillary lymph node dissection in clinically node-negative breast cancer patients in the ACOSOG Z001 Era? Ann Surg Oncol, 2016; 23: 1123-1128.

[Por19] Portnow, Leah H., et al. "Biopsy Marker Standardization: What's in a Name?." American Journal of Roentgenology 212.6 (2019): 1400-1405.

[Qia06] Qian, Chao-Nan, et al. "Preparing the "soil": the primary tumor induces vasculature reorganization in the sentinel lymph node before the arrival of metastatic cancer cells." Cancer research 66.21 (2006): 10365-10376.

[Ramos14] M. Ramos, J. C. Diez, T. Ramos, R. Ruano, M. Sancho, and J. M. Gonzilez-Orns, "Intraoperative ultrasound in conservative surgery for non-palpable breast cancer after neoadjuvant chemotherapy," International Journal of Surgery, vol. 12, no. 6, pp. 572-577, 2014, doi: https://doi.org/10.1016/j.ijsu.2014.04.003.

[Raw17] Rawat W, Wang Z. Deep Convolutional Neural Networks for Image Classification: A Comprehensive Review. Neural Comput. 2017 September; 29(9):2352-2449. doi: 10.1162/NECO_a_00990. Epub 2017 Jun. 9.

[Raz16] Razek, Ahmed Abdel Khalek Abdel, et al. "Assessment of axillary lymph nodes in patients with breast cancer with diffusion-weighted MR imaging in combination with routine and dynamic contrast MR imaging." Breast cancer 23.3 (2016): 525-532.

[Sae13] Saegusa-Beecroft E, Machi J, Mamou J, Hata M, Coron A, Yanagihara E T, Yamaguchi T, Oelze M L, Laugier P, Feleppa E J. Three-dimensional quantitative ultrasound for detecting lymph node metastases. J Surg Res, 183:258-269, 2013.

[Sah04] Saharinen, Pipsa, et al. "Lymphatic vasculature: development, molecular regulation and role in tumor metastasis and inflammation." Trends in immunology 25.7 (2004): 387-395.

[Sak18] Sakamoto, Naomi, et al. "Evaluation of the dislocation and long-term sonographic detectability of a hydrogel-based breast biopsy site marker." Breast Cancer 25.5 (2018): 575-582.

[San15] Sannachi L, H. Tadayyon, A. Sadeghi-Naini, W. Tran, S. Gandhi, F. Wright, M. Oelze and G. Czarnota Non-Invasive Evaluation of Breast Cancer Response to Chemotherapy using Quantitative Ultrasonic Backscatter Parameters. Medical Image Analysis, 20, 224-236, 2015.

[San18] Sannachi L, Gangeh M, Tadayyon H, Sadeghi-Naini A, Gandhi S, Wright F C, Slodkowska E, Curpen B, Tran W, Czarnota G J. Response monitoring of breast cancer patients receiving neoadjuvant chemotherapy using quantitative ultrasound, texture, and molecular features. PLoS One, 3; 13(1): e0189634, 2018.

[Seo18] Seo, Mirinae, and Yu-Mee Sohn. "Differentiation of benign and metastatic axillary lymph nodes in breast cancer: additive value of shear wave elastography to B-mode ultrasound." Clinical imaging 50 (2018): 258-263.

[Sha15] Shao L. Transfer learning for visual categorization: a survey. IEEE Trans Neural Netw Learn Syst. 2015; 26(5):1019-34.

[Sha18] Shah, Ami D., et al. "Breast tissue markers: Why? What's out there? How do I choose?." Clinical imaging 52 (2018): 123-136.

[Sha19] H Shan, A Padole, F Homayounieh, U Kruger, R D Khera, C Nitiwarangkul, M K Kalra and G Wang. Competitive performance of a modularized deep neural network compared to commercial algorithms for low-dose C T image reconstruction. Nature Machine Intelligence. Jun. 10, 2019.

[She17] Dinggang Shen, Guorong Wu, Heung-Il Suk, Deep Learning in Medical Image Analysis, Annual Review of Biomedical Engineering 2017 19:1, 221-248

[She19] Shengfeng Liu, Yi Wang, Xin Yang, Baiying Lei, Li Liu, Shawn Xiang Li, Dong Ni, Tianfu Wang, "Deep Learning in Medical Ultrasound Analysis: A Review," Engineering", Volume 5, Issue 2, 2019, Pages 261-275, https://doi.org/10.1016/j.eng.2018.11.020.

[Sho19] Shorten, C. & Khoshgoftaar, T. M., A survey on Image Data Augmentation for Deep Learning, J Big Data (2019) 6: 60.

[Siegel21] Siegel, R. L., Miller, K. D., Fuchs, H. E., and Jemal, A. (2021). "Cancer statistics, 2021," C A: A Cancer Journal for Clinicians 71(1), 7-33, https://acsjournals.onlinelibrary.wiley.com/doi/abs/10.3322/caac.21654, doi: https://doi.org/10.3322/caac.21654.

[Sim19] Sim, Joo Kyung, Ji Ye Lee, and Hyun Sook Hong. "Differentiation Between Malignant and Benign Lymph Nodes: Role of Superb Microvascular Imaging in the Evaluation of Cervical Lymph Nodes." Journal of Ultrasound in Medicine (2019).

[Son12] Song P, Zhao H, Manduca A, Urban M W, Greenleaf J F, Chen S*, "Comb-push Ultrasound Shear Elastography (CUSE): A Novel Method for Two-dimensional Shear Elasticity Imaging of Soft Tissues", IEEE Transactions on Medical Imaging, vol. 31, issue 9, pp. 1821-1832, 2012.

[Son13a] Song P, Zhao H, Urban M W, Manduca A, Pislaru S V, Kinnick R R, Pislaru C, Greenleaf J F, Chen S*, "Improved Shear Wave Motion Detection Using Pulse-Inversion Harmonic Imaging with a Phased Array Transducer", IEEE Transactions on Medical Imaging, vol. 32, issue 12, pp. 2299-2310, 2013.

[Son13b] Song P, Urban M W, Manduca A, Zhao H, Greenleaf J F, Chen S*, "Comb-push Ultrasound Shear Elastography (CUSE) with Various Ultrasound Push Beams", IEEE Transactions on Medical Imaging, vol. 32, issue 8, pp. 1435-1447, 2013.

[Son14] Song P, Manduca A, Zhao H, Urban M W, Greenleaf J F, Chen S*, "Fast Shear Compounding Using Robust 2-D Shear Wave Speed Calculation and Multi-directional Filtering", Ultrasound in Medicine and Biology, vol. 40, no. 6, pp. 1343-1355, 2014.

[Son15] Song P, Macdonald M C, Behler R H, Lanning J D, Wang M H, Urban M W, Manduca A, Zhao H, Callstrom M R, Alizad A, Greenleaf J F, Chen S*, "Two-dimensional Shear Wave Elastography on Conventional Ultrasound Scanners with Time Aligned Sequential Tracking (TAST) and Comb-push Ultrasound Shear Elastography (CUSE)," IEEE Transactions on Ultrasonics, Ferroelectrics, and Frequency Control, vol. 62, issue 2, pp. 290-302, 2015.

[Son16a] Song P†, Bi X†, Mellema D C, Manduca A, Urban M W, Greenleaf J F, Chen S, "Quantitative Assessment of Left Ventricular Diastolic Stiffness Using Cardiac Shear Wave Elastography: A Pilot Study," Journal of Ultrasound in Medicine, vol. 35, pp. 1419-1427, 2016.

[Son16b] Song P, Mellema D C, Sheedy S P, Meixner D D, Karshen R M, Urban M W, Manduca A, Sanchez W, Callstrom M R, Greenleaf, J F, Chen S*, "Performance of 2-Dimensional Ultrasound Shear Wave Elastography in Liver Fibrosis Detection Using Magnetic Resonance Elastography as the Reference Standard: A Pilot Study," Journal of Ultrasound in Medicine, vol. 35, no. 2, pp. 401-412, 2016.

[Son17a] Song P, Manduca A, Trzasko J D, Chen S*, "Ultrasound Small Vessel Imaging with Block-wise Adaptive Local Clutter Filtering," IEEE Transactions on Medical Imaging, vol. 36, no. 1, pp. 251-262, 2017.

[Son17b] Song P, Trzasko J D, Manduca A, Qiang B, Kadirvel R, Kallmes D F, Chen S*, "Accelerated Singular Value-Based Ultrasound Blood Flow Clutter Filtering with Randomized Singular Value Decomposition (rSVD) and Randomized Spatial Downsampling," IEEE Transactions on Ultrasonics, Ferroelectrics, and Frequency Control, vol. 64, no. 4, pp. 706-716, 2017.

[Son17c] Song P, Manduca A, Trzasko J D, Chen S*, "Letters: Noise Equalization for Ultrafast Plane Wave Microvessel Imaging," IEEE Transactions on Ultrasonics, Ferroelectrics, and Frequency Control, vol. 64, issue 11, pp. 1776-1781, 2017.

[Son17d] Song P, Kolbe A B, Knudsen J M, Sheedy S P, Becker B D, Bruining D H, Chen S, "Quantitative Inflammation Assessment for Crohn's Disease Using Ultrasound Microvessel Imaging: A Pilot Study," Radiological Society of North America (RSNA) 2017, Chicago, IL, 2017.

[Son19] Song Pt, Cuellar Ramos Ct, Tang S, Islam R, Wen H, Huang C, Manduca A, Trzasko J D, Knudsen B E, Lee K H, Chen S*, Lavrov I A*, "Functional Ultrasound Imaging of Spinal Cord Hemodynamic Responses to Electrical Stimulation: A Feasibility Study," Frontiers in Neurology, vol. 10, no. 279, pp. 1-13, 2019.

[Sta14] Stacker, Steven A., et al. "Lymphangiogenesis and lymphatic vessel remodelling in cancer." Nature Reviews Cancer 14.3 (2014): 159.

[Suh17] Suh, Chong Hyun, et al. "The diagnostic performance of shear wave elastography for malignant cervical lymph nodes: A systematic review and meta-analysis." European radiology 27.1 (2017): 222-230.

[Suz17] Suzuki K. Overview of deep learning in medical imaging. Radiol Phys Technol. 2017 September; 10(3): 257-273. doi: 10.1007/s12194-017-0406-5. Epub 2017 Jul. 8. Review. PubMed PMID: 28689314.

[Tad16] Tadayyon H, Sannachi L Gangeh M et al. Quantitative ultrasound assessment of breast tumor response to chemotherapy using a multi-parameter approach. Onoctarget, 7: 45094-45111, 2016.

[Tak19] Takahashi, Ryo, Takashi Matsubara, and Kuniaki Uehara. "Data Augmentation Using Random Image Cropping and Patching for Deep CNNs." IEEE Transactions on Circuits and Systems for Video Technology (2019): 1-1.

[Tan18] Tanaka, Diaki Daiki Ikami, Toshihiko Yamasaki, Kiyoharu Aizawa; Joint Optimization Framework for Learning With Noisy Labels, The IEEE Conference on Computer Vision and Pattern Recognition (CVPR), 2018, pp. 5552-5560.

[Tan20] M. P. Tan, Z. Bi, and E. M. Ong, "The 'twinkle' artifact—A novel method of clip identification to facilitate targeted axillary surgery following neoadjuvant chemotherapy in breast cancer patients," Clinical imaging., vol. 68, pp. 36-44, December 2020.

[Tia17] Tian, Jie, et al. "Application of 3D and 2D quantitative shear wave elastography (SWE) to differentiate between benign and malignant breast masses." Scientific reports 7 (2017): 41216.

[Tre18] Jonathan Tremblay, Aayush Prakash, David Acuna, Mark Brophy, Varun Jampani, Cem Anil, Thang To, Eric Cameracci, Shaad Boochoon, Stan Birchfield; The IEEE Conference on Computer Vision and Pattern Recognition (CVPR) Workshops, 2018, pp. 969-977.

[Tsa18] Tsamardinos, Ioannis, Elissavet Greasidou, and Giorgos Borboudakis. "Bootstrapping the out-of-sample predictions for efficient and accurate cross-validation." Machine learning 107.12 (2018): 1895-1922.

[Wan09] Wang, Yuexiang, et al. "Gray-scale contrast-enhanced ultrasonography of sentinel lymph nodes in a metastatic: breast cancer model." Academic radiology 16.8 (2009): 957-962.

[Wcr10] https://www.wcrf.org/dietandcancer/cancer-trends/worldwide-cancer-data (Last visited Sep. 17, 2019)

[Wir10] L. A. Wirtzfeld, G. Ghoshal, Z. T. Hafez, K. Nam, Y. Labyed, J. A. Anderson, M.-T. Herd, A. Haak, Z. He, R. J. Miller, S. Sarwate, D. G. Simpson, J. A. Zagzebski, T. A. Bigelow, M. L. Oelze, T. J. Hall and W. D. O'Brien Jr. Cross-imaging Platform Comparison of Ultrasonic Backscatter Coefficient Measurements of Live Rat Tumors. Journal of Ultrasound in Medicine, 29, 1117-1123, 2010.

[Wir13] L. A. Wirtzfeld, K. Nam, Y. Labyed, G. Ghoshal, A. Haak, E. Sen-Gupta, Z. He, N. R. Hirtz, R. J. Miller, S. Sarwate, D. G. Simpson, J. A. Zagzebski, T. A. Bigelow, M. L. Oelze, T. J. Hall, and W. D. O'Brien Jr., Techniques and Evaluation from a Cross-platform Imaging Comparison of Quantitative Ultrasound Parameters in an In Vivo Rodent Fibroadenoma Model. IEEE Transactions on Ultrasonics, Ferroelectrics, and Frequency Control, 60, 1386-1400, 2013.

[Wir15] L. A. Wirtzfeld, G. Ghoshal, I. M. Rosado-Mendez, K. Nam, Y. Park, A. D. Pawlicki, R. J. Miller, D. G. Simpson, J. A. Zagzebski, M. L. Oelze, T. J. Hall and W. D. O'Brien Jr. Quantitative ultrasound comparison of MAT and 4T1 mammary tumors in mice and rats across multiple imaging systems. Journal of Ultrasound in Medicine, 34, 1373-1383, 2015.

[Woods19] R. W. Woods, M. S. Camp, N. J. Durr, and S. C. Harvey, "A Review of Options for Localization of Axillary Lymph Nodes in the Treatment of Invasive Breast Cancer," Academic Radiology, vol. 26, no. 6, pp. 805-819, 2019, doi: https://doi.org/10.1016/j.acra.2018.07.002.

[Xia15] Tong Xiao, Tian Xia, Yi Yang, Chang Huang, Xiaogang Wang; Learning From Massive Noisy Labeled Data for Image Classification The IEEE Conference on Computer Vision and Pattern Recognition (CVPR), 2015, pp. 2691-2699.

[Xiq09] Xiaojun, Li, et al. "Local administration of liposomal adriamycin inhibited proliferation of metastatic cells in axillary lymph nodes in rabbit breast cancer model." Journal of Medical Colleges of PLA 24.3 (2009): 161-166.

[You13] Youk, Ji Hyun, et al. "Diagnostic value of commercially available shear-wave elastography for breast cancers: integration into BI-RADS classification with subcategories of category 4." European radiology 23.10 (2013): 2695-2704.

[Zha18] Zhao, Jing, et al. "The value of contrast-enhanced ultrasound for sentinel lymph node identification and characterisation in pre-operative breast cancer patients: A prospective study." European radiology 28.4 (2018): 1654-1661.

[Zho18] Zhi-Hua Zhou, A brief introduction to weakly supervised learning, National Science Review, Volume 5, Issue 1, January 2018, Pages 44-53.

[Zhu19] Zhu, Jiaqi, et al. "3D Super-Resolution US Imaging of Rabbit Lymph Node Vasculature in Vivo by Using Microbubbles." Radiology 291.3 (2019): 642-650.

What is claimed is:

1. A radiological clip device for locating tissue, marked by insertion of the device therein, within a diagnostic image of the marked tissue and surrounding tissue, the device comprising:

an ultrasound receiver configured to generate an electronic activation signal in response to receiving an ultrasound imaging pulse from an ultrasonic imaging array;

an electronic driving circuit configured to generate an electronic identification signal responsive to the electronic activation signal; and an ultrasound transmitter configured to transmit an ultrasound identification (USID) signal based on the electronic identification signal, wherein the ultrasound receiver comprises a Schmitt trigger module configured to generate the electronic activation signal when the ultrasound imaging pulse is received from the ultrasonic imaging array and to refrain from generating the electronic activation signal when scattered ultrasound waves and/or reverb are received based on a threshold received pressure level.

2. The device of claim 1, wherein the USID signal comprises an encoded sequence of narrowband tone bursts associated with an identification protocol to uniquely identify the device within a diagnostic image.

3. The device of claim 1, wherein the USID signal comprises one or more distinct encoded signals that each correspond to a different bit within a multiple-bit identification tag associated with an identification protocol to uniquely identify the device within a diagnostic image.

4. The device of claim 1, wherein the ultrasound transmitter is configured to transmit the USID signal within a frequency bandwidth of one or more ultrasound imaging pulses that the ultrasound receiver is configured to receive from an ultrasonic imaging array.

5. The device of claim 1, wherein the electronic driving circuit is configured to perform signal encoding based on a quantity of bits within a multiple-bit identification tag associated with an identification protocol of the USID to uniquely identify the device within a diagnostic image.

6. The device of claim 1, wherein the ultrasound transmitter is configured to transmit the USID signal at a pressure level similar to a low pressure range associated with scattered ultrasound waves or reverb.

7. The device of claim 1, wherein the ultrasound receiver comprises an electronic circuit coupled with a piezoelectric crystal that receives the ultrasound imaging pulse from the ultrasonic imaging array.

8. The device of claim 1, wherein the ultrasound receiver and the ultrasound transmitter are both electronically coupled with a shared piezoelectric crystal via a switch controlled by a Schmitt trigger to receive the ultrasound imaging pulse from the ultrasonic imaging array at a first time, and responsive to the electronic driving circuit generating the electronic identification signal, transmit the USID signal at a second time.

9. A method of transmitting an ultrasound identification (USID) signal by a radiological clip, the method comprising:

generating, by an ultrasound receiver circuit, an electronic activation signal responsive to receiving an ultrasound imaging pulse from an ultrasonic imaging array, wherein generating the electronic activation signal comprises, determining a received pressure level of an ultrasound signal, determining a threshold received pressure level to distinguish an ultrasound imaging pulse received from the ultrasonic imaging array having a pressure level above the threshold received pressure level from scattered ultrasound waves and/or reverb having a pressure level below the threshold received pressure level, generating the electronic activation signal when the received pressure level is at or above the threshold received pressure level, and refraining from generating the electronic activation signal when the received pressure level is below the threshold received pressure level;

generating, by an electronic driving circuit, an electronic identification signal responsive to the electronic activation signal; and transmitting, by an ultrasound transmitter, a USID signal based on the electronic identification signal.

10. The method of claim 9, wherein generating the electronic identification signal comprises encoding a sequence of narrowband tone bursts associated with an identification protocol to uniquely identify the radiological clip within a diagnostic image.

11. The method of claim 9, wherein generating the electronic identification signal comprises performing signal encoding based on a quantity of bits within a multiple-bit identification tag associated with an identification protocol to uniquely identify the radiological clip within a diagnostic image.

12. The method of claim 9, wherein whether a signal is generated in a particular frequency band component of the USID signal is based on a value of a corresponding bit within a multiple-bit identification tag.

13. The method of claim 9, wherein transmitting the USID signal comprises transmitting the USID signal within a frequency bandwidth of one or more ultrasound imaging pulses that the ultrasound receiver circuit is configured to receive from an ultrasonic imaging array.

14. The method of claim 9, wherein transmitting the USID signal comprises transmitting the USID signal at a pressure level similar to a low pressure range associated with scattered ultrasound waves or reverb.

15. An ultrasound imaging system comprising:

a radiological clip device for locating tissue within a subject, marked by insertion of the radiological clip device therein, within a diagnostic image of the marked tissue and surrounding tissue, the radiological clip device comprising:

an ultrasound receiver configured to generate an electronic activation signal in response to receiving an ultrasound imaging pulse from an ultrasonic imaging apparatus;

an electronic driving circuit configured to generate an electronic identification signal responsive to the electronic activation signal; and an ultrasound transmitter configured to transmit an ultrasound identification (USID) signal based on the electronic identification signal, wherein the ultrasound transmitter is configured to transmit the USID signal at a pressure level similar to a low pressure range associated with scattered ultrasound waves or reverb; and an ultrasound imaging apparatus comprising:

an ultrasound transducer array;

one or more hardware computing processors configured to execute computing instructions;

a non-transitory computer readable medium having stored therein executable instructions which, when executed by the one or more hardware computing processors, cause performance of operations comprising:

causing the ultrasound transducer array to transmit a plurality of transmitted ultrasound imaging pulses toward the subject;

processing electronic signals received from the ultrasound transducer array corresponding to a plurality of returned ultrasound imaging pulses from the subject;

generating an ultrasound image of the subject based on the plurality of transmitted ultrasound imaging pulses and returned ultrasound imaging pulses;

detecting the radiological clip device by processing electronic signals received from the ultrasound transducer array corresponding to the USID signal from the radiological clip device within the subject and within a same imaging field as the returned ultrasound imaging pulses;

determining a location of the radiological clip device within the imaging field of the subject;

determining an ID number corresponding to the radiological clip device based on the USID signal received from the radiological clip device; and displaying, on a display, the ultrasound image of the subject together with an indication of the location of the radiological clip device within the ultrasound image of the subject and the ID number associated with the radiological clip device.

16. The system of claim 15, wherein determining the location of the radiological clip device within the imaging field of the subject comprises employing a pulse-inversion ultrasound to isolate the USID signal, that was received, from the plurality of returned ultrasound imaging pulses received from the subject.

17. The system of claim 15, wherein determining the location of the radiological clip device comprises:

identifying a lateral location of the radiological clip device based on one or more particular imaging scan lines in which the USID signal is detected; and estimating an axial location of the radiological clip device based on a time sample at which the USID signal is first detected within the imaging field.

18. The system of claim 15, wherein determining the ID number corresponding to the radiological clip device comprises:

calculating a frequency spectrum of the USID signal;

determining whether a frequency component of the USID signal is present at each of a plurality of frequency bands corresponding to bits within a multiple-bit identification tag associated with an identification protocol of the USID;

determining a value of each bit within the multiple-bit identification tag based on the determination of a presence of a frequency component of the USID signal at the corresponding frequency band; and determining the ID number based on the determined values of each bit within the multiple-bit identification tag.

19. A radiological clip device for locating tissue, marked by insertion of the device therein, within a diagnostic image of the marked tissue and surrounding tissue, the device comprising:

an ultrasound receiver configured to generate an electronic activation signal in response to receiving an ultrasound imaging pulse from an ultrasonic imaging array;

an electronic driving circuit configured to generate an electronic identification signal responsive to the electronic activation signal; and an ultrasound transmitter configured to transmit an ultrasound identification (USID) signal based on the electronic identification signal, wherein the ultrasound transmitter is configured to transmit the USID signal at a pressure level similar to a low pressure range associated with scattered ultrasound waves or reverb.

20. A radiological clip device for locating tissue, marked by insertion of the device therein, within a diagnostic image of the marked tissue and surrounding tissue, the device comprising:

an ultrasound receiver configured to generate an electronic activation signal in response to receiving an ultrasound imaging pulse from an ultrasonic imaging array;

an electronic driving circuit configured to generate an electronic identification signal responsive to the electronic activation signal; and an ultrasound transmitter configured to transmit an ultrasound identification (USID) signal based on the electronic identification signal, wherein the ultrasound receiver and the ultrasound transmitter are both electronically coupled with a shared piezoelectric crystal via a switch controlled by a Schmitt trigger to receive the ultrasound imaging pulse from the ultrasonic imaging array at a first time, and responsive to the electronic driving circuit generating the electronic identification signal, transmit the USID signal at a second time.

21. A method of transmitting an ultrasound identification (USID) signal by a radiological clip, the method comprising:

generating, by an ultrasound receiver circuit, an electronic activation signal responsive to receiving an ultrasound imaging pulse from an ultrasonic imaging array;

generating, by an electronic driving circuit, an electronic identification signal responsive to the electronic activation signal; and transmitting, by an ultrasound transmitter, a USID signal based on the electronic identification signal, wherein transmitting the USID signal comprises transmitting the USID signal at a pressure level similar to a low pressure range associated with scattered ultrasound waves or reverb.

* * * * *